United States Patent [19]
Ali et al.

[11] Patent Number: 5,643,872
[45] Date of Patent: Jul. 1, 1997

[54] CYCLIC ANTI-AGGREGATORY PEPTIDES

[75] Inventors: Fadia El-Fehail Ali, Cherry Hill, N.J.; James Martin Samanen, Phoenixville, Pa.

[73] Assignee: SmithKline Beecham Corporation, Philadelphia, Pa.

[21] Appl. No.: 296,621

[22] Filed: Aug. 26, 1994

Related U.S. Application Data

[63] Continuation of Ser. No. 630,124, Dec. 19, 1990, abandoned, which is a continuation-in-part of Ser. No. 590,635, Sep. 28, 1990, abandoned, which is a continuation-in-part of Ser. No. 425,906, Oct. 23, 1989, abandoned.

[51] Int. Cl.$^6$ .............. A61K 38/00; C07K 7/06; C07K 5/12; C07K 5/10
[52] U.S. Cl. .............. 514/11; 514/12; 514/13; 514/14; 514/15; 514/18; 530/307; 530/328; 530/330
[58] Field of Search ............ 514/11–15, 18; 530/317, 328, 330

[56] References Cited

U.S. PATENT DOCUMENTS

| | | | |
|---|---|---|---|
| 4,578,079 | 3/1986 | Ruoslahti et al. | |
| 4,683,291 | 7/1987 | Zimmermann et al. | 530/329 |
| 4,857,508 | 8/1989 | Adams et al. | 530/330 |

FOREIGN PATENT DOCUMENTS

| | | |
|---|---|---|
| 265 129 | 4/1988 | European Pat. Off. |
| 0 275 748 | 7/1988 | European Pat. Off. |
| 0341915 | 4/1989 | European Pat. Off. |
| 341 915 | 11/1989 | European Pat. Off. |
| 410 539 | 1/1991 | European Pat. Off. |
| 410 537 | 1/1991 | European Pat. Off. |
| 410 541 | 1/1991 | European Pat. Off. |
| 410 540 | 1/1991 | European Pat. Off. |
| 0411833 | 2/1991 | European Pat. Off. |
| 411 833 | 2/1991 | European Pat. Off. |
| 422 937 | 4/1991 | European Pat. Off. |
| 422 938 | 4/1991 | European Pat. Off. |
| 0422937 | 4/1991 | European Pat. Off. |
| WO89/05150 | 6/1989 | WIPO |
| WO90/02751 | 3/1990 | WIPO |
| WO90/15620 | 12/1990 | WIPO |
| WO 91/01331 | 2/1991 | WIPO |
| WO 91/04247 | 4/1991 | WIPO |
| WO 91/11458 | 8/1991 | WIPO |
| WO91/15224 | 10/1991 | WIPO |
| WO92/00995 | 1/1992 | WIPO |

OTHER PUBLICATIONS

Pierschbacher et al., J. Biol. Chem., 262, 17294(1987).
Plow et al., Proc. Natl. Acad. Sci., 82, 8057 (1985).
Haverstick et al., Blood, 66, 946 (1985).
Pierschbacher et al., Proc. Natl. Acad. Sci., 81, 5985 (1984).
Yasuda et al., Clin. Res., 94, 2, 634A (1986).
Coller et al., Blood, 66, 1456 (1985).
Nievelstein et al., Thromb. and Hemostasis, 58, 2133 (1987).

*Primary Examiner*—Elizabeth C. Weimar
*Assistant Examiner*—S. G. Marshall
*Attorney, Agent, or Firm*—Charles M. Kinzig; Edward T. Lentz

[57] ABSTRACT

This invention relates to compounds of the formula:

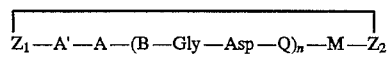

wherein:

A' is absent, Asn, Gln, Ala or Abu;

A is absent or a D- or L-amino acid chosen from Arg, HArg, (Me$_2$)Arg, (Et$_2$)Arg, Abu, Ala, Gly, His, Lys, or an α-R' substituted derivative thereof, Dtc, Tpr and Pro;

B is a D- or L-amino acid chosen from Arg, HArg, NArg, (Me$_2$)Arg, (Et$_2$)Arg and Lys or an α-R' substituted derivative thereof;

Q is absent or a D or L amino acid chosen from Tyr, (Alk)Tyr, Phe, (4'W)Phe, HPhe, Phg, Pro, Trp, His, Ser, (Alk)Ser, Thr, (Alk)Thr, (Alk)Cys, (Alk)Pen, Ala, Val, Nva, Met, Leu, Ile, Nle and Nal, or an α-R' substituted derivative thereof;

M is absent or Gly or a D- or L-amino acid chosen from Glu, Phe, Pro, Lys and Ser or, provided n is 1, B-Gly-Glu-Q;

W is halogen or Alk;

R' is Alk or PhCH$_2$;

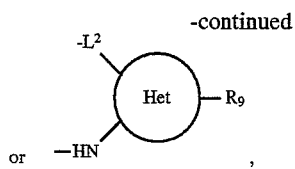

wherein $Z_1$ and $Z_2$ are linked via a covalent bond between $L^1$ and $L^2$; or $Z_1$ and $Z_2$ are, taken together, a covalent bond between the amino terminal residue and the carboxy terminal residue;

$L^1$ and $L^2$ are —S— or —$(CH_2)_p$—;

X is $R_4R_5N$ or H;

Y is H, $CONR_1R_2$ or $CO_2R_2$;

$R_1$ and $R_2$ are H, Alk or $(CH_2)_p$Ar;

$R_3$ and $R_{3'}$ are H, Alk, $(CH_2)_p$Ar or taken together are —$(CH_2)_4$— or —$(CH_2)_5$—;

$R_4$ is H or Alk;

$R_5$ is $R_{11}$, $R_{11}CO$, $R_{11}OCO$, $R_{11}OCH(R_{11'})CO$, $R_{11}NHCH(R_{11'})CO$, $R_{11}SCH(R_{11'})CO$, $R_{11}SO_2$ or $R_{11}SO$;

$R_6$ is Alk, OAlk, halogen or X;

$R_7$ is H, Alk, OAlk, halogen or Y;

$R_8$ and $R_{8'}$ are H, Alk, $(CH_2)_p$Ph, $(CH_2)_p$Nph or taken together are —$(CH_2)_4$— or —$(CH_2)_5$—;

$R_9$ is H, Alk or Y;

$R_{10}$ is H or Alk;

$R_{11}$ and $R_{11'}$ are H, $C_{1-5}$alkyl, $C_{3-7}$cycloalkyl, Ar, Ar—$C_{1-5}$alkyl, Ar—$C_{3-7}$cycloalkyl;

Ar is phenyl or phenyl substituted by one or two $C_{1-5}$alkyl, trifluoromethyl, hydroxy, $C_{1-5}$alkoxy or halogen groups;

n is 1 or 2;

q is 0 or 1; and p is 0, 1, 2 or 3;

or a pharmaceutically acceptable salt thereof;

which are effective for inhibiting platelet aggregation, pharmaceutical compositions for effecting such activity, a method for inhibiting platelet aggregation and clot formation in a mammal, and a method for inhibiting reocclusion of a blood vessel following fibrinolytic therapy.

22 Claims, No Drawings

CYCLIC ANTI-AGGREGATORY PEPTIDES

This is a continuation-in-part of application Ser. No. 07/630,124, filed Dec. 19, 1990, abn, which is a continuation-in-part of U.S. Ser. No. 07/590,635, filed Sep. 28, 1990 and now abandoned, which is a continuation-in-part of U.S. Ser. No. 07/425,906 filed Oct. 23, 1989 and now abandoned.

FIELD OF THE INVENTION

This invention relates to novel peptides which inhibit platelet aggregation, pharmaceutical compositions containing the peptides and methods of using the peptides. In particular, a method of using the peptides of this invention in combination with fibrinolytic agents is disclosed.

BACKGROUND OF THE INVENTION

A thrombus is the result of processes which initiate the coagulation cascade. It is composed of an aggregation of platelets enmeshed in a polymeric network of fibrin. This process is normally initiated as a consequence of tissue injury and has the effect of slowing or preventing blood flow in a vessel. Etiological factors which are not directly related to tissue injury, such as atherosclerotic plaque, inflammation of the blood vessels (phlebitis) and septicemia, may also initiate thrombus formation. In some instances, the inappropriate formation of a thrombus, and subsequent decrease in blood flow, may have pathological consequences, such as stroke, pulmonary embolism and heart disease.

Platelets play a major role in thrombus formation. Current antithrombotic therapy employs agents that modify the platelet/endothelial cell arachidonate-prostaglandin system, such as prostacyclin analogues, cyclooxygenase inhibitors, thromboxane synthesis, inhibitors and thromboxane receptor antagonists; and anti-coagulants, such as heparin. These agents inhibit one or both of two discernible phases of platelet aggregation. The primary phase, which is a response to chemical stimuli, such as ADP (adenosine diphosphate), collagen, epinephrine or thrombin, causes initial activation of the platelets. This is followed by a secondary phase, which is initiated by the platelets themselves, and is characterized by thromboxane $A_2$ ($TxA_2$) synthesis and the release of additional ADP from platelet storage granules, which further activates platelets.

Prostacyclin, also called prostaglandin $I_2$ ($PGI_2$), and stable $PGI_2$ analogues inhibit both the primary and secondary phases of platelet aggregation. However, use of such analogues has been associated with undesirable changes in blood pressure. See Aiken, et al., Prostaglandins, 19, 629–43 (1980).

Cyclooxygenase inhibitors and thromboxane synthetase inhibitors act to block the production of $TxA_2$. $TxA_2$ antagonists block the effects of $TxA_2$ by binding the $TxA_2$ receptor. These therapies act only upon the secondary stage of platelet activation. Use of cyclooxygenase inhibitors has been associated with ulcerogenesis and an adverse effect upon prostacyclin synthesis.

Heparin prevents the activation of fibrinogen by thrombin and thereby prevents the activation of the GPIIb-IIIa receptor by thrombin. This inhibits only the primary phase of platelet aggregation and has little effect upon activation of platelets by other means, such as collagen, ADP and epinephrine.

Cyclooxygenase inhibitors, prostaglandin analogues and heparin all inhibit platelet aggregation indirectly by inhibiting the primary or secondary phase of platelet/fibrinogen activation. There is therefore a need for selective therapeutic products which block platelet aggregation directly, whether it arises from the primary or secondary phase of platelet activation.

Platelet aggregation is believed to be mediated primarily through the GPIIb-IIIa platelet receptor complex. Von Willebrand factor, a plasma protein, and fibrinogen are able to bind and crosslink GPIIb-IIIa receptors on adjacent platelets and thereby effect aggregation of platelets. Fibronectin, vitronectin and thrombospondin are proteins which have also been demonstrated to bind to GPIIb-IIIa. Fibronectin is found in plasma and as a structural protein in the intracellular matrix. Binding between the structural proteins and GPIIb-IIIa may function to cause platelets to adhere to damaged vessel walls.

The importance of the GPIIb-IIIa receptor to platelet aggregation has been demonstrated by methods which mask the receptor. Thus, Coller et al, (Blood, 66, 1456–9 (1985)) have shown that antibodies to this complex inhibit platelet aggregation in dogs induced by ADP.

Peptide fragments of human plasma fibronectin and synthetic peptides containing the RGD sequence which promote cell attachment and enhance phagocytosis are disclosed in U.S. Pat. Nos. 517,686, 4,589,881, 4,661,111 and 4,614,517. Linear and cyclic peptides containing an RGD sequence have also be reported in WO 89/05150 (PCT US88/04403). Peptides which contain an RGD sequence have been reported to inhibit platelet aggregation. Nievelstein et al, (Thromb. and Hemostasis, 58, 2133(1987)) have reported that -RGDS- peptides inhibit thrombin induced aggregation and adhesion of platelets to fibronectin, and may interact through the GPIIb-IIIa complex. U.S. Pat. No. 4,683,291 discloses peptides containing Arg and Lys and an -RGD- sequence which inhibit binding of fibrinogen to platelets and inhibit platelet aggregation. A disadvantage of these peptides is their poor stability in plasma and their low potency. EP 0 275 748 discloses linear tetra- to hexapeptides and cyclic hexa- to octapeptides which bind to the GPIIb-IIIa receptor and inhibit platelet aggregation. The cyclic peptides reported are formed via a disulfide bridge between two cysteinyl residues. Other linear and cyclic peptides, the disclosure of which are incorporated herein by reference, are reported in EP-A 0 341 915. These cyclic structures comprise a disulfide ring formed by two sulfhydryl-bearing aliphatic amino acid residues.

The instant invention provides cyclic compounds in which the cyclic structure comprises a homodetic peptide wherein the ring is formed by a peptide bond, or a heterodetic peptide wherein the ring is formed by an alkylene, sulfide or disulfide bridge. This invention further discloses cyclic compounds in which the unit B-Gly-Asp-Q, as hereinafter defined in formula (I), is repeated more than once. Construction of such unusual ring structures surprisingly results in pharmacologically active compounds. It has further been discovered that neither a terminal amino group or a terminal carbonyl group is required for anti-aggregatory activity. The compounds of this invention are further resistant to plasma proteases and show a selectivity for inhibition of binding to the fibrinogen receptor over other integrin receptors, such as vitronectin or fibronectin. Thus, an advantage to the compounds of this invention is their ability to inhibit platelet aggregation without appreciably inhibiting the adhesion of platelets to other integrin receptors.

Recent advances for treatment of occluded arteries and deep vein thrombosis employ fibrinolytic agents to lyse thrombi or emboli in order to reestablish or improve blood flow. Fibrinolytic agents, such as tissue plasminogen activator (tPA), urokinase (UK), pro-Urokinase(pUK), and streptokinase (SK), and mutants and derivatives thereof, are proteolytic enzymes which cause fibrin to be hydrolyzed at specific sites and thereby fragment the fibrin network. Their action in vivo is to proteolytically activate plasminogen in the blood to form plasmin, which causes lysis of the fibrin clot. Lysis of fibrin into smaller peptides has the effect of solubilizing the thrombus or embolus. A recurrent problem with such therapy, however, is the reocclusion of the blood vessel due to formation of a secondary thrombus.

Fibrinolytic therapy is most commonly used for reestablishing flow in a thrombosed blood vessel. However, fibrinolytic therapy does not reverse the factors responsible for the initiation of the thrombus. For this reason, anticoagulants such as heparin are often used to prevent reocclusion. In fact, patients which have a high degree of stenosis in an artery are at extremely high risk of rethrombosis after reperfusion, even in the presence of high doses of heparin. See Gold et al., *Circ.*, 73, 347–52 (1986). In addition, use of SK and tPA has been associated with platelet hyperaggregability. See Ohlstein, et al., *Thromb. Res.*, 4, 575–85 (1987). Treatment with higher doses of tPA can be associated with systemic bleeding and is not recommended for preventing reocclusion. There is, therefore, a need for a method for preventing rethrombosis after fibrinolytic therapy.

U.S. patent application Ser. No. 917,122 discloses $TxA_2$ antagonists for use in a method for inhibiting reocclusion following reperfusion and for lowering the dose of tPA required for fibrinolysis. Yasuda et al. (*Clin. Res.*, 34, 2 (1986)) have demonstrated that reocclusion by fibrin rich platelet thrombi, after thrombolysis with tPA, may be inhibited by a murine monoclonal antibody to GPIIb-IIIa in dogs. This invention discloses a new method for inhibiting reocclusion of a blood vessel by administering peptides which directly inhibit platelet aggregation.

SUMMARY OF THE INVENTION

In one aspect this invention is a compound of the formula (I):

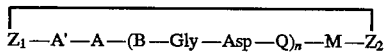  (I)

wherein:

A' is absent, Asn, Gln, Ala or Abu;

A is absent or a D- or L-amino acid chosen from Arg, HArg, $(Me_2)Arg$, $(Et_2)Arg$, Abu, Ala, Gly, His, Lys, or an α-R' substituted derivative thereof, Dtc, Tpr and Pro;

B is a D- or L-amino acid chosen from Arg, HArg, NArg, $(Me_2)Arg$, $(Et_2)Arg$ and Lys or an α-R' substituted derivative thereof;

Q is absent or a D- or L-amino acid chosen from Tyr, (Alk)Tyr, Phe, (4'W)Phe, HPhe, Phg, Pro, Trp, His, Ser, (Alk)Ser, Thr, (Alk)Thr, (Alk)Cys, (Alk)Pen, Ala, Val, Nva, Met, Leu, Ile, Nle and Nal, or an α-R' substituted derivative thereof;

M is absent or Gly or a D- or L-amino acid chosen from Glu, Phe, Pro, Lys and Ser or, provided n is 1, B-Gly-Glu-Q;

W is halogen or Alk;

R' is Alk or $PhCH_2$;

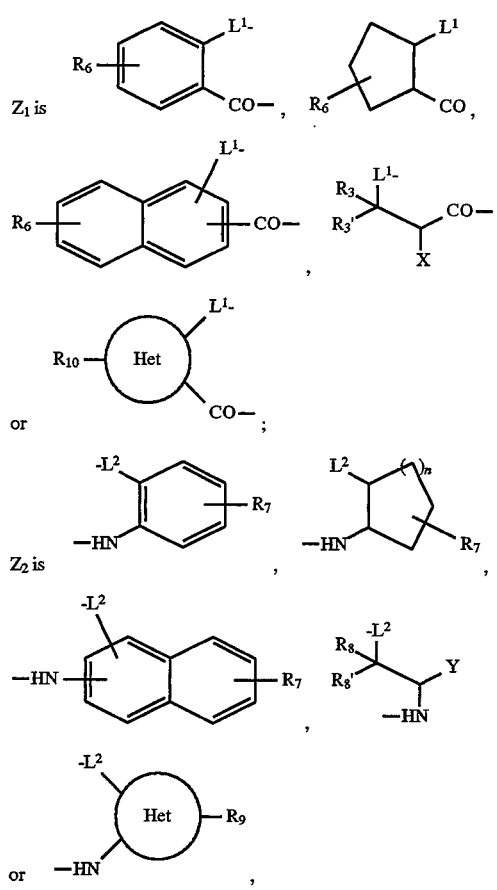

wherein $Z_1$ and $Z_2$ are linked via a covalent bond between $L^1$ and $L^2$; or $Z_1$ and $Z_2$ are, taken together, a covalent bond between the amino terminal residue and the carboxy terminal residue;

$L^1$ and $L^2$ are —S— or $—(CH_2)_p—$;

X is $R_4R_5N$ or H;

Y is H, $CONR_1R_2$ or $CO_2R_2$;

$R_1$ and $R_2$ are H, Alk or $(CH_2)_pAr$;

$R_3$ and $R_{3'}$ are H, Alk, $(CH_2)_pAr$ or taken together are $—(CH_2)_4—$ or $—(CH_2)_5—$;

$R_4$ is H or Alk;

$R_5$ is $R_{11}$, $R_{11}CO$, $R_{11}OCO$, $R_{11}OCH(R_{11'})CO$, $R_{11}NHCH(R_{11'})CO$, $R_{11}SCH(R_{11'})CO$, $R_{11}SO_2$ or $R_{11}SO$;

$R_6$ is Alk, OAlk, halogen or X;

$R_7$ is H, Alk, OAlk, halogen or Y;

$R_8$ and $R_{8'}$ are H, Alk, $(CH_2)_pPh$, $(CH_2)_pNph$ or taken together are $—(CH_2)_4—$ or $—(CH_2)_5—$;

$R_9$ is H, Alk or Y;

$R_{10}$ is H or Alk;

$R_{11}$ and $R_{11'}$ are H, $C_{1-5}$alkyl, $C_{3-7}$cycloalkyl, Ar, Ar—$C_{1-5}$alkyl, Ar—$C_{3-7}$cycloalkyl;

Ar is phenyl or phenyl substituted by one or two $C_{1-5}$alkyl, trifluoromethyl, hydroxy, $C_{1-5}$alkoxy or halogen groups;

n is 1 or 2;

q is 0 or 1; and p is 0, 1, 2 or 3 and pharmaceutically active salts thereof;
provided that when n is 1 and $Z_1$ is X-Cys, X-Pen or X-APmp, $Z_2$ is not Cys-Y, Pen-Y or APmp-Y.

This invention is also a pharmaceutical composition for inhibiting platelet aggregation and clot formation, which comprises a compound of formula (I) and a pharmaceutically acceptable carrier.

This invention is further a method for for inhibiting platelet aggregation in a mammal in need thereof, which comprises internally administering an effective amount of an compound of formula (I).

In another aspect, this invention provides a method for inhibiting reocclusion of an artery or vein in a mammal following thrombolysis, which comprises internally administering an effective amount of a fibrinolytic agent and a compound of formula (I). In combination with known fibrinolytics, such as streptokinase (SK), urokinase (UK), pro-urokinase (pUK) and tissue plasminogen activator (tPA) and variants or mutants thereof, these compounds are useful for inhibiting rethrombosis.

This invention is also a pharmaceutical composition for effecting thrombolysis and reperfusion, and inhibiting reocclusion in an artery or vein in a mammal, which comprises a fibrinolytic and a compound of formula (I) in a pharmaceutical carrier.

Finally, this invention is a kit for use in a method for effecting thrombolytic therapy, which comprises, in a container, a fibrinolytic and a compound of formula (I).

DETAILED DESCRIPTION OF THE INVENTION

This invention discloses cyclic peptide-like compounds comprising the sequence Gly-Asp. The compounds of this invention inhibit platelet aggregation and are believed to interact with the GPIIb-IIIa receptor and other adhesion proteins.

The compounds of this invention are peptides of formula (I), as previously described.

B is suitably Arg or HArg, or an α-R' substituted derivative of Arg or HArg. B is preferably MeArg.

Preferably A is Dtc, Tpr or Pro, when A' is Asn, Gln, Ala or Abu.

Suitably Y is $CONH_2$ or $CO_2H$.

In one preferred subgeneric group of compounds $L^1$ and $L^2$ are each S.

Suitably $Z_2$ is

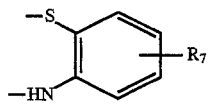

or Pcs.

Suitably $Z_1$ is

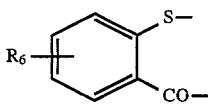

or Cys.

Suitably $R_6$ and $R_7$ are H.
Suitably M is absent.
Suitably A' is absent.
Suitably A is Sar or is absent.

In another preferred subgeneric group of compounds $Z_1$ and $Z_2$ are together a covalent bond.

Suitably, A and A' are absent, n is 2 and $Z_1$ and $Z_2$ are together a covalent bond.

Q is suitably Ser, (Me)Ser, Thr, Tyr, Phe or Nal, when n is 2. Q is preferably Phe.

Preferably, if $L^1$ and $L^2$ are S, and if $Z_1$ is

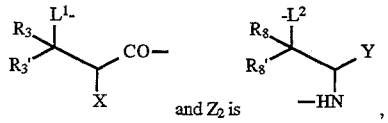

$R_8$ is phenyl.

In another subgeneric group of compounds $L^1$ and $L^2$ are each $CH_2$.

The meaning of X in the formulae herein depicted with regard to X-Cys, X-Pen and X-APmp is intended to denote the amino group of these amino acids. In like manner, when used with Cys-Y, Pen-Y and APmp-Y, Y refers to the substituted carboxyl group of these amino acids. It will be understood that when $Z_1$ and $Z_2$ are not an aryl moiety, they may have one or two chiral centers and that this invention includes each unique nonracemic compound which may be synthesized and resolved by conventional techniques.

When $Z_1$ or $Z_2$ are phenyl, a mercapto or alkylene group is in the 1 position, the amino/carboxyl group is in the 2 position, and they may be substituted in the 3, 4 or 5 position by $R_6$ or $R_7$. When $Z_1$ or $Z_2$ are naphthyl, the mercapto or alkylene group may be in the 1 or 2 position, the amino/carboxyl group bears an ortho orientation and they may be further substituted on any position of the naphthyl ring.

Het represents a substituted heterocycle. Representative heterocycles are pyridine, pyrrole, pyrrolidine, imidazole, triazole, thiophene, furan, and thiazole. Such heterocycles form a macrocyclic ring within the peptide via two ortho situated substituents. For example, $Z_1$ is a heterocyclic carboxylic acid, which is attached to the peptide through the carboxyl and to $Z_2$ via an ortho situated bridge as defined by $L^1$. Similarly, $Z_2$ may be a heterocyclic amine, which is attached to the peptide through the amine and to $Z_1$ via an ortho situated bridge defined as $L^2$.

$C_{1-4}$alkyl as applied herein is meant to include methyl, ethyl, n-propyl, isopropyl, n-butyl and isobutyl. Ar as applied herein means phenyl or phenyl substituted by one or two $C_{1-4}$alkyl, trifluoromethyl, $C_{1-4}$alkoxy, hydroxy, or halogen groups.

This invention includes compounds in which any of the peptide linkages, —CONH—, are replaced by an isosteric linkage. Examples of peptide isosteres are —NHCO—, —CH=CH—, —$CH_2CH_2$—, —$COCH_2$—, —COO—, —$CHOHCH_2$—, —$CH_2NR_4$—, —CSNH— and —$CH_2S$—.

Specific compounds of this invention are:
cyclo(S,S)-Mba-Arg-Gly-Asp-Cys-$NH_2$;
$N^\alpha$-Ac-cyclo(S,S)-Cys-Arg-Gly-Asp-Man;
cyclo(S,S)-Mba-MeArg-Gly-Asp-Man;
cyclo(S,S)-Mba-MeArg-Gly-Asp-Pcs-$NH_2$;
cyclo-(S,S)-Mba-Sar-Arg-Gly-Asp-Man;
cyclo-(S,S)-Mba-Sar-MeArg-Gly-Asp-Man;
cyclo-(S,S)-Mba-Arg-Gly-Asp-Man;
cyclo-(S,S)-Mba-D-MeArg-Gly-Asp-Man;
cyclo-(S,S)-Mba-MeArg-Gly-Asp-N-Me-Man;
$N^\alpha$Ac-cyclo-(S,S)-Cys-MeArg-Gly-Asp-(2R,3S)Pcs-$NH_2$;
$N^\alpha$Ac-cyclo-(S,S)-Cys-MeArg-Gly-Asp-(2R,3R)Pcs-$NH_2$;
$N^\alpha$Ac-cyclo-(S,S) Cys-Arg-Gly-Asp-Ser-Arg-Gly-Asp-Ser-Cys-$NH_2$;
$N^\alpha$Ac-cyclo-(S,S)-Cys-Arg-Gly-Asp-Ser-Arg-Gly-Asp-Ser-Pen-$NH_2$;

N$^\alpha$Ac-cyclo-(S,S) Cys-Arg-Gly-Asp-Ser-MeArg-Gly-Asp-Ser-Cys-NH$_2$;

N$^\alpha$Ac-cyclo-(S,S)-Cys-MeArg-Gly-Asp-Ser-Arg-Gly-Asp-Ser-Cys-NH$_2$;

N$^\alpha$Ac-cyclo-(S,S)-Cys-Arg-Gly-Asp-Ser-Lys-Gly-Glu-Ser-Cys-NH$_2$;

cyclo-(1$^\alpha$,6$^\gamma$)-Gly-Arg-Gly-Asp-Ser-Glu-NH$_2$;

cyclo(1$^\alpha$,6$^\gamma$)-Gly-MeArg-Gly-Asp-Ser-Glu-NH$_2$;

cyclo-(1,8)-Arg-Gly-Asp-Phe-Arg-Gly-Asp-Phe;

cyclo-(1,8)-MeArg-Gly-Asp-Phe-Arg-Gly-Asp-Phe;

cyclo-(1,10)-Pro-Arg-Gly-Asp-D-Phe-Pro-Arg-Gly-Asp-D-Phe;

cyclo-(1,6)-Gly-Pro-Arg-Gly-Asp-D-Pro;

cyclo-(1,6)-Pro-Gly-Arg-Gly-Asp-D-Pro;

cyclo-(1,6)-Gly-Arg-Gly-Asp-Ser-Pro;

cyclo-(1,6)-Pro-Arg-Gly-Asp-Gly-D-Pro;

cyclo-(1,6)-Pro-Arg-Gly-Asp-Gly-D-Phe;

cyclo-(1,5)-D-Ala-Arg-Gly-Asp-Ser;

cyclo-(1,5)-Ala-Arg-Gly-Asp-D-Ser; and cyclo-(1,3)-N$^\alpha$-[2-(2-(2-amido-phenyl)ethyl)benzoyl]-MeArg-Gly-Asp-amide.

Preferred compounds of this invention are:
cyclo-(S,S)-Mba-MeArg-Gly-Asp-Man;
cyclo-(S,S)-Mba-Sar-MeArg-Gly-Asp-Man;
N$^\alpha$Ac-cyclo-(S,S)-Cys-MeArg-Gly-Asp-Pcs; and
cyclo(1,8)-MeArg-Gly-Asp-Phe-Arg-Gly-Asp-Phe.

The nomenclature commonly used in the art is used herein to describe the peptides.

| Amino Acid | 3 letter code | 1 letter code | Amino acid | 3 letter code | 1 letter code |
|---|---|---|---|---|---|
| Alanine | Ala | A | Leucine | Leu | L |
| Arginine | Arg | R | Lysine | Lys | K |
| Asparagine | Asn | N | Methionine | Met | M |
| Aspartic Acid | Asp | D | Phenylalanine | Phe | F |
| Cysteine | Cys | C | Proline | Pro | P |
| Glutamine | Gln | Q | Serine | Ser | S |
| Glutamic Acid | Glu | E | Threonine | Thr | T |
| Glycine | Gly | G | Tryptophan | Trp | W |
| Histidine | His | H | Tyrosine | Tyr | Y |
| Isoleucine | Ile | I | Valine | Val | V |
| Asparagine or Aspartic Acid | | | | Asx | B |
| Glutamine or Glutamic Acid | | | | Glx | Z |

In accordance with conventional representation, the amino terminus is on the left and the carboxy terminus is on the right. Unless specified otherwise, all chiral amino acids (AA) are assumed to be of the L-absolute configuration. Pen refers to L-penicillamine or β,β dimethyl cysteine, APmp refers to 2-amino-3,3-cyclopentamethylene-3-mercaptopropionic acid, Dtc refers to 5,5-dimethylthiazolidine-4-carboxylic acid, Tpr refers to thiazolidine-4-carboxylic acid, Mpa refers to 3-mercaptopropionic acid, Pmp refers to 3,3-cyclopentamethylene-3-mercaptopropionic acid, Mdp refers to 3-mercapto-3-methylbutanoic acid, Pcs refers to 3-phenyl cysteine racemic in the 3 position, (3S)Pcs refers to (2R, 3S)-3-phenylcysteine, (3R)Pcs refers to (2R,3R)-3-phenylcysteine, Man refers to 2-mercapto-aniline, Mba refers to 2-mercapto-benzoic acid, HArg refers to homoarginine, NArg refers to norarginine, (Me$_2$)Arg refers to N',N''-dimethyl arginine, (Et$_2$)Arg refers to N',N''-diethyl arginine, Nva refers to norvaline, Nle refers to norleucine, α-MeAsp refers to N$^\alpha$-methyl aspartic acid, Nal refers to beta-2-naphthyl alanine, Phg refers to phenylglycine, HPhe refers to homophenylalanine, Abu refers to 2-amino butyric acid, (Alk)Tyr refers to O—C$_{1-4}$alkyl-tyrosine, (Alk)Ser refers to O—C$_{1-4}$alkyl-serine, (Alk)Thr refers to O—C$_{1-4}$alkyl-threonine, (Alk)Cys refers to S—C$_{1-4}$alkyl-cysteine, (Alk)Pen refers to S—Cl$_{1-4}$alkyl-penicillamine, (4'W)Phe refers to phenylalanine substituted in the 4 position of the phenyl ring by W, t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the carbobenzyloxy radical, BrZ refers to the o-bromobenzyloxycarbonyl radical, ClZ refers to the o-chlorobenzyloxycarbonyl radical, Bzl refers to the benzyl radical, 4-MBzl refers to the 4-methyl benzyl radical, Ac refers to acetyl, Alk refers to C$_{1-4}$ alkyl, Ph refers to phenyl, Nph refers to 1- or 2-naphthyl, cHex refers to cyclohexyl, DCC refers to dicyclohexylcarbodiimide, DMAP refers to dimethylaminopyridine, DIEA refers to diisopropylethyl amine, EDC refers to N-ethyl-N'(dimethylaminopropyl)carbodiimide, HOBT refers to 1-hydroxybenzotriazole, THF refers to tetrahydrofuran, DMF refers to dimethyl formamide, PPA refers to 1-propanephosphonic acid cyclic anhydride, DPPA refers to diphenylphosphoryl azide, BOP refers to benzotriazol-1-yloxy-tris(dimethylamino)phosphonium hexafluorophosphate, HF refers to hydrofluoric acid and TFA refers to trifluoroacetic acid.

Coupling reagents as used herein denote reagents which may be used to form peptide bonds. Typical coupling reagents are carbodiimides, activated anhydrides and esters and acyl halides. Reagents such as EDC, DCC, DPPA, PPA, BOP reagent, HOBT, N-hydroxysuccinimide and oxallyl chloride are typical.

α-R' substituted derivatives of the amino acids of this invention, which may be denoted as (α-R')AA, indicate amino acids which are mono-substituted on the α-amino group by R', wherein R' is Alk or benzyl. R' is preferably methyl. N$^\alpha$-methyl arginine and N$^\alpha$-methyl glycine, which are (α-Me)Arg and (α-Me)Gly respectively, are also denoted herein as MeArg and Sar (sarcosine) in accordance with past conventional notation. All other N-α-substituted amino acids will carry the designation α- in their representation. Thus, amino acids which may be alkylated upon a mercaptan, guanidino or hydroxyl group, such as Tyr, Ser, Thr, Cys or Pen, are distinguished by an absence of this designation. Thus, (α-Me)Ser is N$^\alpha$-methyl serine, (Me)Ser is O-methyl serine, (α-Me,Et)Ser is N$^\alpha$-methyl, O-ethyl serine and (α-Me,Et$_2$)Arg is N$^\alpha$-methyl-N',N''-diethyl arginine.

The peptides are prepared preferably by the solid phase technique of Merrifield (J. Am. Chem. Soc., 85, 2149 (1964)), although solution methods known to the art may be successfully employed. A combination of solid phase and solution synthesis may be used, as in a convergent synthesis in which di-, tri-, tetra-, or penta-peptide fragments may be prepared by solid phase synthesis and either coupled or further modified by solution synthesis. The methods of peptide synthesis generally set forth by Ali et al. in J. Med. Chem., 29, 984 (1986) and J. Med. Chem., 30, 2291 (1987) were employed to produce most of the peptides of this invention and are incorporated herein by reference.

The reactive functional groups of the sidechains of each amino acid or peptide are suitably protected as known in the peptide art. For example, the Boc, Cbz or Fmoc group may be used for protection of an amino group, especially an α-amino group. The Boc group is generally preferred for protection of the α-amino group. A t-Bu, cHex or benzyl ester may be used for the protection of the side chain carboxyl of Asp or Glu. A benzyl group or suitably substituted benzyl group is used to protect the mercapto group of cysteine, or other thiol containing residues; or the hydroxyl of serine or threonine. The tosyl group may be used for protection of the imidazolyl group of His, and tosyl or nitro group for protection of the guanidino nitrogen of Arg. A suitably substituted carbobenzyloxy group or benzyl group may be used for the hydroxyl group of Tyr, Ser or Thr, or the ε-amino group of lysine. The phthalamido group may also be used for the protection of the ε-amino group of lysine. Suitable substitution of the carbobenzyloxy or benzyl protecting groups is ortho and/or para substitution with chloro, bromo, nitro or methyl, and is used to modify the reactivity of the protective group. Cysteine and other sulfur-containing amino acids may also be protected by formation of a disulfide with a thioalkyl or thioaryl group. Except for the Boc group, the protective groups are, most conveniently, those which are not removed by mild acid treatment. These protective groups are removed by such methods as catalytic hydrogenation, sodium in liquid ammonia or HF treatment, as known in the art.

If solid phase methods are used, the peptide is built up sequentially starting from the carboxy terminus and working toward the amino terminus of the peptide. Solid phase synthesis is begun by covalently attaching the C terminus of a protected amino acid to a suitable resin, such as a benzhydrylamine resin (BHA), methylbenzhydrylamine resin (MBHA), chloromethyl resin (CMR), hydroxymethyl resin (HMR) or SASRIN resin, as is generally set forth in U.S. Pat. No. 4,244,946. A BHA or MBHA support resin is used if the carboxy terminus of the product peptide is to be a carboxamide. A CMR support is generally used if the carboxy terminus of the product peptide is to be a carboxyl group, although this may also be used to produce a carboxamide or ester.

Once the first protected amino acid (AA) has been coupled to the desired resin, the amino group is deprotected by mild acid treatment, and the free carboxyl of the second protected AA is coupled to this amino group. This process is carried out sequentially, without isolation of the intermediate, until the desired peptide has been formed. The completed peptide may then be deblocked and/or split from the carrying resin in any order.

Treatment of a CMR supported peptide with alkali in aqueous alcohol splits the peptide from the resin and produces the carboxy terminal amino acid as a carboxylic acid. Treatment of a CMR supported peptide with ammonia or alkyl amines in an alcoholic solvent provides a carboxamide or alkyl carboxamide at the carboxy terminus.

If an ester is desired, the CMR resin may be treated with an appropriate alcohol, such as methyl, ethyl, propyl, butyl or benzyl alcohol, in the presence of triethylamine to cleave the peptide from the resin and produce the ester directly.

Esters of the peptides of this invention may also be prepared by conventional methods from the carboxylic acid precursor. Typically, the carboxylic acid is treated with an alcohol in the presence of an acid catalyst. Alternatively, the carboxylic acid may be converted to an activated acyl intermediate, such as an acid halide, and treated with an alcohol, preferably in the presence of a base.

Methods of producing C-terminal esters of the peptides without esterification of the side chain carboxyl group of aspartic acid are slightly more elaborate, but are well known to those skilled in the art of peptide synthesis. For example, the synthesis is begun with an ester of the C terminal amino acid, or of a dipeptide, and coupled via solution phase synthesis to an appropriately side-chain-protected aspartic acid residue. The side chain carboxyl group is then selectively deprotected and coupled to a chloromethyl resin (CMR). The amino group is liberated and solid phase peptide synthesis is employed. Subsequent cleavage from the resin, using HF, produces the desired side chain carboxylic acid, whilst the carboxy terminus of the peptide remains as an ester. In a similar manner, if one begins the synthetic sequence with the alkyl amide of an appropriately protected amino acid or dipeptide, one obtains the corresponding C-terminal alkyl amide of the peptide.

For producing esters and substituted amides in such a process, suitable protecting groups for the 4-carboxyl group of aspartic acid are benzyl esters and halogen- or alkyl-substituted benzyl esters. When the amino group is protected by the Boc group, the benzyl ester protecting group may be selectively removed by hydrogenation and coupled to a CMR support.

If $Z_2$ possesses no carboxylic acid moiety or there are benzyl or substituted benzyl protecting groups (such as for the hydroxyl, thiol or amino group) on the amino acid (or dipeptide) which is to be coupled to the aspartic acid prior to attachment to the resin, a t-butyl ester or other acid labile group is suitable for protecting the side-chain carboxyl of the aspartic acid. In this case the amino group of the aspattic acid is protected by a base labile group, such as the fluorenylmethoxycarbonyl moiety (Fmoc). After solution phase coupling of the aspartic acid to an aniline, amine or amino acid (or dipeptide), selective deprotection of the t-butyl ester is accomplished by mild acid hydrolysis and the side chain carboxyl is coupled to the resin by conventional methods. The fluorenylmethoxycarbonyl group is then removed by mild base for subsequent solid phase peptide synthesis. When the terminal residue, $Z_2$, is a substituted or unsubstituted o-mercapto aryl amine, which bears no carboxyl substituent, this method is particularly effective.

The preferred method for cleaving a peptide from the support resin iS to treat the resin supported peptide with anhydrous HF in the presence of a suitable cation scavenger, such as anisole or dimethoxy benzene. This method simultaneously removes all protecting groups, except a thioalkyl group protecting sulfur, and splits the peptide from the resin. Peptides hydrolyzed in this way from the CMR are carboxylic acids, those split from the BHA resin are obtained as carboxamides.

In one preferred subgeneric group of compounds, $L^1$ is S and $L^2$ is S. The cyclic disulfide compounds of formula (I) are produced from a corresponding linear peptide of formula (II),

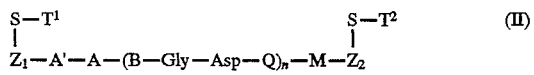

wherein A', A, B, Q, M, and n, are as defined hereinbefore for structure (I), $Z_1$ is

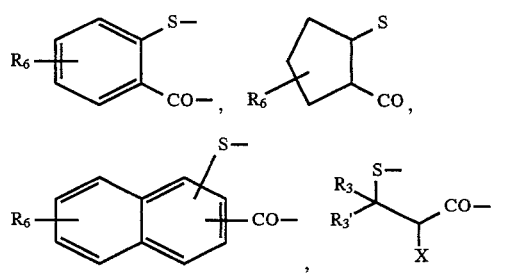

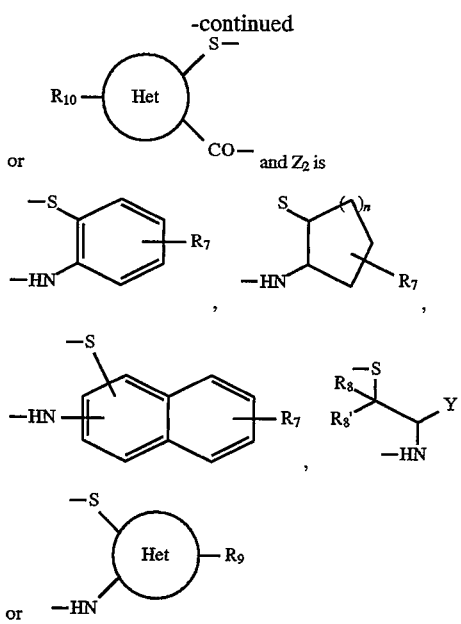

with any chemically reactive centers optionally protected as previously described, and the sulfur moeity of $Z_1$ or $Z_2$ is substituted by $T^1$ or $T^2$. $T^1$ and $T^2$ are displaceable groups such as a thioalkyl, thioaryl group, substituted benzyl group or hydrogen. Examples of suitable displaceable groups are hydrogen, $C_{1-4}$alkylthio, especially ethylthio, benzyl and the 4-methyl benzyl group. Preferably T1 and T2 are both hydrogen, or one of $T^1$ and $T^2$ is hydrogen and the other is $C_{1-4}$alkylthio.

Formation of the disulfide bond may be accomplished by either one of two general methods. If the sulfur-containing amino acids of the linear peptide are protected differently, in such a manner as to allow formation of a mono mercaptan, cyclization may be effected by base catalyzed nucleophilic displacement of the protecting group of the second sulfur-containing amino acid. Groups which are especially useful as displaceable protecting groups are thioalkyl or thioaryl groups. Exemplary of this method is the protection of one sulfur-containing amino acid by the thioethyl group, and protection of the second by a substituted benzyl group. Deprotection of such a peptide by HF removes the benzyl group from one amino acid, while leaving the second protected as an ethyl disulfide. Stirring this mercapto/disulfide in dilute solution at a pH of about 7 to 8 effects displacement of the thioethyl group and cyclization of the linear peptide.

If the corresponding linear peptide of formula (II) is completely deprotected and produced as a dimercaptan, any oxidizing agent known to the art to be capable of converting a dimercaptan to a disulfide may be used. Exemplary of such agents are an alkali metal ferricyanide, especially potassium or sodium ferricyanide, oxygen gas, diiodomethane or iodine. Thus, treatment of a compound of formula (II) with an oxidant causes cyclization of the compound. The reaction is conducted in a suitable inert solvent, such as aqueous methanol or water, at temperatures from about 0° to about 40° C., under high dilution. The pH is usually maintained at about 7 to about 8. Cyclization may be performed upon the peptide while it is still attached to the support resin or while other functional groups are still protected, but it is preferrably performed on the deprotected free peptide.

Accordingly, this invention is also a process for preparing a compound of formula (III),

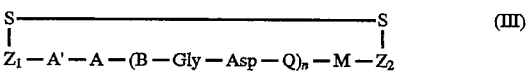

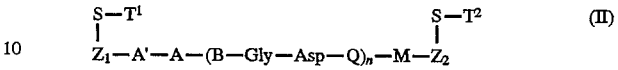

wherein A', A, B, Q, M, $Z_1$, $Z_2$ and n are as previously defined for formula (I), which comprises, a) oxidatively cyclizing a compound of the formula (II),

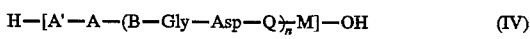

wherein A', A, B, Q, M, $Z_1$, $Z_2$ and n are as previously defined for formula (I), and $T^1$ and $T^2$ are H, or b) nucleophilically cyclizing a compound of formula (II) by treating with base, wherein A', A, B, Q, M, $Z_1$, $Z_2$ and n are as previously defined for formula (I), and one of $T^1$ and $T^2$ is a displaceable group and the other is H.

Another subgeneric group of compounds are homodetic peptides wherein $Z_1$ and $Z_2$ are, taken together, a covalent bond. These peptides are prepared from the linear peptides of formula (IV), wherein A', A, B, Q, M and n $$H-[A'-A-(B-Gly-Asp-Q)_n-M]-OH \quad (IV)$$

are as hereinbefore defined for formula (I). These linear peptides are prepared in a manner to liberate and cyclize the terminal amino group and terminal carboxyl group of the peptide while the side chain carboxyl of the Asp remains protected. Cyclization may then be effected by common peptide bond forming reagents, such as carbodiimides or activated anhydrides. Diphenyl phosphoryl azide, the BOP reagent, 1-propanephosphonic acid cyclic anhydride and DCC/HOBT are examples of such reagents. It will be apparent that the terminal amino group of peptide (IV), denoted as H—[HN—AA—], and the terminal carboxyl group, denoted as [—AA—CO]—OH, may be attached to any residue of the peptide (i.e. A', A, B, Gly, Asp, Q or M), since the formation of any peptide bond in the cyclic peptides may be effected in the last step to prepare the same final compound.

When Asp or Glu are present in the peptide, there is a possibility of cyclization through either the sidechain β-carboxy (Asp) or γ-carboxy (Glu) group or the terminal carboxy group of the amino acid. Cyclization through the terminal carboxy group is preferred for Asp. Cyclization through the γ-carboxy group is suitable for Glu. Methods common to the art, as more fully illustrated herein, are available for cyclizing through either carboxyl group.

Accordingly, this invention is also a process for preparing a compound of the formula (V),

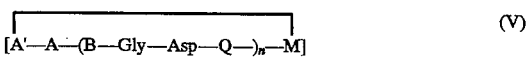

wherein A', A, B, Q, M and n are as defined for compound (I), which comprises, i) cyclizing with a coupling reagent a compound of the formula (IV),

wherein H— and —OH represent the amino and carboxyl residues of any two adjacent residues in the cyclic peptide (IV), and A', A, B, Q, M and n are as defined for compound (I) with any reactive sidechain groups optionally protected, and ii) removing any protecting groups.

If $Z_1$ and $Z_2$ are connected via an alkylene bridge, then the amino acid $Z_1$–$Z_2$ is separately purchased or synthesized and incorporated into the peptide as the last residue in the synthesis. The linear peptide is synthesized by solution synthesis or solid phase synthesis and cyclized in the same manner as when $Z_1$ and $Z_2$ are a covalent bond, as described more fully above. 2-aminosuberic acid and 1-(2-carboxyphenyl)-2(2-aminophenyl)ethane are representative of $Z_1$–$Z_2$ connected in an alkylene bridge.

Modification of the terminal amino group of the peptide is accomplished by alkylation or acetylation as is generally known in the art. These modifications may be carried out upon the amino acid prior to incorporation into the peptide, or upon the peptide after it has been synthesized and the terminal amino group liberated, but before the protecting groups have been removed.

Typically, acetylation is carried out upon the free amino group using the acyl halide, or anhydride, of the corresponding alkyl or aryl acid, in the presence of a tertiary amine. Mono-alkylation is carried out most conveniently by reductive alkylation of the amino group with an appropriate aliphatiC aldehyde or ketone in the presence of a mild reducing agent, such as lithium or sodium cyanoborohydride. Dialkylation may be carried by treating the amino group with an excess of an alkyl halide in the presence of a base.

Solution synthesis of peptides is accomplished using conventional methods used to form amide bonds. Typically, a protected Boc-amino acid which has a free carboxyl group is coupled to a protected amino acid which has a free amino group using a suitable carbodiimide coupling agent, such as N,N' dicyclohexyl carbodiimide (DCC), optionally in the presence of catalysts such as 1-hydroxybenzotriazole (HOBT) and dimethylamino pyridine (DMAP). Other methods, such as the formation of activated esters, anhydrides or acid halides, of the free carboxyl of a protected Boc-amino acid, and subsequent reaction with the free amine of a protected amino acid, optionally in the presence of a base, are also suitable. For example, a protected Boc-amino acid or peptide is treated in an anhydrous solvent, such as methylene chloride or tetrahydrofuran (THF), in the presence of a base, such as N-methyl morpholine, DMAP or a trialkylamine, with isobutyl chloroformate to form the "activated anhydride", which is subsequently reacted with the free amine of a second protected amino acid or peptide. The peptide formed by these methods may be deprotected selectively, using conventional techniques, at the amino or carboxy terminus and coupled to other peptides or amino acids using similar techniques.

The α-R' substituted derivatives of the amino acids of this invention, which includes derivatives of Arg, HArg, (Me$_2$) Arg, (Et$_2$)Arg, Ala, Gly, His, Abu, Tyr, (Alk)Tyr, Phe, (4'W) Phe, HPhe, Phg, Trp, His, Ser, (Alk)Ser, Thr, (Alk)Thr, Cys, (Alk)Cys, Pen, (Alk)Pen, Ala, Val, Nva, Met, Leu, Ile, Nle and Nal, are prepared by methods common to the chemical art. The R' substituent may be Alk, as hereinbefore defined, or benzyl. Representative methods for preparing these derivatives are disclosed in U.S. Pat. No. 4,687,758; Cheung et al., *Can. J. Chem.*, 55, 906 (1977); Freidinger et al., *J. Org. Chem.*, 48, 77, (1982); and Shuman et al., Peptides: *Proceedings of the 7th American Peptide Symposium*, Rich, D., Gross, E., Eds, Pierce Chemical Co., Rockford, Ill., 617 (1981), which are incorporated herein by reference. Typically, a solution of the Cbz- or Boc-amino acid in DMF/THF is condensed with an appropriate alkyl halide, such as methyl or ethyl iodide, in the presence of a base, such as sodium hydride or potassium hydride. Optionally, a crown ether, such as 18-crown-6 with potassium hydride, may be added to facilitate the reaction. Generally, in this process and those that follow, if the amino acid bears a functional group such as a hydroxyl, mercaptan, amino, guanidino, indolyl or imidazolyl group, these groups are protected as hereinbefore described. Thus, Boc-Tyr(Bzl) is treated with sodium hydride and methyl iodide in THF/DMF solution at 0° C. and stirred at room temperature for 24 hrs. to yield Boc-(α-Me)Tyr(Bzl).

Alternately, the free amine of the amino acid is reacted with an appropriate aldehyde, such as acetaldehyde or benzaldehyde, in the presence of a reducing agent, such as sodium cyanoborohydride, to effect mono-alkylation. This process is especially useful for preparing α-benzyl amino acids. α-Benzylated amino acids may also be used as intermediates to prepare α-methyl amino acids. For example, α-methyl arginine is prepared in three steps by 1.) reacting Arg(Tos) with benzaldehyde and sodium cyanoborohydride in a methanol solution to yield (α-Bzl) Arg(Tos); 2.) reducing the benzylated product with formaldehyde/formic acid solution to yield (α-Bzl, α-Me) Arg(Tos); and 3.) liberating the benzyl group by catalytic hydrogenation (5% Pd/C in glacial acetic acid/HCl) to yield MeArg(Tos).

α-R' substituted derivatives of amino acids may also be prepared by reduction of oxazolidinones prepared from the Fmoc- or Cbz-amino acids. Typically, an Fmoc- or Cbz-amino acid is heated with an appropriate aldehyde such as acetaldehyde or benzaldehyde, in the presence of toluenesulfonic acid, in toluene solution to produce a 2-substituted 5-oxo-oxazolidine. Reduction of this oxazolidinone with triethylsilane and TFA in chloroform solution affords the Cbz- or Fmoc-α substituted amino acid directly. It will be appreciated by those skilled in the art that when formaldehyde is used, the oxazolidinone is unsubstituted in the 2-position and α-methyl amino acids are produced.

Acid addition salts of the peptides are prepared in a standard manner in a suitable solvent from the parent compound and an excess of an acid, such as hydrochloric, hydrobromic, sulfuric, phosphoric, acetic, maleic, succinic or methanesulfonic. The acetate salt form is especially useful. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li+, Na+, K+, Ca++, Mg++ and NH$_4$+ are specific examples of cations present in pharmaceutically acceptable salts.

This invention provides an pharmaceutical composition which comprises a peptide according to formula (I) and a pharmaceutically acceptable carrier. Pharmaceutical compositions of the peptides prepared as hereinbefore described and other peptide or polypeptide derivatives of fibronectin, fibrinogen or Von Willebrand's factor, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these peptides may be encapsulated, tableted or prepared in a emulsion or syrup for oral administration.

Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the peptides of this invention may also be combined with excipients such as cocoa butter, glycerin, gelatin or polyethylene glycols and molded into a suppository.

This invention also provides a method of inhibiting platelet aggregation and clot formation in a mammal, especially a human, which comprises the internal administration of a peptide of formula (I) and a pharmaceutically acceptable carrier. Indications for such therapy include acute myocardial infarction (AMI), deep vein thrombosis, pulmonary embolism, dissecting anurysm, transient ischemia attack (TIA), stroke and other infarct-related disorders, and unstable angina. Chronic or acute states of hyperaggregability, such as disseminated intravascular coagulation (DIC), septicemia, surgical or infectious shock, postoperative and post-partum trauma, cardiopulmonary bypass surgery, incompatible blood transfusion, abruptio placenta, thrombotic thrombocytopenic purpura (TTP), snake venom and immune diseases, are likely to be responsive to such treatment. In addition, the peptides of this invention may be used in a method for the prevention of metastatic conditions.

The peptide is administered either orally or parenterally to the patient, in a manner such that the concentration of drug in the plasma is sufficient to inhibit platelet aggregation. The pharmaceutical composition containing the peptide is administered at a dose between about 0.2 to about 50 mg/kg in a manner consistent with the condition of the patient. For acute therapy, parenteral administration is preferred. For persistant states of hyperaggregability, an intravenous infusion of the peptide in 5% dextrose in water or normal saline is most effective, although an intramuscular bolus injection may be sufficient.

For chronic, but noncritical, states of platelet aggregability, oral administration of a capsule or tablet, or a bolus intramuscular injection is suitable. The peptide is administered one to four times daily at a level of about 0.4 to about 50 mg/kg. to achieve a total daily dose of about 0.4 to about 200 mg/kg/day.

This invention further provides a method for inhibiting the reocclusion of an artery or vein following fibrinolytic therapy, which comprises internal administration of a peptide of formula (I) and a fibrinolytic agent. It has been found that administration of an peptide in fibrinolytic therapy either prevents reocclusion completely or prolongs the time to reocclusion.

When used in the context of this invention the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants, thereof, which retain plasminogen activator activity, such as variants which have been chemically modified or in which one or more amino acids have been added, deleted or substituted or in which one or more or functional domains have been added, deleted or altered such as by combining the active site of one plasminogen activator with the fibrin binding domain of another plasminogen activator or fibrin binding molecule. Other illustrative variants include tPA molecules in which one or more glycosylation sites have been altered. Preferred among plasminogen activators are variants of tPA in which the primary amino acid sequence has been altered in the growth factor domain so as to increase the serum half-life of the plasminogen activator. tPA Growth factor variants are disclosed, e.g., by Robinson et al., EP-A 0 297 589 and Browne et al., EP-A 0 240 334 and in GB 8815135.2. Other variants include hybrid proteins, such as those disclosed in EP 0 028 489, EP 0 155 387 and EP 0 297 882, all of which are incorporated herein by reference. Anistreplase is a preferred hybrid protein for use in this invention. Fibrinolytic agents may be isolated from natural sources, but are commonly produced by traditional methods of genetic engineering.

Useful formulations of tPA, SK, UK and pUK are disclosed, for example, in EP-A 0 211 592 (U.S. Ser. No. 890,432), German Patent Application No. 3032606, EP-A 0 092 182 and U.S. Pat. No. 4,568,543, all of which are incorporated herein by reference. Typically the fibrinolytic agent may be formulated in an aqueous, buffered, isotonic solution, such as sodium or ammonium acetate or adipate buffered at pH 3.5 to 5.5. Additional excipients such as polyvinyl pyrrolidone, gelatin, hydroxy cellulose, acacia, polyethylene, glycol, mannitol and sodium chloride may also be added. Such a composition can be lyophilized.

The pharmaceutical composition may be formulated with both the peptide and fibrinolytic in the same container, but formulation in different containers is preferred. When both agents are provided in solution form they can be contained in an infusion/injection system for simultaneous administration or in a tandem arrangement.

Indications for such therapy include myocardial infarction, deep vein thrombosis, pulmonary embolism, stroke and other infarct-related disorders. The peptide is administered just prior to, at the same time as, or just after parenteral administration of tPA or other fibrinolytic agent. It may prove desirable to continue treatment with the peptide for a period of time well after reperfusion has been established to maximally inhibit post-therapy reocclusion. The effective dose of tPA, SK, UK or pUK may be from 0.5 to 5 mg/kg and the effective dose of the peptide may be from about 0.1 to 25 mg/kg.

For convenient administration of the inhibitor and the fibrinolytic agent at the same or different times, a kit is prepared, comprising, in a single container, such as a box, carton or other container, individual bottles, bags, vials or other containers each having an effective amount of the inhibitor for parenteral administration, as described above, and an effective amount of tPA, or other fibrinolytic agent, for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the fibrinolytic and the peptide may be packaged separately, as in two containers, or lyophilized together as a powder and provided in a single container.

When both agents are provided in solution form, they can be contained in an infusion/injection system for simultaneous administration or in a tandem arrangement. For example, the platelet aggregation inhibitor may be in an i.v. injectable form, or infusion bag linked in series, via tubing, to the fibrinolytic agent in a second infusion bag. Using such a system, a patient can receive an initial bolus-type injection or infusion, of the peptide inhibitor followed by an infusion of the fibrinolytic agent.

The pharmacological activity of the peptides was assessed by the following tests:

In Vivo Inhibition of Platelet Aggregation

In vivo inhibition of thrombus formation is demonstrated by recording the systemic and hemodynamic effects of infusion of the peptides into anesthetized dogs according to the methods described in Aiken et al., *Prostaglandins*, 19, 629–43 (1980).

Inhibition of Platelet Aggregation

Blood was collected (citrated to prevent coagulation) from, naive, adult mongrel dogs. Platelet rich plasma, PRP, was prepared by centrifugation at 150×g for 10 min at room temperature. Washed platelets were prepared by centrifuging PRP at 800×g for 10 min. The cell pellet thus obtained was washed twice in Tyrode's buffer (pH 6.5) without $Ca^{++}$ and resuspended in Tyrode's buffer (pH 7.4) containing 1.8 mM $Ca^{++}$ at $3\times10^5$ cells/ml. Peptides were added 3 min prior to the agonist in all assays of platelet aggregation. Final agonist concentrations were 0.1 unit/ml thrombin and 2 mM ADP (Sigma). Aggregation was monitored in a Chrono-Log Lumi-Aggregometer. Light transmittance 5 min after addition of the agonist was used to calculate percent aggregation according to the formula % aggregation=[(90-CR)÷(90-10)]×100, where CR is the chart reading, 90 is the baseline, and 10 is the PRP blank reading. $IC_{50}$'s were determined by plotting [% inhibition of aggregation] vs. [concentration of peptide]. Peptides were assayed at 200 mM and diluted sequentially by a factor of 2 to establish a suitable dose response curve.

To assess the stability of the peptide to plasma proteases, the peptides were incubated for 3 hrs. (rather than 3 min) in the PRP prior to addition of the agonist.

The compounds of Examples 1–21 showed an $IC_{50}$ for the aggregation of dog platelets stimulated by ADP of between about 0.1 and 50 µM. The compounds of Examples 22, 24, 25 and 28 have an $IC_{50}$ of greater than 200 µM. Preferred compounds have an $IC_{50}$ of less than 10 µM.

The examples which follow are intended to in no way limit the scope of this invention, but are provided to illustrate how to make and use the compounds of this invention. Many other embodiments will be readily apparent and available to those skilled in the art.

EXAMPLES

In the examples which follow all temperatures are in degrees centigrade. Amino acid analysis was performed upon a Dionex autoion 100. Analysis for peptide content is based upon amino acid analysis. Mass spectra were performed upon a VG Zab mass spectrometer using fast atom bombardment. EM silica gel thin layer (0.25 mm) plates were used for thin layer chromatography. ODS refers to an octadecylsilyl silica gel chromatographic support. The abbreviations used to represent the eluent composition are n-BuOH: n-butanol, HOAc: acetic acid, $H_2O$: water, EtOAc: ethyl acetate, i-ProH: isopropanol, P: pyridine and CA: chloroacetic acid. HPLC was performed upon a Beckman 344 gradient chromatography system with a CRIB recording integrator in either an isocratic or continuous gradient mode. Solid phase peptide synthesis was performed using an automated Beckman 990 synthesizer. Where indicated, the purity of the peptide is based upon integration of the HPLC chromatogram. MeArg was prepared by the method disclosed by Ali et al., in U.S. Pat. No. 4,687,758 (1987).

Example 1

Preparation of cyclo (S,S)-(2-mercapto)benzoyl-arginyl-glycyl-aspartyl-cysteineamide[cyclo-(S,S)-Mba-Arg-Gly-Asp-Cys-NH₂]

General procedure for solid phase peptide synthesis on benzhydylamine resin

Peptide amides were synthesized by solid phase peptide synthesis using benzhydrylamine resin as the support. Protected amino acids were added sequentially starting from the carboxyl terminus until the desired sequence was obtained. The t-butyloxycarbonyl (Boc) group was used for protection of the alphayamino group. Side chain functional groups were protected as follows:; arginine and histidine, tosyl (Tos); cysteine and 3-phenylcysteine, p-methylbenzyl (MBzl) or ethylthio (SEt); serine and threonine, benzyl ether (Bzl); lysine, p-chlorocarbobenzoxy (ClZ); glutamic acid and aspartic acid, benzyl ester (OBzl) or cyclohexyl ester (O-cHex); tyrosine, p-bromocarbobenzoxy (BrZ). Removal of the Boc group was accomplished by treatment with 50% trifluoroacetic acid (TFA) in methylene chloride. Neutralization of the amine-TFA salt was accomplished by treatment with 7% diisopropylethylamine (DIEA) in methylene chloride. Amino acids were coupled to the growing peptide using 3 equivalents of Boc-amino acid and 3 equivalents of 1-hydroxybenzotriazole (HOBt) in DMF and 3 equivalents of dicyclohexylcarbodiimide (DCC) in methylene chloride. Completeness of coupling was checked by ninhydrin test and couplings were repeated as necessary. The general protocol is given below.

| | | |
|---|---|---|
| 1. Wash with methylene chloride | | 1 × 1 min |
| 2. Wash with 50% TFA | | 1 × 1 min |
| 3. Deblock with 50% TFA | | 1 × 20 min |
| 4. Wash with methylene chloride | | 6 × 1 min |
| 5. Neutralize with 7% DIEA | | 3 × 2 min |
| 6. Wash with methylene chloride | | 4 × 1 min |
| 7. Wash with dimethylformamide | | 2 × 1 min |
| 8. Boc-AA + HOBT in DMF do not drain | | |
| 9. DCC in methylene chloride | | 2 h |
| 10. Wash with dimethylformamide | | 2 × 1 min |
| 11. Wash with methylene chloride | | 3 × 1 min |

For attachment of the first (C-terminal) residue to the BHA resin, the synthesis was begun at step 5. For all subsequent amino acids, the synthesis was begun at step 1.

a) 2-S-ethylmercaptobenzoic acid

To argon purged hexane (50 mL), ethanethiol (3.7 mL, 50 mmol) and sulfuryl chloride (4.0 mL, 50 mmol) were added and the solution stirred for 30 min. Toluene (100 mL) was added followed immediately by 2-mercaptobenzoic acid (7.71 g, 50 mmol). The reaction mixture was stirred at room temperature for 3 h and the solid product precipitated out.

The solid was filtered, dried and chromatographed (silica gel, ethyl acetate) to yield the titled compound as tan solid (3.8 g, 36%).

b) cyclo-(S,S)-Mba-Arg-Gly-Asp-Cys-$NH_2$

The protected peptide-resin intermediate, Mba(SEt)-Arg (Tos)-Gly-Asp(O-Bzl)-Cys(4-MBzl)-MBHA, was synthesized by the solid-phase method on 4-methylbenzhydrylamine resin, using an automated Beckman 990 synthesizer on 1.0 mmol scale. All of the amino acids were protected as t-butyloxycarbonyl on the amino group, and were coupled sequentially using N,N-dicyclohexylcarbodiimide/1-hydroxybenzotriazole (DCC/HOBt) in the manner set forth by Ail et al. in *J. Med. Chem.*, 30, 2291 (1987) and *J. Med. Chem.* 29, 984 (1986). After coupling of the last amino acid, the peptide was cleaved from the resin with deprotection of the side chain protecting groups using anhydrous HF (20 mL) in the presence of anisole (2.0 mL) at 0° C. for 30 min. After the evaporation of HF in vacuo, the residue was washed with anhydrous ether, the crude peptide was extracted with 0.2M acetic acid, and the extract was diluted to 2 L with deionized water. The pH of the aqueous solution was adjusted to 8–9 with conc. ammonium hydroxide. Nitrogen was bubbled through the solution to remove the ethyl mercaptan produced. The cyclization process took place within 24–48 hr. The reaction solution was lyophilized to yield a solid (320 mg). Chromatography (medium pressure reversed-phase column, 10% acetonitrile/$H_2O$ -0.1% TFA) provided a partially purified product. Further purification using Sephadex® G-25 gel filtration (0.2M acetic acid) afforded the titled compound. MS(FAB) $[M+H]^+$ 583; TLC $R_f$ 0.22 (n-BuOH:HOAc:$H_2$O:EtOAc 1:1:1:1), $R_f$ 0.48 (B:W:I:C, 65:20:15:3); HPLC k' 2.2 (Vydac 218 TP ODS column, 12% acetonitrile/$H_2$O-0.1% TFA, UV detection at 220 nm), k' 3.6 (Vydac 218 TP ODS column, gradient, A:acetonitrile, B:$H_2$O-0.1% TFA; 0–50% A during 10 min, UV detection at 220 nm); Peptide content 45%; Amino Acid Analysis: Asp (0.94), Gly(1.00), Arg(0.42), Cys(0.53).

Example 2

Preparation of $N^\alpha$-acetyl-cyclo(S,S)-cysteinyl-arginyl-glycyl-aspartyl-(2-mercapto)phenylamide[cyclo-(S,S)-Ac-Cys-Arg-Gly-Asp-Man]

a) 2-(4-methylbenzyl)thioaniline(Man-4-MBzl)

To a solution of 2-thioaniline (5.0 mL, 42 mmol) in ethanol (50 mL), triethylamine (5.9 mL, 423 mmol) was added under argon. α-Bromo-p-xylene (7.78 g, 42 mmol) in ethanol (50 mL) was then added dropwise. The reaction mixture was stirred for 1 h, concentrated in vacuo to a small volume, diluted with anhydrous ether and filtered to remove triethyl amine hydrobromide. The filtrate was concentrated to dryness to give a yellow oil (5 g, 52%). Chromatography (silica gel, 20% ethyl acetate/hexane) yielded the titled compound as yellow oil (4.26 g).

b) Fmoc-Asp(O-t-BU)-Man(4-MBzl)

Fmoc-Asp(O-t-Bu) (5.0 g, 122 mmol) was dissolved in THF (50 mL), and N-methylmorpholine (1.3 mL, 118 mmol) was added, and the solution was cooled under argon in an ethanol/ice bath for 10 min. Isobutyl chloroformate (1.6 mL, 123 mmol) was added, the reaction stirred for 5 min, followed by the addition of a solution of Man(4-MBzl) (2.8 g, 122 mmol) in THF (50 mL). The cooled reaction mixture was stirred for 40 min and at room temperature for 4 h. The precipitated amine salt was filtered and the filtrate was evaporated to an oily material. The oil was dissolved in ethyl acetate (100 mL), washed with 1M HCl (2×50 mL), saturated salt solution (1×50 mL), 10% sodium carbonate solution (1×50 mL) and saturated salt solution (1×50 mL). It was then dried (anhydrous $Na_2SO_4$) and concentrated to an orange oil. Crystallization from methanol yielded the desired compound as a white solid (3.93 g, 26%). mp 129°–130° C. $H_2O$ c) Fmoc-Asp-Man(4-MBzl)

A mixture of Fmoc-Asp(O-tBu)-Man(4-MBzl) (3.5 g) and 50% TFA in methylene chloride (50 mL) was stirred at room temperature for 45 min. The solvent was evaporated and the product was precipitated by the addition of ether. The solid was collected and air dried to yield a white solid (2.23 g, 70%). mp 155°–156° C.

d) Fmoc-Asp(O-Bzl-resin)-Man(4-MBzl)

To a swelled and washed hydroxymethyl resin (1.0 g, 1-mmol, $CH_2Cl_2$) was added a solution of Fmoc-Asp-Man (4-MBzl) (1.42 g, 2.5 mmol) and DCC (10 mL, 0.3M in $CH_2Cl_2$) in dioxane (25 mL). The reaction was stirred for 18 h and washed sequentially with $CH_2Cl_2$, 1:1 mixture of $CH_2Cl_2$:EtOH and $CH_2Cl_2$. The unreacted hydroxymethyl resin was capped using benzoyl chloride (0.5 mL) in $CH_2Cl_2$ for 30 min. The resin was washed sequentially as above and dried to yield the resin-bound peptide (2.16 g).

e) $N^\alpha$-acetyl-cyclo(S,S)-Cys-Arg-Gly-Asp-Man

The protected peptide-resin intermediate, Na-Ac-Cys (SEt)-Arg(Tos)-Gly-Asp(O-Bzl-resin)-Man(4-MBzl), was prepared from Asp(O-Bzl-resin)-Man(4-MBzl) using the method of Example 1(b), by sequentially coupling Boc-Gly, Boc-Arg(Tos) and Boc-Cys(SEt). After coupling of the last amino acid, the terminal Boc group was removed with TFA, and the peptide was acetylated using a mixture of acetic anhydride (10 eq.) and diisopropylethylamine (10 eq.) in dimethylformamide. The peptide was cleaved from the resin, cyclized and isolated as in Example 1(b), to provide the crude peptide (310 mg). Chromatography (medium pressure ODS reversed-phase column, 10% acetonitrile:$H_2$O-0.2% TFA) affords the titled peptide (24 mg). MS(FAB) $[M+H]^+$ 597.2; TLC $R_f$ 0.57 (n-BuOH:HOAc:$H_2$O:EtOAc 1:1:1:1), $R_f$ 0.23, (n-BuOH:$H_2$O:i-ProH:CA 65:20:15:3); HPLC k'=4.9 (Vydac 218 Tp ODS column, 10% acetonitrile/$H_2$O-0.1% TFA, UV detection at 220 nm), k' 4.5 (Vydac 218 Tp ODS column, gradient, A:acetonitrile, B:$H_2$O-0.1% TFA, 0–50% A during 15 min, UV detection at 220 nm); Peptide content 44.6%; Amino Acid Analysis: Asp(1.00), Gly(1.03), Arg (0.94), Cys(0.5).

Example 3

Preparation of cyclo(S,S)-(2-mercapto)benzoyl-($N^\alpha$-methyl)arginyl-glycyl-aspartyl-(2-mercapto)phenylamide [cyclo-(S,S)-Mba-MeArg-Gly-Asp-Man]

The protected peptide-resin intermediate, Mba(SEt)-MeArg(Tos)-Gly-Asp(O-Bzl-resin)-Man(4-MBzl), was prepared, cleaved and cyclized in the same manner as Example 2 on 1.0 mmol scale. After the cyclization was completed, the aqueous solution was passed through a column of Amberlite® XAD-2 (1:1 acetonitrile:$H_2$O-0.1% TFA), concentrated and lyophilized to afford a crude peptide (100 mg). Chromatography (medium pressure ODS reversed-phase column, 30% acetonitrile/$H_2$O-0.1% TFA) yielded the titled compound (14 mg). MS(FAB) m/e $[M+H]^+$ 602.3; TLC: $R_f$ 0.63, (n-BuOH:HOAc:$H_2$O:EtOAc 1:1:1:1); HPLC k' 3.2 (Vydac 218 TP ODS column, 20% acetonitrile/ $H_2$O-0.1% TFA, detection at 220 nm), k' 2.3, (Vydac 218 TP ODS column, gradient, A:acetonitrile, B:$H_2$O-0.1% TFA, 20–50% A during 10 min, detection at 220 nm); Peptide content 79% Amino Acid; Analysis: Asp(1.00), Gly(1.21)

Example 4

Preparation of cyclo-(S,S)-(2-mercapto)benzoyl-(N$^\alpha$-methyl)arginyl-glycyl-aspartyl-(2-mercapto)phenylamide [cyclo(S,S)-Mba-MeArg-Gly-Asp-Man]

a) Boc-Asp(O-cHex)-Man(4-MBzl)

To a cold solution of Boc-Asp(O-cHex), (31.5 g, 100 mmol) in THF (500 mL) and N-methylmorpholine (13.1 g, 120 mmol), isobutylchloroformate (15.6 mL, 1.2 mmol) was added dropwise. The reaction mixture was stirred for a few minutes and a solution of Man(4-MBzl) (22.0 g, 96 mmol) in THF (500 mL) was added. The reaction mixture was allowed to warm to room temperature and stirred for 18 h. Upon completion of the reaction, the reaction mixture was filtered and the filtrate was concentrated to dryness. The residue was dissolved in ethyl acetate (500 mL), and washed successively with 5% aqueous citric acid (3×150 mL), water (1×400 mL), 10% aqueous NaHCO$_3$ (1×400 mL), water (1×400 mL) and saturated salt solution (1×300 mL). The solution was dried (anhydrous K$_2$CO$_3$), filtered and concentrated to yield the titled compound (53 g).

b) Asp(O-cHex)-Man(4-MBzl)

Boc-Asp(O-cHex)-Man(4-MBzl) (52 g) was treated with 50% TFA/methylene chloride (400 mL) for 45 min at room temperature. The solvent was evaporated and chased several times with methylene chloride to eliminate traces of TFA. The product precipitated as its TFA salt upon addition of ether. The solid was collected and air dried to yield a white solid (46.7 g, 88%).

c) Boc-Gly-Asp(O-cHex)-Man(4-MBzl)

To a cold solution of Asp(O-cHex)-Man(4-MBzl) (46.7 g, 86.4 mmol) in DMF (100 mL) diisopropylethylamine (15 mL, 86.1 mmol) was added. N-Hydroxybezotriazole (14.0 g, 104 mmol) was added followed by Boc-Gly (16.6 g, 94.8 mmol). The reaction mixture was stirred in the cold for a few minutes, and N-ethyl-N'-(dimethylaminopropyl) carbodiimide (18.2 g, 94.9 mmol) was added. The reaction mixture was allowed to warm to room temperature and stirred for 18 h. The reaction mixture was concentrated to a small volume and poured into 1.5 L of aqueous 10% K$_2$CO$_3$. The precipitated product was collected by filtration and was washed with water to a neutral pH to afford the titled compound (50.6 g).

d) Gly-Asp(O-cHex)-Man(4-MBzl)

The compound of Example 4(c) (11.7 g, 20 mmol) was treated with 50% TFA/CH$_2$Cl$_2$ (80 mL) as described in Example 4(b) to give 12.4 g of the titled compound.

e) Boc-Me-Arg(Tos)-Gly-Asp(O-cHex)-Man(4-MBzl)

To an ice cold solution of the compound of Example 4(d) (12.4 g, 20 mmol) in DMF (20 mL), DIEA (3.6 mL, 20 mmol) was added. HOBt (3.4 g, 02 mmol) was added followed by Boc-N-MeArg(Tos) (10.1 g, 22 mmol). The reaction mixture was stirred for several min and EDC (4.4 g, 22 mmol) was added portionwise. The reaction mixture was allowed to warm to room temperature and stirred for 18 h. The reaction was concentrated to a small volume and poured into 10% aqueous K$_2$CO$_3$. The resulting solid was collected by filtration and washed with water to neutral pH to provide the titled compound (20.4 g).

f) MeArg(Tos)-Gly-Asp(O-cHex)-Man(4-MBzl)

The compound of Example 4(e) (17.7 g, 19.5 mmol) was treated with 50% TFA/CH$_2$Cl$_2$ (80 mL) as in Example 4(b) to provide the TFA salt of the titled compound.

g) Mba(SEt)-MeArg(Tos)-Gly-Asp(O-cHex)-Man(4-MBzl)

To a cold solution of the compound of Example 4(f) (20 mmol) in DMF (20 mL) was added DIEA (3.5 mL, 22 mmol) dropwise. Mba(SEt) (4.6 g, 22 mmol), EDC (4.2 g, 22 mmol) were added successively, followed by 4-N,N-dimethylaminopyridine (DMAP) (2.9 g, 24 mmol). The reaction mixture was allowed to warm to room temperature and stirring was continued for another 24 h. Another portion of Mba(SEt) (4.6 g, 22 mmol), DMAP (2.9 g,24 mmol) and EDC (4.2 g, 22 mmol) were added and stirring was continued for another 24 h to obtain complete reaction. The reaction mixture was concentrated, the residue was dissolved in CH$_2$Cl$_2$, the solution was washed successively with water, 5% aq. citric acid, water and saturated salt solution. The organic extracts was dried (anhydrous Na$_2$SO$_4$), filtered and concentrated to a solid residue (19.1 g). Chromatography (silica gel, 10% MeOH/CH$_2$Cl$_2$) affords the titled compound (9.0 g).

h) cyclo-(S,S)-Mba-MeArg-Gly-Asp-Man

The protected linear peptide of Example 4(g) (8.5 g, 8.5 mmol), was treated with anhydrous HF (90 mL) and anisole (8.5 mL) at 0° C. for 1 hr. The HF was removed at 0° C. under vacuum, and the residue was washed with ether to yield a tan solid (5.0 g). The solid was dissolved in water (16 L), and the pH was adjusted to 8.0 using ammonium hydroxide. Nitrogen was bubbled through the solution to remove the ethyl mercaptan generated. After 7 days, the aqueous solution was passed through a column of Amberlite® XAD-2 (50% methanol/H$_2$O) to give 3.0 g after lyophilization. Further purification by flash chromatography (medium pressure ODS reversed-phase column, 21% acetonitrile/H$_2$O-0.1% TFA) gave 2.3 g of partially purified material. Final purification using Sephadex® G-15 gel filtration (0.2M acetic acid) provided the titled compound (1.0 g).

Example 5

Preparation of cyclo(S,S)-(2-mercapto)benzoyl-(N$^\alpha$-methyl)arginyl-glycyl-aspartyl-(3-phenyl)cysteineamide [cyclo-(S,S)-Mba-MeArg-Gly-Asp-Pcs]

Diasteromeric 3-phenylcysteine is prepared according to the method described by Nagai et al., in Peptide Chemistry, edited by, M. Ueki, Proceedings of the 26th Symposium on Peptide Chemistry, Tokyo, Oct. 24–26, 1988, Protein Research Foundation, Minoh-shi, Osaka, pages 247–52. Using standard methods, this material is converted to S-(4-methoxyphenyl)-N-(t-butoxycarbonyl)-3-phenylcysteine. The protected peptide-resin intermediate, Mba(SEt)-Arg (Tos)-Gly-Asp(O-Bzl)-Pcs(4-MBzl)-MBHA, is synthesized by the solid-phase method on 4-methylbenzhydrylamine resin. All of the amino acids are protected by t-butyloxycarbonyl on the amino group, and are coupled sequentially using N,N-dicyclohexylcarbodiimide/1-hydroxybenzotriazole (DCC/HOBt) as set forth in Example 1. After coupling of the last amino acid, the peptide is cleaved from the resin with deprotection of the side chain protecting groups using anhydrous HF (20 mL) in the presence of anisole (2.0 mL) at 0° C. for 30 min. After the evaporation of HF in vacuo, the residue is washed with anhydrous ether, the crude peptide is extracted with 0.2M acetic acid, and the extract is diluted to 2 L with deionized water. The pH of the aqueous solution is adjusted to 7–8 with concentrated ammonium hydroxide and Nitrogen is bubbled through the solution. After 24–48 hr. The reaction solution is lyophilized to yield a crude product. Chromatography (medium pressure reversed-phase column, acetonitrile/H$_2$O-0.1% TFA) provides the titled product.

Example 6

Preparation of cyclo-(S,S)-Mba-Sar-Arg-Gly-Asp-Man a) Boc-Asp(Oc-Hex)-Man(4-MBzl)

To a cold solution of Boc-Asp(O-cHex) (31.5 g, 100 mmol) and N-methylmorpholine (13.1 g, 120 mmol) in THF (500 mL), isobutylchloroformate (15.6 mL, 1.2 mmol) was added dropwise. The reaction mixture was stirred for a few minutes, then a solution of Man(4-MBzl) (22.0 g, 96 mmol) in THF (500 mL) was added. The reaction mixture was allowed to warm to room temperature and stirred for 18 h. Upon completion of the reaction (monitored by TLC), the amine sand the filtered off and the filtrate was concentrated to dryness. The residue was dissolved in ethyl acetate (500 mL) and washed successively with 5% aqueous citric acid (3×150 mL), water (1×400 mL), aqueous $NaHCO_3$ (1×300 mL), water (1×400 mL) and saturated salt solution (1×30 mL). The organic solvent was dried (anhydrous $K_2CO_3$), filtered and concentrated to yield the title product (53 g).

b) Asp (O-cHex)-Man(4-MBzl)

Boc-Asp(O-cHex)-Man(4-MBzl), (1) (52 g) was treated with 50% TFA solution in methylene chloride (400 mL) for 45 min at room temperature. The solvent was removed and the residue was azeotroped several times from methylene chloride to eliminate traces of TFA, and the product was precipitated by the addition of ether. The solid was collected and air dried to yield a white solid (46.7 g, 88%).

c) Boc-Gly-Asp(O-cHex)-Man(4-MBzl)

To a cold solution of the compound of Example 6b (46.7 g, 86.4 mmol) in DMF (100 mL), DIEA (15 mL, 86.1 mmol) was added to bring the pH to neutrality. HOBt (14.0 g, 104 mmol) was added followed by Boc-Gly (16.6 g, 94.8 mmol). The reaction was stirred in the cold for a few min, then EDC (18.2 g, 94.9 mmol) was added portionwise. The reaction mixture was allowed to warm to room temperature and stirred for 18 h. The reaction mixture was concentrated to a small volume and poured into 1.5 L of aqueous 10% $K_2CO_3$. The precipitated product was collected by filtration and washed with water to yield the titled compound (50.6 g).

d) Gly-Asp(O-cHex)-Man(4-MBzl)

The compound of Example 6c (2.92 g, 5 mmol) was treated with 50% TFA (80 mL) according to the procedure of Example 6b to yield the titled compound (2.93 g , 98%).

e) Boc-Arg(Tos)-Gly-Asp(O-cHex)-Man(4-MBzl)

To an ice cold solution of the compound of Example 6d (1.4 g, 2.3 mmol) in DMF (4 mL), DIEA (410 μL, 2.3 mmol) was added to bring the pH to neutrality. HOBt (380 mg, 2.76 mmol) was added followed by Boc-Arg(Tos) (1.2 g, 1.32 mmol). The reaction mixture was stirred for a few min, then EDC (493 mg, 1.32 mmol) was added. The reaction mixture was allowed to warm to room temperature and stirred for 18 h. The reaction mixture was concentrated to dryness, and the residue was dissolved in ethyl acetate and washed successively with water (1×), 10% $K_2CO_3$ (2×), water (1×) and brine (1×). The ethyl acetate extract was dried (anhydrous $K_2CO_3$) filtered and concentrated to yield the titled compound (1.91 g).

f) Arg(Tos)-Gly-Asp(O-cHex)-Man(4-MBzl)

The compound of Example 6e (1.9 g, 2.1 mmol) was treated with 50% TFA (10 mL) according to the procedure of Example 6b to yield the titled compound (1.59 g).

g) Boc-Sar-Arg(Tos)-Gly-Asp(O-cHex)-Man(4-MBzl)

To an ice cold solution of the compound of Example 6f (0.8 g, 2.3 mmol) in DMF (2 mL), DIEA (153 μL) was added to bring the pH to neutrality. HOBt (143 mg, 2.76 mmol) was added followed by Boc-Sar (183 mg, 2.53 mmol). The reaction mixture was stirred for a few min, then EDC (186 mg, 2.53 mmol) was added portionwise. The reaction mixture was allowed to warm to room temperature and stirred for 18 h. It was then concentrated to dryness, and the residue was dissolved in ethyl acetate and washed successively with water (1×), 10% $K_2CO_3$ (2×), water (1×) and brine (1×). The ethyl acetate extract was dried (anhydrous $K_2CO_3$), filtered and concentrated to yield the titled compound (0.78 g).

h) Sar-Arg(Tos)-Gly-Asp(O-cHex)-Man(4-MBzl)

The compound of Example 6g (780 m g, 0.8 mmol) was treated with 50% TFA (5 mL) according to the procedure of Example 6b to yield the titled compound (500 mg).

i) Mba(SEt)-Sar-Arg(Tos)-Gly-Asp(O-cHex)-Man(4-MBzl)

To an ice cold solution of the compound of Example 6h (0.85 g, 0.5 mmol) in DMF (2 mL), DIEA (89 μL) was added to bring the pH to neutrality. HOBt (248 mg, 1.8 mmol) was added followed by Mba(SEt) (394 mg, 0.55 mmol). The reaction mixture was stirred for a few min, then EDC (353 mg, .55 mmol) was added portionwise. The reaction mixture was allowed to warm to room temperature and stirred for 18 h. It was then concentrated to dryness and the residue was dissolved in ethyl acetate and washed successively with water (1×), 10% $K_2CO_3$ (2×), water (1×), 5% citric acid (2×), water (3×) and brine (1×). The ethyl acetate extract was dried (anhydrous $Na_2SO_4$), filtered and concentrated to yield the titled compound (0.45 g).

j) cyclo(S,S)-Mba-Sar-Arg-Gly-Asp-Man

The protected linear peptide of Example 6i (423 mg), was treated with anhydrous HF (10 mL) in the presence of anisole (1 mL) at 0° C. for 1 h. The HF was removed at 0° C. under vacuum, and the residue was triturated with ether. The solid was dried in vacuo to yield the crude cyclized peptide (235 mg). It was purified by gel filtration (Sephadex® G-15, 1% acetic acid/water) The appropriate fractions were pooled and lyophilized to yield the semipurified titled compound (65 mg). An aliquot of the semipurified peptide (18 mg) was purified by preparative HPLC (5μ Altex Ultrasphere® ODS, 10 mm×25 cm, 20% acetonitrile/water-0.1% trifluoroacetic acid, UV detection at 220 nm to yield the purified title compound (6.0 mg). MS (FAB) m/e 659.1 [M+H]$^+$; HPLC k' 6.6 (5μ Altex Ultrasphere® ODS, 4.5 mm×25 cm, gradient, A:acetonitrile B:water-0.1% trifluoroacetic acid, 10%–50% acetonitrile in 20 min, UV detection at 220 nm), k' 6.9 (Altex Ultrasphere® ODS, 20% acetonitrile/water-0.1% trifluoroacetic acid, UV detection at 220 nm), Amino Acid Analysis: Asp (1.00), Gly (1.03), Arg (1.11).

Example 7

Preparation of cyclo-(S,S)-Mba-Sar-MeArg-Gly-Asp-Man a) Boc-MeArg(Tos)-Gly-Asp(O-cHex)-Man(4-MBzl)

To an ice cold solution of the compound of Example 6d (0.6 g, 1.0 mmol) in DMF (42 mL), DIEA (130 μL, 2.2 mmol) was added to bring the pH to neutrality. HOBt (165 mg, 1.2 mmol) was added followed by Boc-MeArg(Tos) (0.5 g, 1.1 mmol). The reaction mixture was stirred for a few min, then EDC (210 mg, 1.2 mmol) was added. The reaction mixture was allowed to warm to room temperature and stirred for 18 h. It was concentrated to dryness and the residue was dissolved in ethyl acetate and washed successively with water (1×), 10% $K_2CO_3$(2×), water (1×), 5% citric acid (2×) and brine (1×). The ethyl acetate extract was dried (anhydrous $Na_2SO_4$), filtered and concentrated to yield the titled compound (780 mg, 86%).

b) MeArg(Tos)-Gly-Asp(O-cHex)-Man(4-MBzl)

The compound of Example 7a (789 mg, 0.86 mmol) was treated with 50% TFA (4 mL) according to the procedure of Example 6b to yield the titled compound.

c) Boc-Sar-MeArg(Tos)-Gly-Asp(O-cHex)-Man(4-MBzl)

To an ice cold solution of the compound of Example 7b (0.8 g, 0.86 mmol) in DMF (2 mL), DIEA (153 μL) was added to bring the pH to neutrality. HOBt (143 mg, 1.03 mmol) was added, followed by Boc-Sar (183 mg, 0.95 mmol). The reaction mixture was stirred for a few min and EDC (186 mg, 0.95 mmol) was added. The reaction mixture was allowed to warm to room temperature and stirred for 18 h. The reaction mixture was concentrated to dryness, and the residue was dissolved in ethyl acetate and washed successively with water (1×), 10% $K_2CO_3$ (2×), water (1×), 1N HCl (1×), water (3×) and brine (1×). The ethyl acetate extract was dried (anhydrous $Na_2SO_4$), filtered and concentrated to yield the titled compound (0.65 g).

d) Sar-MeArg(Tos)-Gly-Asp(O-cHex)-Man(4-MBzl)

The compound of Example 7c (650 mg, 0.8 mmol) was treated with 50% TFA (5mL) according to the procedure of Example 6b to yield the titled compound (510 mg).

e) Mba(SEt)-Sar-MeArg(Tos)-Gly-Asp(O-cHex)-Man(4-MBzl)

To an ice cold solution of the compound of Example 6d (0.5 g, 0.5 mmol) in DMF (2 mL), DIEA (120 mL, 0.6 mmol) was added to bring the pH to neutrality. HOBt (150 mg, 0.55 mmol) was added, followed by Mba(SEt) (394 mg, 0.55 mmol). The reaction mixture was stirred for a few min, then EDC (260 mg, 0.55 mmol) was added portionwise. The reaction mixture was allowed to warm to room temperature, stirred for 18 h and concentrated to dryness. The residue was dissolved in ethyl acetate and washed successively with water (1×), 10% $K_2CO_3$ (2×), water (1×), 5% citric acid (2×), water (3×) and brine (1×). The ethyl acetate extract was dried (anhydrous $Na_2SO_4$), filtered and concentrated to yield the titled compound (0.46 g).

f) cyclo-(S,S)-Mba-Sar-MeArg-Gly-Asp-Man

The protected linear peptide of Example 7d (450 mg) was treated with anhydrous HF (10 mL) in the presence of anisole (1 mL) at 0° C. for 1 h. The HF was removed at 0° C. under vacuum, and the residue was triturated with ether. The solid was dried in vacuo to yield the crude cyclized peptide (268 mg). It was purified by gel filtration (Sephadex® G-15, 1% acetic acid/water). The appropriate fractions were pooled and lyophilized to yield the semipurified peptide. An aliquot of the semipurified peptide (65 mg) was further purified by HPLC (5μ Altex Ultrasphere® ODS, 10 mm×25 cm, 20% acetonitrile/water-0.1% trifluoroacetic acid, UV detection at 220 nm) to yield the titled compound (6.0 mg). MS (FAB) m/e 673.2 [M+H]$^+$; TLC $R_f$ 0.68 (n-BuOH:HOAc:H2O:EtOAc 1:1:1:1), $R_f$ 0.74 (n-BuOH:HOAc:H2O:pyridine 15:5:10:10); HPLC k' 11.8 (5μ Altex Ultrasphere® ODS, gradient, A:acetonitrile B:water-0.1% trifluoroacetic acid, 10%–50% acetonitrile in 20 min, UV detection at 220 nm), k' 8.6 (Altex Ultrasphere® ODS, 20% acetonitrile/water-0.1% trifluoroacetic acid, UV detection at 220 nm); Amino Acid Analysis: Asp (1.04), Gly (1.00).

Example 8

Preparation of cyclo-(S,S)-Mba-Arg-Gly-Asp-Man a) Mba(SEt)-Arg(Tos)-Gly-Asp(O-cHex)-Man(4-MBzl)

To an ice cold solution of the compound of Example 6f (0.80 g, 0.88 mmol) in DMF (2 mL), DIEA (153 μL) was added to bring the pH to neutrality. Mba(SEt) (380 mg, 0.97 mmol) was added, the reaction mixture was stirred for a few min, and EDC (340 mg, 0.97 mmol) was added, followed by 4-dimethylaminopyridine (215 mg). The reaction mixture was allowed to warm to room temperature, stirred for 18 h, and concentrated to dryness. The residue was taken into ethyl acetate and washed successively with water (1×), 10% $K_2CO_3$ (2×), water (1×), 5% citric acid (2×), water (3×) and brine (1×). The ethyl acetate extract was dried (anhydrous $Na_2SO_4$), filtered and concentrated to yield the titled compound (0.41 g).

b) cyclo-(S,S)-Mba-Arg-Gly-Asp-Man

The protected linear peptide of Example 8b (223 mg) was treated with anhydrous HF (10 mL) in the presence of anisole (1 mL) at 0° C. for 1 h. The HF was removed at 0° C. under vacuum, and the residue was triturated with ether. The solid was dried in vacuo to yield the crude cyclized peptide (92 mg). An aliquot (20 mg) was purified by HPLC (5μ Altex Ultrasphere® ODS, 10 mm×25 cm, 18% acetonitrile/water-0.1% trifluoroacetic acid, UV detection at 220 nm) to yield the purified titled compound (5.0 mg). MS (FAB) m/e 588 [M+H]$^+$; TLC $R_f$ 0.68 (n-BuOH:HOAc:H$_2$O:EtOAc 1:1:1:1); and 0.70 ( n-BuOH:HOAc:H$_2$O:pyridine 15:5:10:10); HPLC k' 6 (5μ Altex Ultrasphere® ODS, gradient, A:acetonitrile B:water-0.1% trifluoroacetic acid, 10%–50% acetonitrile in 20 min, UV detection at 220 nm), k 3.6 (5μ Altex Ultrasphere® ODS, 20% acetonitrile/water-0.1% trifluoroacetic acid, UV detection at 220 nm); Amino Acid Analysis: Asp (0.81), Gly (1.28), Arg (1.00).

Example 9

Preparation of cyclo-(S,S)-Mba-D-MeArg-Gly-Asp-Man a) Boc-D-MeArg(Tos)-Gly-Asp(O-cHex)-Man(4-MBzl)

To an ice cold solution of the compound of Example 7d (0.6 g, 1.0 mmol) in DMF (42 mL), DIEA (130 μL, 2.2 mmol) was added to bring the pH to neutrality. HOBt (202 mg, 1.5 mmol) was added, followed by Boc-D-MeArg(Tos) (0.663 g, 1.5 mmol). The reaction mixture was stirred for a few min, then EDC (288 mg, 1.5 mmol) was added. The reaction mixture was allowed to warm to room temperature, stirred for 18 h and concentrated to dryness. The residue was dissolved in ethyl acetate and washed successively with water (1×), 10% $K_2CO_3$ (2×), water (1×), 5% citric acid (2×), water (3×) and brine (1×). The ethyl acetate extract was dried (anhydrous $Na_2SO_4$), filtered and concentrated to yield the titled compound (500 mg).

b) D-MeArg(Tos)-Gly-Asp(O-cHex)-Man(4-MBzl)

The compound of Example 9a (500 mg, 0.5 mmol) was treated with 50% TFA (5 mL) according to the procedure of Example 6b to yield the titled compound (658 mg).

c) Mba(SEt)-D-MeArg(Tos)-Gly-Asp(O-cHex)-Man(4-MBzl)

To an ice cold solution of the compound of Example 9b (658 mg, 0.71 mmol) in DMF (4 mL), DIEA (120 mL, 0.85 mmol) was added to bring the pH to neutrality. Mba(SEt) (306 mg, 1.42 mmol) was added, the reaction mixture was stirred for a few min, and EDC (274 mg, 1.42 mmol) and 4-dimethylaminopyridine (174 mg, 1.42 mmol) were added. The reaction mixture was allowed to warm to room temperature, stirred for 18 h, and concentrated to dryness. The residue was dissolved in ethyl acetate and washed successively with water (1×), 10% $K_2CO_3$ (2×), water (1×), 5% citric acid (2×), water (3×) and brine (1×). The ethyl acetate extract was dried (anhydrous $Na_2SO_4$), filtered and concentrated to yield the titled compound (0.37 g).

d) cyclo-(S,S)-Mba-D-MeArg-Gly-Asp-Man

The protected linear peptide of Example 9c (370 mg), was treated with anhydrous HF (10 mL) in the presence of anisole (1 mL) at 0° C. for 1 h. The HF was removed at 0° C. under vacuum, and the residue was triturated with ether. The solid was dried in vacuo to yield the crude cyclized peptide (246 mg). It was purified by gel filtration (Sephadex® G-15, 1% acetic acid/water) The appropriate fractions were pooled and lyophilized to yield the purified titled compound (13 mg). MS (FAB) m/e 602 [M+H]⁺; TLC $R_f$ 0.74 (n-BuOH:HOAc:H₂O:EtOAc 1:1:1:1), $R_f$ 0.68 (n-BuOH:HOAc:H₂O:pyridine 15:5:10:10); HPLC k' 6.7 (5µ Altex Ultrasphere® ODS, gradient, A:acetonitrile B:water-0.1% trifluoroacetic acid, 10%–50% acetonitrile in 20 min, UV detection at 220 nm), k' 6.1 (5µ Altex Ultrasphere® ODS, 21% acetonitrile/water-0.1% trifluoroacetic acid, UV detection at 220 nm); Amino Acid Analysis: Asp (1.00), Gly (1.21).

Example 10

Preparation of cyclo-(S,S)-Mba-MeArg-Gly-Asp-N-Me-Man a) 2-N-Methylaminophenyl disulfide To a solution of 3-methylbenzothiazole (8.0 g, 0.44 mmol) in ethanol (100 mL), solid potassium hydroxide (14.5 g, 0.26 mmol) was added. The reaction mixture was refluxed for 10 h and allowed to cool to room temperature overnight. The solvent was removed and the residue was partitioned between ethyl acetate and aqueous sodium hydroxide (pH 12). The aqueous was treated with concentrated HCl to pH 8, extracted with ethyl acetate, dried, filtered and concentrated to yield the free thiol as an oil (3.0 g). The oil was dissolved in ethyl acetate and air was bubbled through the solution for 90 min. The organic solution was concentrated to yield the titled compound as an oil (2.65 g).

b) N-MeMan(4-MBzl)

To a solution of the compound of Example 10a (2.65 g, 9.6 mmol) in ethanol (150 mL), sodium borohydride (0.36 g, 9.6 mmol) was added portionwise. Upon the completion of addition of the borohydride, the reduction was complete. A solution of α-bromoxylene (3.5 g, 19.2 mmol) in ethanol was added to the reaction mixture, and the mixture was allowed to stir at room temperature overnight. Excess borohydride was filtered off, and the filtrate was chromatographed on silica (2% ethyl acetate-hexane) to yield the titled compound (1.8 g).

c) Boc-Asp(O-cHex)-N-MeMan(4-MBzl)

To a cold solution of Boc-Asp(O-cHex) (1.4 g, 4.5 mmol) and N-methylmorpholine (0.59 mL, 5.3 mmol) in THF (20 mL), isobutylchloroformate (0.69 mL, 5.3 mmol) was added dropwise. The reaction mixture was stirred for a few minutes, then a solution of N-Me-Man(4-MBzl) (1.0 g, 4.1 mmol) in THF (3 mL) was added. The reaction mixture was allowed to warm to room temperature, and stirred for 18 h. Upon completion of the reaction, the amine salt was filtered off and the filtrate was concentrated to dryness. The residue was chromatographed (silica, 20–30% ethyl acetate/hexane) to yield the titled compound (0.95 g).

d) Asp(O-cHex)-N-MeMan(4-MBzl)

Boc-Asp(O-cHex)-N-Me-Man(4-MBzl) (0.88 g, 1.6 mmol) was treated with 50% TFA solution in methylene chloride (5 mL) for 45 min at room temperature. The solvent was removed and methylene chloride was evaporated from the residue several times to eliminate traces of TFA. The product was precipitated by the addition of ether. The solid was collected and air dried to yield the titled compound as white solid.

e) Boc-Gly-Asp(O-cHex)-N-Me-Man(4-MBzl)

To a cold solution of the compound of Example 10d (880 mg, 1.6 mmol) in DMF (5 mL), DIEA (285 µL) was added to bring the pH to neutrality. HOBt (300 mg, 1.92 mmol) was added, followed by Boc-Gly (340 m g, 1.92 mmol). The reaction was stirred in the cold for a few min, then EDC (375 mg, 1.92 mmol) was added portionwise. The reaction mixture was allowed to warm to room temperature, stirred for 18 h and concentrated to dryness. The residue was dissolved in ethyl acetate and washed successively with water (1×), 10% K₂CO₃ (2×), water (1×) and brine (1×). The ethyl acetate extract was dried (anhydrous Na₂SO₄), filtered and concentrated to yield the titled compound (980 mg).

f) Gly-Asp(O-cHex)-N-MeMan(4-MBzl)

The compound of Example 10e (1.3 g, 1.9 mmol) was treated with 50% TFA (10 mL) according to the procedure of Example 6b to yield the titled compound.

g) Boc-MeArg(Tos)-Gly-Asp(O-cHex)-N-MeMan(4-MBzl)

To an ice cold solution of the compound of Example 10f (1.9 mmol) in DMF (4 mL), DIEA (330 µL) was added to bring the pH to neutrality. HOBt (318 mg, 2.1 mmol) was added followed by Boc-N$^α$-Me-Arg(Tos) (920 m g, 2.1 mmol). The reaction mixture was stirred for a few min and EDC (400 mg, 2.13 mmol) was added. The reaction mixture was allowed to warm to room temperature, stirred for 18 h and concentrated to dryness. The residue was dissolved in ethyl acetate and washed successively with water (1×), 10% K₂CO₃(2×), water (1×) and brine (1×). The ethyl acetate extract was dried (anhydrous Na₂SO₄) filtered and concentrated to yield the titled compound (1.7 g).

h) MeArg(Tos)-Gly-Asp(O-cHex)-N-MeMan(4-MBzl)

The compound of Example 10g (1.7 g) was treated with 50% TFA (15 mL) according to the procedure of Example 6b to yield the titled compound (1.36 g, 80%).

i) Mba(SEt)-MeArg(Tos)-Gly-Asp(O-cHex)-NMeMan

To an ice cold solution of the compound of Example 10h (1.3 g, 1.4 mmol) in DMF (2 mL), DIEA (250 µL) was added to bring the pH to neutrality. Mba(SEt) (550 mg, 2.8 mmol) was added, the reaction mixture was stirred for a few min, and EDC (340 mg, 1.54 mmol) was added, followed by 4-dimethylamino-pyridine (350 mg) The reaction mixture was allowed to warm to room temperature, stirred for 18 h and concentrated to dryness. The residue was dissolved in ethyl acetate and washed successively with water (1×), 10% K₂CO₃ (2×), water (1×), 5% citric acid (2×), water (3×) and brine (1×). The ethyl acetate extract was dried (anhydrous Na₂SO₄), filtered and concentrated to yield the titled compound (1.5 g).

j) cyclo-(S,S)-Mba-MeArg-Gly-Asp-N-MeMan

The protected linear peptide of Example 10i (800 mg), was treated with anhydrous HF (10 mL) in the presence of anisole (1 mL) at 0° C. for 1 h. The HF was removed at 0° C. under vacuum, and the residue was triturated with ether. The solid was dried in vacuo to yield the crude cyclized peptide (628 mg). The peptide was purified by chromatography (silica ODS, 20% acetonitrile/water-0.1% TFA) to yield a semipurified compound. An aliquot (20 mg) was purified by HPLC (5µ Altex Ultrasphere® ODS, 10 mm×25 cm, 18% acetonitrile/water-0.1% trifluoroacetic acid, UV detection at 220 nm) to yield the purified titled compound (5.0 mg). MS (FAB) m/e 616.2 [M+H]⁺; TLC $R_f$ 0.82 (n-BuOH:HOAc:H2O:EtOAc 1:1:1:1), $R_f$ 0.77 (n-BuOH:HOAc:H2O:pyridine 15:5:10:10); HPLC k' 10.5 (5 µ Altex Ultrasphere ODS, gradient, A:acetonitrile B:water-0.1% trifluoroacetic acid, 10%–50% acetonitrile in 20 min, UV detection at 220 nm), k' 3.3 (5µ Altex Ultrasphere ODS, 23% acetonitrile/water-0.1% trifluoroacetic acid, UV detection at 220 nm); Amino Acid Analysis: Asp (1.00, Gly (1.05)

Example 11

Preparation of N$^α$AC-cyclo-(S,S)-Cys-MeArg-Gly-Asp-(2R,3S)Pcs-NH₂

The protected pentapeptide resin Boc-Cys(SEt)-MeArg(Tos)-Gly-Asp(O-cHex)-(2R,3S)-3-phenylcysteine(4MBzl)

-MeBHA was prepared according to Example 1 on a 0.5 mmol scale. After removal of the N-terminal Boc group with 50% TFA in methylene chloride and neutralizing the resulting TFA salt with 7% DIEA in methylene chloride, the resin-bound peptide was acetylated with acetic anhydride (0.47 mL), and DIEA (0.86 mL) in methylene chloride (20 mL) for 40 min.

The peptide was cleaved from the resin with removal of the side chain protecting groups by treatment with anhydrous liquid HF (10 mL) in the presence of anisole (1 mL) at 0° C. for 50 min. After removal of the HF under vacuum, the resin was washed with ethyl ether and air-dried. The resin was then extracted with 1% acetic acid/water (2×30 mL) followed by 10% acetic acid/water (2×30 mL). The combined extracts were diluted to 1 L with deionized water. The pH of the aqueous solution was adjusted to 7.65 with con. ammonium hydroxide, and cyclized by bubbling an inert gas such as argon in which the free sulfhydryl group, generated from the cleavage of the MBzl protecting one of sulfur, displaces the SEt group protecting the other sulfur. The cyclization process was achieved in 48–72 h. The solution was chromatographed (ODS silica, step gradient: a) water b) 12% acetonitrile-0.1% TFA-water). The appropriate fractions were pooled, evaporated to dryness and the residue was lyophilized from 1% acetic acid/water to yield the purified titled peptide (80 mg). MS(FAB)m/e 682.2 [M+H]$^+$; TLC R$_f$ 0.56 (n-BuOH:HOAc:H$_2$O:EtOAc 1:1:1:1), R$_f$ 0.61 (n-BuOH:HOAc:H$_2$O:pyridine 15:5:10:10); HPLC k' 13.1 (5µ 5µ Altex Ultrasphere® ODS, gradient, A:acetonitrile B:water-0.1% trifluoroacetic acid, 0–50% acetonitrile in 20 min, UV detection at 220 nm), k' 5.7 (5µ 5µ Altex Ultrasphere® ODS, 15% acetonitrile/water-0.1% trifluoroacetic acid, UV detection at 220 nm), Amino Acid Analysis: Asp(0.97), Gly(1.00), Cys(0.38), β-phenyl-Cys(0.63).

Example 12

Preparation of N$^\alpha$Ac-cyclo-(S,S)-Cys-MeArg-Gly-Asp-(2R,3R)Pcs-NH$_2$

The protected pentapeptide resin Boc-Cys(SEt)-MeArg(Tos)-Gly-Asp(O-cHex)-(2R,3R)-3-phenylcysteine (4MBzl)-MeBHA was prepared according to Example 1 on a 0.5 mmol scale. After removal of the N-terminal Boc group with 50% TFA in methylene chloride and neutralizing the resulting TFA salt with 7% DIEA in methylene chloride, the resin-bound peptide was acetylated with acetic anhydride (0.47 mL) and DIEA (0.86 mL) in methylene chloride (20 mL) for 40 min.

The peptide was cleaved from the resin with removal of the side chain protecting groups by treatment with anhydrous HF (10 mL) in the presence of anisole (1 mL) at 0° C. for 50 min. After removal of the HF under vacuum, the resin was washed with ethyl ether and air-dried. The resin was then extracted with 1% acetic acid/water (2×30 mL) followed by 10% acetic acid/water (2×30 mL). The combined extracts were diluted to 1L with deionized water. The pH of the aqueous solution was adjusted to 7.65 with ammonium hydroxide, and cyclized by bubbling argon through the solution (argon drives off ethanethiol liberated by free sulfhydryl group of Pcs nucleophically displacing the SEt group protecting cysteine sulfhydryl). After 72 h, the solution was chromatographed (ODS silica, step gradient: a) water b) 11% acetonitrile/water-0.1% TFA). The appropriate fractions were pooled, evaporated to dryness and the residue was lyophilized from 1% acetic acid/water to yield titled peptide (92 mg). MS(FAB) m/e 682 [M+H]$^+$; TLC R$_f$ 0.70 (n-BuOH:HOAc:H$_2$O:EtOAc 1:1:1:1), 0.67 (n-BuOH:HOAc:H$_2$O:pyridine 15:5:10:10); HPLC k' 8.35 (5µ Altex Ultrasphere® ODS, gradient, A:acetonitrile B:water-0.1% trifluoroacetic acid, 0–50% acetonitrile in 20 min, UV detection at 220 nm), k' 4.45 (5µ Altex Ultrasphere® ODS, 12% acetonitrile/water-0.1% trifluoroacetic acid, UV detection at 220 nm); Amino Acid Analysis: Asp(1.00), Gly(0.96), Cys(0.38), β-phenylCys(0.56).

Example 13

Preparation of N$^\alpha$Ac-cyclo-(S,S) Cys-Arg-Gly-Asp-Ser-Arg-Gly-Asp-Ser-Cys-NH$_2$ The protected decapeptide resin Boc-Cys(MBzl)-Arg(Tos)-Gly-Asp(O-cHex)-Ser(Bzl)-Arg(Tos)-Gly-Asp(O-cHex)-Ser(Bzl)-Cys(SEt)-MeBHA was prepared according to Example 1 on a 1.0 mmol scale. After removal of the N-terminal Boc group with 50% TFA in methylene chloride and neutralizing the resulting TFA salt with 7% DIEA in methylene chloride, the resin-bound peptide was acetylated with acetic anhydride (0.94 mL), and DIEA (1.72 mL) in DMF (30 mL) for 40 min.

The peptide was cleaved from the resin with removal of the side chain protecting groups by treatment with anhydrous liquid HF (30 mL) in the presence of anisole (3 mL) at 0° C. for 50 min. After removal of the HF under vacuum, the resin was washed with ethyl ether and air-dried. The resin was then extracted with 1% acetic acid/water (2×30 mL) followed by 10% acetic acid/water (2×30 mL). The combined extracts were diluted to 2 L with deionized water. The pH of the aqueous solution was adjusted to 7.65 with ammonium hydroxide and argon was bubbled through the reaction mixture for 72 h. The solution was chromatographed (ODS silica, step gradient: a) water b) 5% acetonitrile-0.1% TFA-water). The appropriate fractions were pooled, evaporated to dryness and the residue was lyophilized from 1% acetic acid/water to yield a semipurified peptide (800 mg, 80%). An aliquot (172 mg) was purified by gel filtration (Sephadex® G-15, 1% acetic acid/water). The appropriate fractions were pooled and lyophilized to yield the purified titled compound (74 mg). MS(FAB) m/e 1094.3 [M+H]$^+$; TLC R$_f$ 0.25 (n-BuOH:HOAc:H$_2$O:EtOAc 1:1:1:1), R$_f$ 0.37 (n-BuOH:HOAc:H$_2$O:pyridine 15:5:10:10); HPLC k' 7.5 (5µ Altex Ultrasphere® ODS, gradient, A:acetonitrile B:water-0.1% trifluoroacetic acid, 0–50% acetonitrile in 20 min, UV detection at 220 nm), k' 4.3 (5µ Altex Ultrasphere® ODS, 5% acetonitrile/water-0.1% trifluoroacetic acid, UV detection at 220 nm); Amino Acid Analysis: Asp(2.00), Gly(2.07), Cys(2.09), Ser(1.91), Arg(1.89).

Example 14

Preparation of N$^\alpha$Ac-cyclo-(S,S)-Cys-Arg-Gly-Asp-Ser-Arg-Gly-Asp-Ser-Pen-NH$_2$ The protected decapeptide resin Boc-Cys(SEt)-Arg(Tos)-Gly-Asp(O-cHex)-Ser(Bzl)-Arg(Tos)-Gly-Asp(O-cHex)-Ser(Bzl)-Cys(4MBzl)-MeBHA was prepared according to Example 1 on a 1.0 mmol scale. After removal of the N-terminal Boc group with 50% TFA in methylene chloride and neutralizing the resulting TFA salt with 7% DIEA in methylene chloride, the resin-bound peptide was acetylated with acetic anhydride (0.94 mL), and DIEA (1.72 mL) in DMF (30 mL) for 40 min.

The peptide was cleaved from the resin with removal of the side chain protecting groups by treatment with anhydrous liquid HF (30 mL) in the presence of anisole (3 mL) at 0° C. for 50 min. After removal of the HF under vacuum, the resin was washed with ethyl ether and air-dried. The resin was then extracted with 1% acetic acid/water (2×30 mL) followed by 10% acetic acid/water (2×30 mL). The combined extracts were diluted to 2 L with deionized water. The pH of the aqueous solution was adjusted to 7.5–8.0 with ammonium hydroxide and argon was bubbled through the reaction mixture for 72 h. The solution was chromatographed (ODS silica, step gradient: a) water b) 6% acetonitrile-0.1% TFA-water). The appropriate fractions were pooled, evaporated to dryness and the residue was lyophilized from 1% acetic acid/water to yield a crude peptide (1.0 g, 100%). An aliquot (106 mg) was purified by gel filtration (Sephadex® G-15, 1% acetic acid/water). The appropriate fractions were pooled and lyophilized to yield a semipurified peptide (90 mg). An aliquot of the semipurified peptide (60 mg) was purified by HPLC (5μ Altex Ultrasphere® ODS, 7% acetonitrile/water-0.1% trifluoroacetic acid, UV detection at 220 nm) to yield the purified titled compound (56 mg). MS(FAB) m/e 1122.6 [M+H]$^+$; TLC R$_f$ 0.34 (n-BuOH:HOAc:H$_2$O:EtOAc 1:1:1:1), R$_f$ 0.49 (n-BuOH:HOAc:H$_2$O:pyridine 15:5:10:10); HPLC k' 8.18 (5μ Altex Ultrasphere® ODS, gradient, A:acetonitrile B:water-0.1% trifluoroacetic acid, 0–50% acetonitrile in 20 min, UV detection at 220 nm), k 7.1 (5μ Altex Ultrasphere® ODS, 6.5% acetonitrile/water-0.1% trifluoroacetic acid, UV detection at 220 nm); Amino Acid Analysis: Asp(2.00), Gly(2.21), Cys+Pen(1.66), Ser(1.96), Arg(2.16).

Example 15

Preparation of N$^\alpha$Ac-cyclo-(S,S) Cys-Arg-Gly-Asp-Ser-MeArg-Gly-Asp-Ser-Cys-NH$_2$ The protected decapeptide resin Boc-Cys(SEt)-Arg(Tos)-Gly-Asp(O-cHex)-Ser(Bzl)-MeArg(Tos)-Gly-Asp(O-cHex)-Ser(Bzl)-Cys(4MBzl)-MeBHA was prepared according to Example 1 on a 1.0 mmol scale. After removal of the N-terminal Boc group with 50% TFA in methylene chloride and neutralizing the resulting TFA salt with 7% DIEA in methylene chloride, the resin-bound peptide was acetylated with acetic anhydride (0.94 mL), and DIEA (1.72 mL) in DMF (30 mL) for 40 min.

The peptide was cleaved from the resin with removal of the side chain protecting groups by treatment with anhydrous liquid HF (30 mL) in the presence of anisole (3 mL) at 0° C. for 50 min. After removal of the HF under vacuum, the resin was washed with ethyl ether and air-dried. The resin was then extracted with 1% acetic acid/water (2×30 mL) followed by 10% acetic acid/water (2×30 mL). The combined extracts were diluted to 1.5 L with deionized water. The pH of the aqueous solution was adjusted to 7.9 with ammonium hydroxide and argon was bubbled through the reaction mixture for 72 h. The solution was lyophilized to yield a crude peptide (409 mg). An aliquot (209 mg) was purified by gel filtration (Sephadex® G-15, 1% acetic acid/water). The appropriate fractions were pooled and lyophilized to yield the purified titled compound (20 mg). MS(FAB) m/e 1108.3 [M+H]$^+$; TLC R$_f$ 0.23 (n-BuOH:HOAc:H$_2$O:EtOAc 1:1:1:1), R$_f$ 0.45 (n-BuOH:HOAc:H$_2$O:pyridine 15:5:10:10); HPLC k' 5.6 (5μ Altex Ultrasphere® ODS, gradient, A:acetonitrile B:water-0.1% trifluoroacetic acid, 0–50% acetonitrile in 20 min, UV detection at 220 nm), k' 0.6 (5μ Altex Ultrasphere® ODS, 10% acetonitrile/water-0.1% trifluoroacetic acid, UV detection at 220 nm); Amino Acid Analysis: Asp(2.11), Gly(2.06), Cys(1.84), Ser(2.00), Arg(0.84).

Example 16

Preparation of N$^\alpha$Ac-cyclo-(S,S)-Cys-MeArg-Gly-Asp-Ser-Arg-Gly-Asp-Ser-Cys-NH$_2$ The protected decapeptide resin Boc-Cys(SEt)-MeArg(Tos)-Gly-Asp(O-cHex)-Ser(Bzl)-Arg(Tos)-Gly-Asp(O-cHex)-Ser(Bzl)-Cys(4MBzl)-MeBHA was prepared according to Example 1 on a 1.0 mmol scale. After removal of the N-terminal Boc group with 50% TFA in methylene chloride and neutralizing the resulting TFA salt with 7% DIEA in methylene chloride, the resin-bound peptide was acetylated with acetic anhydride (0.94 mL) and DIEA (1.72 mL) in DMF (30 mL) for 40 min.

The peptide was cleaved from the resin with removal of the side chain protecting groups by treatment with anhydrous liquid HF (10 mL) in the presence of anisole (1 mL) at 0° C. for 50 min. After removal of the HF under vacuum, the resin was washed with ethyl ether and air-dried. The resin was then extracted with 1% acetic acid/water (2×30 mL) followed by 10% acetic acid/water (2×30 mL). The combined extracts were diluted to 1.5 L with deionized water. The pH of the aqueous solution was adjusted to 7.6 with ammonium hydroxide and argon was bubbled through the reaction mixture for 72 h. The solution was chromatographed (ODS silica, step gradient: a) water b) 5% acetonitrile-0.1% TFA-water). The appropriate fractions were pooled, evaporated to dryness and the residue was lyophilized from 1% acetic acid/water to yield a semipurified peptide (800 mg). An aliquot (200 mg) was purified by gel filtration (Sephadex® G-15, 1% acetic acid/water). The appropriate fractions were pooled and lyophilized to yield the purified titled compound (90 mg). MS(FAB) m/e 1108.4 [M+H]$^+$; TLC R$_f$ 0.29 (n-BuOH:HOAc:H$_2$O:EtOAc 1:1:1:1), R$_f$ 0.32 (n-BuOH:HOAc:H$_2$O:pyridine 15:5:10:10); HPLC k' 6.6 (5μ Altex Ultrasphere® ODS, gradient, A:acetonitrile B:water-0.1% trifluoroacetic acid, 5–50% acetonitrile in 20 min, UV detection at 220 nm), k' 6.6 (5μ Altex Ultrasphere® ODS, 4% acetonitrile/water-0.1% trifluoroacetic acid, UV detection at 220 nm); Amino Acid Analysis: Asp(2.00), Gly(2.21), Cys(1.45), Ser(1.70), Arg(1.12).

Example 17

Preparation of N$^\alpha$Ac-cyclo-(S,S)-Cys-Arg-Gly-Asp-Ser-Lys-Gly-Glu-Ser-Cys-NH$_2$ The protected decapeptide resin Boc-Cys(SEt)-Arg(Tos)-Gly-Asp(O-Bzl)-Ser(Bzl)-Lys(ClZ)-Gly-Glu(O-Bzl)-Ser(Bzl)-Cys(4-MBzl)-MeBHA was prepared according to Example 1 on a 0.5 mmol scale. After removal of the N-terminal Boc group with 50% TFA in methylene chloride and neutralizing the resulting TFA salt with 7% DIEA in methylene chloride, the resin-bound peptide was acetylated with acetic anhydride (0.94 mL) and DIEA (1.72 mL) in DMF (30 mL) for 40 min.

The peptide was cleaved from the resin with removal of the side chain protecting groups by treatment with anhydrous liquid HF (20 mL) in the presence of anisole (2 mL) at 0° C. for 50 min. After removal of the HF under vacuum, the resin was washed with ethyl ether and air-dried. The resin was then extracted with 1% acetic acid/water (2×30 mL) followed by 10% acetic acid/water (2×30 mL). The combined extracts were diluted to 2 L with deionized water. The pH of the aqueous solution was adjusted to 7.65 with ammonium hydroxide and argon was bubbled through the reaction mixture for 72 h. The solution was lyophilized and chromatographed (ODS silica, 4% acetonitrile-0.1% TFA-water). The appropriate fractions were pooled, evaporated to dryness and the residue was lyophilized from 1% acetic acid/water to yield a partially purified peptide (120 mg). The peptide was further purified by gel filtration (Sephadex®

G-15, 1% acetic acid/water). The appropriate fractions were pooled and lyophilized to yield the purified titled compound (40 mg). MS(FAB) m/e 1080 [M+H]$^+$; TLC R$_f$ 0.23 (n-BuOH:HOAc:H$_2$O:EtOAc 1:1:1:1), R$_f$ 0.38 (n-BuOH:HOAc:H$_2$O:pyridine 15:5:10:10); HPLC k' 9.4 (5μ Altex Ultrasphere® ODS, gradient, A:acetonitrile B:water-0.1% trifluoroacetic acid, 5%–50% acetonitrile in 20 min, UV detection at 220 nm), k' 5.6 (5μ Altex Ultrasphere® ODS, 3% acetonitrile/water-0.1% trifluoroacetic acid, UV detection at 220 nm); Amino Acid Analysis: Asp(1.00), Gly(2.12), Cys(1.83), Ser(1.69), Glu(1.09), Lys (1.03), Arg(0.90).

Example 18

Preparation of cyclo-(1$^\alpha$,6$^\gamma$)-Gly-Arg-Gly-Asp-Ser-Glu-NH$_2$

The protected hexapeptide resin Boc-Gly-Arg(Tos)-Gly-Asp(Bzl)-Ser(Bzl)-Glu(O-t-Bu)-BHA was prepared according to Example 1 on a 1 mmol scale. The N-terminal Boc group on glycine and the t-butyl ester on the glutamic acid sidechain were removed with 50% TFA in methylene chloride. The resulting TFA salt was neutralized with 7% DIEA in methylene chloride and the resin-bound peptide was cyclized between the alpha amine of glycine and the gamma carboxy group of glutamic acid using the BOP reagent (3 mmol) and DIEA (6 mmol) in DMF. Complete cyclization was tested by ninhydrin test and repeated as required.

The peptide was cleaved from the resin with removal of the sidechain protecting groups by treatment with anhydrous liquid HF (30 mL) in the presence of anisole (3 mL) at 0° C. for 50 min. After removal of the HF under vacuum, the resin was washed with ethyl ether and air-dried. The resin was then extracted with 1% acetic acid/water (2×30 mL) followed by 10% acetic acid/water (2×30 mL). The combined extracts were lyophilized to yield a crude peptide (566 mg, 94%).

The crude peptide was purified by flash chromatgraphy (ODS reversed-phase silica, 1% acetonitrile/water-0.1% TFA). The appropriate fractions were pooled, evaporated to dryness and the residue was lyophilized from 1% acetic acid/water to yield a partially purified peptide (137 mg). An aliquot of partially purified peptide (90 mg) was further purified by HPLC (5μ Altex Ultrasphere® ODS, 1.5% acetonitrile/water-0.1% trifluoroacetic acid, UV detection at 220 nm) to yield the purified titled compound (31 mg). MS(FAB) m/e 601.2 [M+H]$^+$; TLC R$_f$ 0.49 TLC R$_f$ 0.38 (n-BuOH:HOAc:H$_2$O:EtOAc 1:1:1:1), R$_f$ 0.46 (n-BuOH:HOAc:H$_2$O:pyridine 15:5:10:10); HPLC k' 7.4 (5μ Altex Ultrasphere® ODS, gradient, A:acetonitrile B:water-0.1% trifluoroacetic acid, 0–50% acetonitrile in 20 min, UV detection at 220 nm), k' 5.88 (5μ Altex Ultrasphere® ODS, 1% acetonitrile/water-0.1% trifluoroacetic acid, UV detection at 220 nm); Amino Acid Analysis: Asp(0.85), Gly(2.00), Ser(1.00), Glu(1.06), Arg(1.04).

Example 19

Preparation of cyclo (1$^\alpha$,6$^\gamma$)-Gly-MeArg-Gly-Asp-Ser-Glu-NH$_2$

The protected hexapeptide resin Boc-Gly-MeArg(Tos)-Gly-Asp(Bzl)-Ser(Bzl)Glu(t-But)-BHA was prepared according to Example 1 on a 1 mmol scale. The N-terminal Boc group on glycine and the t-butyl ester on the glutamic acid sidechain were removed with 50% TFA in methylene chloride. The resulting TFA salt was neutralized with 7% DIEA in methylene chloride and the resin-bound peptide was cyclized between the alpha amine of glycine and the gamma carboxy group of glutamic acid using the BOP reagent (3 mmol) and DIEA (6 mmol) in DMF.

The peptide was cleaved from the resin with removal of the side chain protecting groups by treatment with anhydrous liquid HF (30 mL) in the presence of anisole (3 mL) at 0° C. for 50 min. After removal of the HF under vacuum, the resin was washed with ethyl ether and air-dried. The resin was then extracted with 1% acetic acid/water (2×30 mL) followed by 10% acetic acid/water (2×30 mL). The combined extracts were lyophilized to yield a crude peptide (680 mg, 100%).

The crude peptide was purified by flash chromatgraphy (ODS reversed-phase silica, 1.5% acetonitrile/water-0.1% TFA). The appropriate fractions were pooled, evaporated to dryness and the residue was lyophilized from 1% acetic acid/water to yield a partially purified peptide (356.8 mg). An aliquot of partially purified peptide (66 mg) was further purified by HPLC (5μ Altex Ultrasphere® ODS, 2% acetonitrile/water-0.1% trifluoroacetic acid, UV detection at 220 nm) to yield the purified titled compound (31 mg). MS(FAB) m/e 615 [M+H]$^+$; TLC R$_f$ 0.36 TLC R$_f$ 0.38 (n-BuOH:HOAc:H$_2$O:EtOAc 1:1:1:1), R$_f$ 0.42 (n-BuOH:HOAc:H$_2$O:pyridine 15:5:10:10); HPLC k' 7.43 (5μ Altex Ultrasphere® ODS, gradient, A:acetonitrile B:water-0.1% trifluoroacetic acid, 0–50% acetonitrile in 20 min, UV detection at 220 nm), k' 4.43 (5μ Altex Ultrasphere® ODS, 3% acetonitrile/water-0.1% trifluoroacetic acid, UV detection at 220 nm); Amino Acid Analysis: Asp(1.00), Gly(1.88), Ser(0.85), Glu(1.05).

Example 20

Preparation of cyclo-(1,8)-Arg-Gly-Asp-Phe-Arg-Gly-Asp-Phe General procedure for solid phase peptide synthesis of Homodetic peptides—FMOC-SASRIN Method Cyclic homodetic peptides were synthesized by solid phase peptide synthesis using SASRIN resin (Bachem) as the support. Protected amino acids were added sequentially starting from the carboxy terminus until the desired sequence was obtained. The 9-fluorenylmethoxycarbonyl (FMOC) group was used for protection of the alpha amino group. Side chain functional groups were protected as follows: arginine and N$^\alpha$-methylarginine, tosyl (Tos) or 4-methoxyl-2,3,6-trimethylphenylsulfonyl (Mtr); serine, benzyl ether (Bzl); glutamic and aspartic, benzyl (Bzl) or t-butyl ester (t-Bu). Removal of the FMOC group was accomplished by treatment with 20% piperidine in DMF. Amino acids were coupled to the growing peptide using 2–3 equivalents of the FMOC-protected amino acid, 2–3 equivalents of HOBt in DMF and 2–3 equivalents of DCC in methylene chloride. Completeness of coupling was checked by the ninhydrin test and couplings were repeated as necessary. The general protocol is given below.

| | |
|---|---|
| 1. Wash with DMF | 5 × 1 min. |
| 2. Wash with 20% piperidine in DMF | 1 × 1 min |
| 3. Deprotect with 20% pip.in DMF | 1 × 7 min |
| 4. Wash with DMF | 10 × 1 min |
| 5. Test for deprotection by ninhydrin | |
| 6. FMOC-AA + HOBt in DMF, do not drain | 2 min |
| 7. DCC in methylene chloride | 2 h |
| 8. Wash with DMF | 5 × 1 min |
| 9. Wash with methylene chloride | 3 × 1 min |
| 10. Test for complete coupling by ninhydrin | |
| 11. Continue from step 1 if negative ninhydrin obtained or recouple from step 6 if positive ninhydrin obtained. | |

Upon completion of the desired protected peptide, the FMOC protection of the N-terminus is removed, and the protected peptide is cleaved from the resin using 1–2% trifluoroacetic acid (TFA) in methylene chloride (3×15 min). The methylene chloride/TFA extracts are combined and concentrated to yield the protected peptide.

To effect cyclization, the protected peptide (0.2 mmol, 0.4 mM solution in dry DMF) is treated with N-methylmorpholine (5 equivalents) and 1-propanephosphonic acid cyclic anhydride (PPA) (1.2 equivalents) at 0° C. for 1 h. Another equivalent of PPA is added, and the reaction mixture is allowed to stir at room temperature for 18 h. The solvent is removed, and the residue is triturated with water to yield the desired cyclic protected peptide. Protected sidechain functional groups are deprotected by treatment with anhydrous HF in the presence of anisole (10%) at 0° C. for 50 min. The HF is removed under vacuum, the crude peptide is dissolved in acetic acid (0.2M), washed with ether (3×) and lyophilized to yield the desired crude peptide.

cyclo-(1,8)-Arg-Gly-Asp-Phe-Arg-Gly-Asp-Phe

The protected octapeptide resin FMOC-Asp(O-t-Bu)-Phe-Arg(Mtr)-Gly-Asp(O-t-Bu)-Phe-Arg(Mtr)-Gly-SASRIN was prepared as described above on a 2 mmol scale. After the removal of the N-terminal FMOC group with 20% piperidine in DMF, the resin-bound peptide was cleaved from the resin with 1% TFA in methylene chloride to yield Asp(O-t-Bu)-Phe-Arg(Mtr)-Gly-Asp(O-t-Bu)-Phe-Arg(Mtr)-Gly (2.9 g,97%) as a white solid. To the protected peptide (300 mg, 0.2 mmol) DMF (500 mL) at 0° C., NMM (110 μL,1.0 mmol) was added, followed by PPA (152 μL,0.24 mmol). After stirring at 0° C. for 1 h, another portion of PPA was added and stirring was continued for 18 h. Removal of the solvent and trituration of the residue with water affords the cyclized protected peptide cyclo-(1,8)Arg(Mtr)-Gly-Asp(O-t-Bu)-Phe-Arg(Mtr)-Gly-Asp(O-t-Bu)-Phe (325 mg, 100%). The peptide was treated with anhydrous HF (20 mL) in the presence of anisole (2 mL) at 0° C. for 50 min. After removal of HF under vacuum, the unprotected peptide was dissolved in 60 mL of 0.2M acetic acid, washed with ether (3×20 mL) and lyophilized to yield the crude cyclo(1,8)Arg-Gly-Asp-Phe-Arg-Gly-Asp-Phe (247 mg). The crude peptide was purified by gel filtration (Sephadex® G-15, 1% acetic acid/water). The appropriate fractions were pooled and lyophilized. It was then further purified by HPLC (5μ Altex Ultrasphere® ODS, gradient, A:acetonitrile B:water-0.1% trifluoroacetic acid, 10–40% acetonitrile in 10 min, UV detection at 220 nm) to yield the purified titled compound (26 mg). MS(FAB) m/e 951.2[M+H]$^+$; TLC R$_f$ 0.61(n-BuOH:HOAc:H$_2$O:EtOAc 1:1:1:1), R$_f$ 0.63 (n-BuOH:HOAc:H$_2$O:pyridine 15:5:10:10); HPLC k' 7.73 (5μ Altex Ultrasphere® ODS, gradient, A:acetonitrile B:water-0.1% trifluoroacetic acid, 0–50% acetonitrile in 20 min, UV detection at 220 nm), k' 4.29 (5μ Altex Ultrasphere® ODS, 20% acetonitrile/water-0.1% trifluoroacetic acid, UV detection at 220 nm); Amino Acid Analysis: Asp(2.00), Gly(2.08), Phe(2.01), Arg(1.89).

Example 21

Preparation of cyclo-(1,8)-MeArg-Gly-Asp-Phe-Arg-Gly-Asp-Phe

The protected octapeptide resin FMOC-Asp(O-t-Bu)-Phe-MeArg(Tos)-Gly-Asp(O-t-Bu)-Phe-Arg(Mtr)-Gly-SASRIN was prepared according to Example 20 on 1 mmol scale. After the removal of the N-terminal FMOC group with 20% piperidine in DMF, the resin-bound peptide was cleaved from the resin with 1% TFA in methylene chloride to give the protected linear peptide (1.22 g, 84%) as a white solid. The protected peptide (585 mg, 0.4 mmol) in DMF (1 L) was treated with NMM (220 μL, 2.0 mmol) and PPA (304 μL,0.48 mmol) at 0° C. After an hour stirring at 0° C., another portion of PPA was added and stirring was continued for 18 h. Removal of the solvent and triturating the residue with water afforded the cyclized protected peptide cyclo-(1,8)-MeArg(Tos)-Gly-Asp(O-t-Bu)-Phe-Arg(Mtr)-Gly-Asp(O-t-Bu)-Phe (550 mg, 95%). The peptide was treated with anhydrous HF (30 mL) in the presence of anisole (3 mL) at 0° C. for 50 min. After removal of HF under vacuum, the peptide was dissolved in 60 mL of 0.2M acetic acid, washed with ether (3×20 mL) and lyophilized to give the crude cyclo-(1,8)-MeArg-Gly-Asp-Phe-Arg-Gly-Asp-Phe (406 mg). The crude peptide (200 mg) was purified by gel filtration (Sephadex® G-15, 1% acetic acid/water). The appropriate fractions were pooled and lyophilzed. The peptide was further purified by HPLC (5μ Altex Ultrasphere® ODS, 5 μL 10 mm×25 cm, gradient, A:acetonitrile B:water-0.1% trifluoroacetic acid, 10–50% acetonitrile in 10 min, UV detection at 220 nm) to yield the purified titled compound (26 mg). MS(FAB) m/e 965.4 [M+H]$^+$; TLC R$_f$ 0.65 (n-BuOH:HOAc:H$_2$O:EtOAc 1:1:1:1), R$_f$ 0.63 (n-BuOH:HOAc:H$_2$O:pyridine 15:5:10:10); HPLC k' 8.14 (5μ Altex Ultrasphere® ODS, gradient, A:acetonitrile B:water-0.1% trifluoroacetic acid, 0–50% acetonitrile in 20 min, UV detection at 220 nm), k' 9 (5μ Altex Ultrasphere® ODS, 14% acetonitrile/water-0.1% trifluoroacetic acid, UV detection at 220 nm); Amino Acid Analysis: Asp(1.97), Gly(2.00), Phe(1.95), Arg(1.03).

Example 22

Preparation of cyclo-(1,10)-Pro-Arg-Gly-Asp-D-Phe-Pro-Arg-Gly-Asp-D-Phe

The protected decapeptide resin FMOC-Asp(O-t-Bu)-D-Phe-Pro-Arg(Mtr)-Gly-Asp(O-t-Bu)-D-Phe-Pro-Arg(Mtr)-Gly-SASRIN was prepared according to Example 20 on 1 mmol scale. After the removal of the N-terminal FMOC group with 20% piperidine in DMF, the resin-bound peptide was cleaved from the resin with 1.5% TFA in methylene chloride to give Asp(O-t-Bu)-D-Phe-Pro-Arg(Mtr)-Gly-Asp(O-t-Bu)-D-Phe-Pro-Arg(Mtr)-Gly (1.7 g, 100%) as a white solid. The protected peptide (509 mg, 0.3 mmol) in DMF (750 mL) was treated with NMM (165 μL, 1.5 mmol) and PPA (228 μL,0.36 mmol) at 0° C. After stirring at 0° C. for 1 h, another portion of PPA was added and stirring was continued for 18 h. Removal of the solvent and trituration of the residue with water gave the cyclized protected peptide, cyclo-(1,10)-Pro-Arg(Mtr)-Gly-Asp(O-t-Bu)-D-Phe-Pro-Arg(Mtr)-Gly-Asp(O-t-Bu)-D-Phe (1.0 g, 100%). The peptide was treated with anhydrous HF (30 mL) in the presence of anisole (3 mL) at 0° C. for 50 min. After removal of the HF under vacuum, the peptide was dissolved in 0.2M acetic acid (60 mL), washed with ether (3×20 mL) and lyophilized to give the crude cyclo-(1,10)Pro-Arg-Gly-Asp-D-Phe-Pro-Arg-Gly-Asp-D-Phe (370 mg). The crude peptide (196 mg) was purified by gel filtration (Sephadex® G-15, 1% acetic acid/water). The appropriate fractions were pooled and lyophilized. An aliquot of partially purified peptide (58 mg) was further purified by HPLC (5μ Altex Ultrasphere® ODS, 26% acetonitrile/water-0.1% trifluoroacetic acid, UV detection at 220 nm) to yield the purified titled compound (24 mg). MS(FAB) m/e 1145.5 [M+H]$^+$; TLC R$_f$ 0.55 (n-BuOH:HOAc:H$_2$O:EtOAc 1:1:1:1), R$_f$ 0.58 (n-BuOH:HOAc:H$_2$O:pyridine 15:5:10:10); HPLC k' 12.9 (5μ Altex Ultrasphere® ODS, gradient, A:acetonitrile B:water-0.1% trifluoroacetic acid, 0–50% acetonitrile in 20 min, UV detection at 220 nm), k' 6.09 (5μ Altex Ultrasphere® ODS, 25% acetonitrile/water-0.1% trifluoroacetic acid, UV detection at 220 nm); Amino Acid Analysis: Asp(2.00), Gly(2.08), Pro(2.71), Phe(2.02), Arg(1.74).

Example 23

Preparation of cyclo-(1,6)-Gly-Pro-Arg-Gly-Asp-D-Pro

The protected hexapeptide resin FMOC-Asp(O-t-Bu)-D-Pro-Gly-Pro-Arg(Mtr)-Gly-SASRIN was prepared according to Example 20 on 1 mmol scale. After the removal of the N-terminal FMOC group with 20% piperidine in DMF, the resin-bound peptide was cleaved from the resin with 2% TFA in methylene chloride to give Asp(O-t-Bu)-D-Pro-Gly-Pro-Arg(Mtr)-Gly as a white solid (1.2 g, 100%). The protected peptide (703 mg, 0.8 mmol) in DMF (2 L) was treated with NMM (440 µL, 4.0 mmol) and PPA (608 µL, 0.95 mmol) at 0° C. After stirring at 0° C. for 1 h, another portion of PPA was added and stirring was continued for 18 h. Removal of the solvent and trituration of the residue with water gave the cyclized protected peptide (286 mg, 42%). The peptide was treated with anhydrous HF (20 mL) in the presence of anisole (2 mL) at 0° C. for 50 min. After removal of HF under vacuum, the deprotected peptide was dissolved in 0.2M acetic acid (60 mL), washed with ether (3×20 mL) and lyophilized to yield the crude cyclo-(1,6)-Gly-Pro-Arg-Gly-Asp-D-Pro (280 mg). An aliquot of the crude peptide (223 mg) was purified by gel filtration (Sephadex® G-15, 1% acetic acid/water). The appropriate fractions were pooled and lyophilized to yield the purified titled compound (147 mg). MS(FAB) m/e 580.3 [M+H]⁺; TLC $R_f$ 0.44 (n-BuOH:HOAc:H$_2$O:EtOAc 1:1:1:1), $R_f$ 0.45 (n-BuOH:HOAc:H$_2$O:pyridine 15:5:10:10); HPLC k' 6.87 (5µ Altex Ultrasphere® ODS, gradient, A:acetonitrile B:water-0.1% trifluoroacetic acid, 0–50% acetonitrile in 20 min, UV detection at 220 nm), k' 3.98 (5µ Altex Ultrasphere® ODS, 5% acetonitrile/water-0.1% trifluoroacetic acid, UV detection at 220 nm); Amino Acid Analysis: Asp(1.00), Gly(2.00), Pro(2.00), Arg(1.05).

Example 24

Preparation of cyclo-(1,6)-Pro-Gly-Arg-Gly-Asp-D-Pro

The protected hexapeptide resin FMOC-Asp(O-t-Bu)-D-Pro-Pro-Gly-Arg(Mtr)-Gly-SASRIN was prepared according to Example 20 on 1 mmol scale. After the removal of the N-terminal FMOC group with 20% piperidine in DMF, the resin-bound peptide was cleaved from the resin with 2% TFA in methylene chloride to give the protected linear peptide as a white solid (921 mg, 100%). The protected peptide (320 mg, 0.37 mmol) in DMF (1 L) was treated with NMM (220 µL, 2.0 mmol) and PPA (304 µL, 0.48 mmol) at 0° C. After stirring at 0° C. for 1 h, another portion of PPA was added and stirring was continued for 18 h. Removal of the solvent and trituration of the residue with water gave the cyclized protected peptide, cyclo-(1,6)-Pro-Gly-Arg(Mtr)-Gly-Asp(O-t-Bu)-D-Pro (97 mg, 31%). The protected peptide (168 mg) was treated with anhydrous HF (20 mL) in the presence of anisole (2 mL) at 0° C. for 50 min. After removal of HF under vacuum, the deprotected peptide was taken into 60 mL of 0.2M acetic acid, washed with ether (3×20 mL) and lyophilized to give cyclo-(1,6)-Pro-Gly-Arg-Gly-Asp-D-Pro (156 mg). An aliquot of the crude peptide (150 mg) was purified by gel filtration (Sephadex® G-15, 1% acetic acid/water). The appropriate fractions were pooled and lyophilized to yield the purified titled compound (50 mg). MS(FAB) m/e 580.3 [M+H]⁺; TLC $R_f$ 0.3 (n-BuOH:HOAc:H$_2$O:EtOAc 1:1:1:1), $R_f$ 0.42 (n-BuOH:HOAc:H$_2$O:pyridine 15:5:10:10); HPLC k' 9.44 (5µ Altex Ultrasphere® ODS, gradient, A:acetonitrile B:water-0.1% trifluoroacetic acid, 0–50% acetonitrile in 20 min, UV detection at 220 nm), k' 6.3 (5µ Altex Ultrasphere® ODS, 5% acetonitrile/water-0.1% trifluoroacetic acid, UV detection at 220 nm); Amino Acid Analysis: Asp(1.06), Gly(2.00), Pro(1.81), Arg(1.29).

Example 25

Preparation of cyclo-(1,6)-Gly-Arg-Gly-Asp-Ser-Pro

The protected hexapeptide resin FMOC-Asp(O-t-Bu)-Ser(Bzl)-Pro-Gly-Arg(Mtr)-Gly-SASRIN was prepared according to Example 20 on 1 mmol scale. After the removal of the N-terminal FMOC group with 20% piperidine in DMF, the resin-bound peptide was cleaved from the resin with 1% TFA in methylene chloride to give the protected linear peptide as a white solid (863 mg, 91%). The protected peptide (703 mg, 0.8 mmol) in DMF (2 L) was treated with NMM (440 µL, 4.0 mmol) and PPA (608 µL, 0.95 mmol) at 0° C. After stirring at 0° C. for 1 h, another portion of PPA was added and stirring was continued for 18 h. Removal of the solvent and trituration of the residue with water gave the cyclized protected peptide (328 mg, 88%). The peptide (300 mg) was treated with anhydrous HF (20 mL) in the presence of anisole (2 mL) at 0° C. for 50 min. After removal of HF under vacuum, the deprotected peptide was dissolved in of 0.2M acetic acid (60 mL), washed with ether (3×20 mL) and lyophilized to give the crude cyclo-(1,6)-Pro-Gly-Arg-Gly-Asp-D-Pro (256 mg). An aliquot of the crude peptide (172 mg) was purified by gel filtration (Sephadex® G-15, 1% acetic acid/water). The appropriate fractions were pooled and lyophilized. An aliquot of partially purified peptide (50 mg) was further purified by HPLC (5µ Altex Ultrasphere® ODS, 4% acetonitrile/water-0.1% trifluoroacetic acid, UV detection at 220 nm) to yield the purified titled compound (33 mg). MS(FAB) m/e 570.3 [M+H]⁺; TLC $R_f$ 0.42 (n-BuOH:HOAc:H$_2$O:EtOAc 1:1:1:1), $R_f$ 0.45 (n-BuOH:HOAc:H$_2$O:pyridine 15:5:10:10); HPLC k' 6.3 (5µ Altex Ultrasphere® ODS, gradient, A:acetonitrile B:water-0.1% trifluoroacetic acid, 0–50% acetonitrile in 20 min, UV detection at 220 nm), k' 6.0 (5µ Altex Ultrasphere® ODS, 2.5% acetonitrile/water-0.1% trifluoroacetic acid, UV detection at 220 nm); Amino Acid Analysis: Asp(0.94), Gly(2.00), Pro(1.03), Arg(1.03), Ser(0.9)

Example 26

Preparation of cyclo-(1,6)-Pro-Arg-Gly-Asp-Gly-D-Pro

The protected hexapeptide resin FMOC-Asp(O-t-Bu)-Gly-D-Pro-Pro-Arg(Tos)-Gly-SASRIN was prepared according to Example 20 on 1 mmol scale. After the removal of the N-terminal FMOC group with 20% piperidine in DMF, the resin-bound peptide was cleaved from the resin with 2% TFA in methylene chloride to give the protected linear peptide as a white solid (663 mg, 82%). The protected peptide (646 mg, 0.8 mmol) in DMF (1.4 L) was treated with NMM (440 µL, 4.0 mmol) and PPA (604 µL, 0.96 mmol) at 0° C. After stirring at 0° C. for 1 h, another portion of PPA was added and stirring was continued for 18 h. Removal of the solvent and trituration of the residue with water gave the cyclized protected peptide, cyclo-(1,6)-Pro-Arg(Tos)-Gly-Asp(O-t-Bu)-Gly-D-Pro (400 mg, 63%). The protected peptide (400 mg) was treated with anhydrous HF (20 mL) in the presence of anisole (2 mL) at 0° C. for 50 min. After removal of HF under vacuum, the deprotected peptide was dissolved in 0.2M acetic acid (60 mL), washed with ether (3×20 mL) and lyophilized to give the crude cyclo-(1,6)-Pro-Arg-Gly-Asp-Gly-D-Pro. An aliquot of the crude peptide (75 mg) was purified by HPLC (5µ Altex Ultrasphere® ODS, 7% acetonitrile/water-0.1% trifluoroacetic acid, UV detection at 220 nm) to yield the purified titled compound (35 mg). MS(FAB) m/e 580.5 [M+H]$^+$; TLC R$_f$ 0.35 (n-BuOH:HOAc:H$_2$O:EtOAc 1:1:1:1), R$_f$ 0.5 (n-BuOH:HOAc:H$_2$O:pyridine 15:5:10:10); HPLC k' 6.7 (5μ Altex Ultrasphere® ODS, gradient, A:acetonitrile B:water-0.1% trifluoroacetic acid, 1%–50% acetonitrile in 20 min, UV detection at 220 nm), k' 4.8 (5μ Altex Ultrasphere® ODS, 5.5% acetonitrile/water-0.1% trifluoroacetic acid, UV detection at 220 nm); Amino Acid Analysis: Asp(1.00), Gly(1.94), Pro(2.05), Arg(1.02).

Example 27

Preparation of cyclo-(1,6)-Pro-Arg-Gly-Asp-Gly-D-Phe

The protected hexapeptide resin FMOC-Asp(O-t-Bu)-Gly-D-Phe-Pro-Arg(Mtr)-Gly-SASRIN was prepared according to Example 20 on 1 mmol scale. After the removal of the N-terminal FMOC group with 20% piperidine in DMF, the resin-bound peptide was cleaved from the resin with 2% TFA in methylene chloride to give Asp(O-t-Bu)-Gly-D-Phe-Pro-Arg(Tos)-Gly as a white solid (936 mg, 100%). The protected peptide (733 mg, 0.8 mmol) in DMF (1.6 L) was treated with NMM (440 μL, 4.0 mmol) and PPA (604 μL, 0.96 mmol) at 0° C. After stirring at 0° C. for 1 h, another portion of PPA was added and stirring was continued for 18 h. Removal of the solvent and trituration of the residue with water gave the cyclized protected peptide, cyclo(1,6)-Asp(O-t-Bu)-Gly-D-Phe-Arg(Tos)-Gly (606 mg, 84%). The protected peptide was treated with anhydrous HF (20 mL) in the presence of anisole (2 mL) at 0° C. for 50 min. After removal of HF under vacuum, the unprotected peptide was taken into 60 mL of 0.2M acetic acid, washed 3 times with ether (20 mL) and lyophilized to give the crude cyclo-(1,6)-Pro-Arg-Gly-Asp-Gly-D-Phe (462 mg). An aliquot of the crude peptide (211 mg) was purified by gel filtration (Sephadex® G-15, 1% acetic acid/water). The appropriate fractions were pooled and lyophilized to yield a semipurified peptide (178 mg). An aliquot of the semipurified peptide (67 mg) was purified by HPLC (5μ Altex Ultrasphere® ODS, 15% acetonitrile/water-0.1% trifluoroacetic acid, UV detection at 220 nm) to yield the purified titled compound (53 mg). MS(FAB) m/e 630.3 [M+H]$^+$; TLC R$_f$ 0.64 (n-BuOH:HOAc:H$_2$O:EtOAc 1:1:1:1), R$_f$ 0.64 (n-BuOH:HOAc:H$_2$O:pyridine 15:5:10:10); HPLC k' 8.5 (5μ Altex Ultrasphere® ODS, gradient, A:acetonitrile B:water-0.1% trifluoroacetic acid, 1%–50% acetonitrile in 20 min, UV detection at 220 nm), k' 5.98 (5μ Altex Ultrasphere® ODS, 13% acetonitrile/water-0.1% trifluoroacetic acid, UV detection at 220 nm); Amino Acid Analysis: Asp(1.00), Gly(1.98), Pro(1.04), Phe(0.97), Arg(1.03).

Example 28

Preparation of cyclo-(1,5)-D-Ala-Arg-Gly-Asp-Ser

The protected hexapeptide resin FMOC-Asp(Bzl)-Ser(Bzl)-D-Ala-Arg(Tos)-Gly-SASRIN was prepared according to Example 20 on 1 mmol scale. After the removal of the N-terminal FMOC group with 20% piperidine in DMF, the resin-bound peptide was cleaved from the resin with 1% TFA in methylene chloride to give Asp(Bzl)-Ser(Bzl)-D-Ala-Arg(Tos)-Gly as a white solid (400 mg, 64%). The protected peptide (168 mg, 0.2 mmol) in DMF (0.5 L) was treated with NMM (10 μL, 1.0 mmol) and PPA (152 μL, 0.24 mmol) at 0° C. After stirring at 0° C. for 1 h, another portion of PPA was added and stirring was continued for 18 h. Removal of the solvent and trituration of the residue with water gave the cyclized protected peptide, cyclo-(1,5)-D-Ala-Arg(Tos)-Gly-Asp(Bzl)-Ser(Bzl) (164 mg, 67%). The protected peptide was treated with anhydrous HF (10 mL) in the presence of anisole (1 mL) at 0° C. for 50 min. After removal of HF under vacuum, the deprotected peptide was dissolved in of 0.2M acetic acid (30 mL), washed with ether (3×10 mL) and lyophilized to give the crude cyclo-(1,5)-D-Ala-Arg-Gly-Asp-Ser (73 mg). The crude peptide (70 mg) was purified by HPLC (5μ Altex Ultrasphere® ODS, 1.5% acetonitrile/water-0.1% trifluoroacetic acid, UV detection at 220 nm) to yield the purified titled compound (28 mg). MS(FAB) m/e 487.1 [M+H]$^+$; TLC R$_f$ 0.41 (n-BuOH:HOAc:H$_2$O:EtOAc 1:1:1:1), R$_f$ 0.43 (n-BuOH:HOAc:H$_2$O:pyridine 15:5:10:10); HPLC k' 10.6 (5μ Altex Ultrasphere® ODS, gradient, A:acetonitrile B:water-0.1% trifluoroacetic acid, 0–50% acetonitrile in 20 min, UV detection at 220 nm), k' 11.4 (5μ Altex Ultrasphere® ODS, 1.5% acetonitrile/water-0.1% trifluoroacetic acid, UV detection at 220 nm); Amino Acid Analysis: Asp(1.00), Gly(0.93), Ser(0.95), Ala(0.95), Arg(1.07).

Example 29

Preparation of cyclo-(1,5)-Ala-Arg-Gly-Asp-D-Ser

The protected hexapeptide resin FMOC-Asp(O-t-Bu)-D-Ser(Bzl)-Ala-Arg(Mtr)-Gly-SASRIN was prepared according to Example 20 on 1 mmol scale. After the removal of the N-terminal FMOC group with 20% piperidine in DMF, the resin-bound peptide was cleaved from the resin with 2% TFA in methylene chloride to give Asp(O-t-Bu)-D-Ser(Bzl)-Ala-Arg(Mtr)-Gly as a white solid (860 mg, 100%). The protected peptide (345 mg, 0.4 mmol) in DMF (1 L) was treated with NMM (220 μL, 2.0 mmol) and PPA (304 μL, 0.48 mmol) at 0° C. After stirring at 0° C. for 1 h, another portion of PPA was added and stirring was continued for 18 h. Removal of the solvent and trituration of the residue with water gave the cyclized protected peptide, cyclo-(1,5)-Ala-Arg(Mtr)-Gly-Asp(O-t-Bu)-D-Ser(Bzl) (227 mg, 67%). The protected peptide was treated with anhydrous HF (20 mL) in the presence of anisole (2 mL) at 0° C. for 50 min. After removal of HF under vacuum, the deprotected peptide was dissolved in 0.2M acetic acid (60 mL), washed with ether (3×20 mL) and lyophilized to give the crude cyclo-(1,5)-Ala-Arg-Gly-Asp-D-Ser (208 mg). The crude peptide (70 mg) was purified by gel filtration (Sephadex® G-15, 1% acetic acid/water). The appropriate fractions were pooled and lyophilized to yield the purified titled compound (71 mg). MS(FAB) m/e 487.2 [M+H]$^+$; TLC R$_f$ 0.49 (n-BuOH:HOAc:H$_2$O:EtOAc 1:1:1:1), R$_f$ 0.38 (n-BuOH:HOAc:H$_2$O:pyridine 15:5:10:10); HPLC k' 5.5 (5μ Altex Ultrasphere® ODS, gradient, A:acetonitrile B:water-0.1% trifluoroacetic acid, 0–50% acetonitrile in 20 min, UV detection at 220 nm), k 7.65 (5μ Altex Ultrasphere® ODS, 1.5% acetonitrile/water-0.1% trifluoroacetic acid, UV detection at 220 nm); Amino Acid Analysis: Asp(0.98), Gly(1.00), Ser(0.92), Ala(1.01), Arg(1.06).

Example 30

Preparation of cyclo-(1,3)-N$^α$-[2-(2-(2-amido-phenyl)ethyl)benzoyl]-MeArg-Gly-Asp-amide a) 2-[2-(2-aminophenyl)ethyl]benzoic acid hydrochloride A suspension of 5,6,11,12-tetrahydrodibenz[b,f]azocin-6-one (8.5 g, 38 mmol) in hydrochloric acid (6N, 500 mL) was heated to reflux for 16 h. The reaction mixture was filtered hot to remove unreacted starting material, cooled and filtered again to give 2-[2-(2-aminophenyl)ethyl]benzoic acid hydrochloride (10.5 g, 88%).

b) 2-[2-(2-(phenylmethoxycarbonylamino)phenyl)ethyl]benzoic acid

A suspension of 2-[2-(2-aminophenyl)ethyl]benzoic acid hydrochloride (339 mg, 1 mmol) in aqueous sodium hydroxide (1N, 2 mL) was stirred vigorously and treated simultaneously with benzyl chloroformate (170 mg, 1 mmol) and aqueous sodium hydroxide (1N, 1 mL). The reaction mixture was stirred for 16 h, acidified with dilute hydrochloric acid and filtered. The solid was washed with water and hexane, dissolved with methylene chloride, and the organic phase was washed with water, dried with magnesium sulfate, filtered and concentrated in vacuo. The resulting solid was triturated with ether to give 2-[2-(2-(phenylmethoxycarbonylamino)phenyl]ethyl]benzoic acid (0.2 g, 53%).

c) t-butyl 2-[2-(2-(phenylmethoxycarbonylamino)phenyl)ethyl]benzoate

A solution of 2-[2-(2-(phenylmethoxycarbonylamino)phenyl)ethyl]benzoic acid (5.2 g, 0.014 mol) in methylene chloride (100 mL) was treated with isobutylene (15 mL) and sulfuric acid (0.14 mL) and stirred at room temperature. Isobutylene was added over the period of several days until the reaction was complete. The reaction mixture was washed with 5% aqueous sodium carbonate and with water. The organic phase was dried with magnesium sulfate and concentrated in vacuo to give an oil which was purified by chromatography (silica gel, hexane:ethyl acetate 95:5) to give t-butyl 2-[2-(2-(phenylmethoxycarbonylamino)phenyl)-ethyl]-benzoate (1.8 g, 31%).

d) t-butyl 2-[2-(2-aminophenyl)ethyl]benzoate

A solution of t-butyl 2-[2-((phenylmethoxycarbonylamino)phenethyl]benzoate (1.8 g, 4 mmol) in ethanol (140 mL) was treated with 10% palladium-on-carbon (250 mg) was shaken with hydrogen until uptake ceased. The mixture was degassed, filtered and concentrated in vacuo. The residue was purified by chromatography (silica gel, petroleum ether:ethyl ether 9:1) to give t-butyl 2-[2-(2-aminophenyl)ethyl]benzoate (1.0 g). mp 58°–59° C.

e) t-butyl 2-[2-(2-(N$^\alpha$-FMOC-Asp(O-Bzl)-amino)phenyl)ethyl]benzoate

To a cold solution of FMOC-Asp(O-Bzl) (490 mg, 1.1 mmol) in THF (5 mL) and N-methylmorpholine (133 µL, 1.2 mmol), was added isobutylchloroformate (156 µL, 1.2 mmol) dropwise. The reaction mixture was stirred for a few minutes, then a solution of t-butyl [2-(2-aminophenethyl)] benzoate was added (295 mg, 1.0 mmol) in THF (3 mL). The reaction mixture was allowed to warm to room temperature, and stirred for 18 h. Upon completion of the reaction (TLC monitored), the reaction mixture was concentrated to dryness. The residue was dissolved in ethyl acetate (40 mL), and washed successively with water (3×15 mL), 10% aqueous $Na_2CO_3$ (2×15 mL), water (3×15 mL) and saturated salt solution (1×15 mL). The organic solvent was dried (anhydrous $Na_2SO_4$), filtered and concentrated to yield the titled compound (700 mg).

f) t-butyl 2-[2-(2-(Gly-Asp(O-Bzl)-amino)phenyl)ethyl)]benzoate t-Butyl 2-[2-(2-(N$^\alpha$-FMOC-Asp(O-Bzl)-amino)phenyl)ethyl]benzoate (580 mg, 0.8 mmol) was treated with piperidine (8 mL, 10% in DMF) for 45 min at room temperature. The solvent was removed under vacuum to yield t-butyl [2-(2-Asp(O-Bzl)-aminophenethyl)]bezoate as a white solid. To a solution of the residue in dry DMF (8 mL) was added HOBt (135 mg, 0.88 mmol), FMOC-Gly (262 mg, 0.88 mmol) and DIEA (153 µL, 0.88 mmol), followed by EDC (170 mg, 0.88 mmol) and stirred overnight. The reaction mixture was concentrated to dryness and the residue was dissolved in ethyl acetate. The ethyl acetate extract was washed successively with water (3×15 mL), 10% aqueous $NaHCO_3$ (2×15 mL), water (3×15 mL) and saturated salt solution (1×15 mL). The organic solvent was dried (anhydrous $Na_2SO_4$), filtered and concentrated to yield the titled compound, which was recrystallized from ether-hexane (190 mg). The FMOC group on the N$^\alpha$-FMOC-Gly was apparently lost during work-up.

g) t-butyl 2-[2-(2-(Boc-MeArg(Tos)-Gly-Asp(O-Bzl)-amino)phenyl)ethyl]benzoate

To a cold solution of the compound of Example 30f (140 mg, 0.25 mmol) and Boc-MeArg(Tos) (133 mg, 0.3 mmol) in DMF (2 mL), was added DIEA (87 µL, 0.5 mmol) and HOBt (50 mg, 0.3 mmol). The reaction mixture was stirred in the cold for a few min, then EDC (60 mg, 0.3 mmol) was added portionwise. The reaction mixture was allowed to warm to room temperature and stirred for 18 h. The reaction mixture was concentrated to dryness. The residue was taken into ethyl acetate, and washed successively with water (3×15 mL), 10% aqueous $NaHCO_3$ (2×15 mL), water (3×15 mL) and saturated salt solution (1×15 mL). The organic solvent was dried (anhydrous $Na_2SO_4$), filtered and concentrated to yield the titled compound (120 mg).

h) 2-[2-(2-(MeArg(Tos)-Gly-Asp(O-Bzl)-amino)phenylethyl]benzoic acid

The compound of Example 30g is treated with 50% TFA solution in methylene chloride, at room temperature for 2 h. The solvent is removed and methylene chloride is evaporated from the residue several times to eliminate traces of TFA to yield the titled compound.

i) cyclo-(1,3)-N$^\alpha$-[2-(2-(2-amido-phenyl)ethyl)benzoyl]-MeArg-Gly-Asp-amide To the protected linear peptide of Example 30h, NMM (5 equivalent) was added, followed by PPA (1.2 equivalent) at 0° C. After stirring 1 h at 0° C., another portion of PPA was added and stirring was continued for 18 h. Removal of the solvent and trituration of the residue with water yields the cyclized protected peptide cyclo(1,3)-N$^\alpha$-[2-(2-amido-phenethyl)benzoyl]-MeArg(Tos)-Gly-Asp(O-Bzl)amide. The cyclic peptide is treated with anhydrous HF in the presence of anisole at 0° C. for 50 min. After removal of HF under vacuum, the unprotected peptide is dissolved in acetic acid, washed with ether and lyophilized to yield the titled compound.

Example 31

Preparation of (2R,3S)-3-phenylcysteine a) (4S)-3-(((4'S,5'R)-5'-phenyl-2'-thioxo-4'-oxazolidinyl)carbonyl)-4-(phenylmethyl)-2-oxazolidinone (1)

To a −78° C. suspension of freshly prepared stannous triflate (washed under argon with anhydrous ether three times previously) (7.2 g, 17.6 mmol) and N-ethylpiperidine in dry THF (60 mL) 3-(isothiocyanoacetyl)-2-oxazolidinone (4.4 g, 15.8 mmol) in THF (20 mL) was added. The pale yellow solution was stirred at −78° C. for 2 h allowing the solution to warm to −40° C. for 5 min, after cooling again at −78° C., benzaldehyde (2.02 g, 19.1 mmol) was added heat. After the reaction mixture was stirred at −78° C. for 2.5 h, it was quenched by the addition of 40 mL of aqueous pH 7 phosphate buffer. The resultant slurry was filtered through Celite®. The filtrate was diluted with 200 mL of 1N aqueous sodium bisulfate and extracted with $Cl_2CH_2$ (3×). The combined organic phases were dried over anhydrous sodium sulfate and concentrated. Volatiles were removed in vacuo. The residue was dissolved in 200 mL of aqueous sodium bisulfate. The residue was purified by flash column chromatography (silica, methylene chloride) to afford the title compound 1 (5.3 g, 87%). $^1$H NMR (CDCl$_3$).δ2.980 (dd, J=13.6, 8.5 Hz, 1H, CH<u>H</u>Ph), 3.236 (dd, J=13.6, 3.5 Hz, 1H, CHHPh), 4.350–4.382 (m, 2H, H-5), 4.729–4.823 (m, 1H, H-4), 4.986 (dd, J=5.2, 1.9 Hz, 1H, C(S)NHCH), 6.467 (d, J=5.2 Hz, 1H, C(S)OCH), 7.206–7.449 (m, 10H).

b) methyl(4S,5R)-5-phenyl-2-thiooxazolidine-4-carboxylate (2)

To a 0° C. solution of aldol product 1 (6.96 g, 18.2 mmol) in anhydrous methanol (42 mL) and $Cl_2CH_2$ (42 mL) was added via canula a suspension formed by the addition of methylmagnesium bromide (6.7 mL, 20.02 mmol, 1.1 equiv., 3M in diethyl ether) to anhydrous methanol (25 mL). After the reaction mixture was stirred for 3 min, it was quenched by the addition of 50 mL of 1N aqueous sodium bisulfate. Volatiles were removed in vacuo. The residue was dissolved in 200 mL of aqueous sodium bisulfate and extracted with of $Cl_2CH_2$ (3×). The combined organic phases were dried over anhydrous sodium sulfate and concentrated. The residue was purified by flash column chromatography (silica, 5:5:1 methylene chloride/ether/methanol) to afford of the title compound (4.18 g, 96%) 2. $^1H$ NMR ($CDCl_3$).δ3.875 (s, 3H), 4.534 (d, J=6.1 Hz, 1H, H-4), 5.967 (d, J=6.1 Hz, 1H, H-5), 7.414 (s, 5H); $^{13}C$ NMR ($CDCl_3$).δ53.4, 64.6, 85.6, 125.6, 129.1, 129.5, 136.7, 168.5, 188.8.

c) methyl(4S,5R)3-((tert-butyloxycarbonyl)-5-phenyl-2-oxazolidine-4-carboxylate (3)

To a well-stirred solution of the thiooxazolidinone 2 (4.18 g, 17.6 mmol) in $Cl_2CH_2$ (80 mL) at room temperature di-t-butyl pyrocarbonate (4.25 g, 19.36 mmol) and dimethylaminopyridine (110 mg, 0.05 equiv.) were added dissolved in $Cl_2CH_2$ (8 mL). After the reaction mixture was stirred for 30 min, it was cooled to 0° C. and 30% aqueous $H_2O_2$ (44 mL) and 88% formic acid (44 mL) were added. The resultant two-phase mixture was stirred for 30 min and then poured into 1M aqueous potassium carbonate (500 mL). The aqueous solution was extracted with $Cl_2CH_2$ (3×). The combined organic phases were washed with 1M aqueous potassium carbonate, dried over anhydrous sodium sulfate, and concentrated to give a foamy oil (5.6 g, 100%). The oil was purified by a flash column chromatography (30% ethyl acetate/hexane) to give the desired Boc protected oxazolidinone 3 (5.4 g, 95%). $^1H$ NMR ($CDCl_3$).δ1.504 (s, 9H), 3.385 (s, 3H), 4.642 (d, J=4.3 Hz, 1H, H-4), 5.389 (d, J=4.3 Hz, 1H, H-5), 7.401–7.462 (m, 5H); $^{13}C$ NMR ($CDCl_3$).δ28.2, 53.3, 63.8, 76.0, 84.9, 125.2, 129.3, 129.6, 137.3, 150.8, 169.1.

d) methyl(2S,3R)2-((tert-butyloxycarbonyl)amino)-3-hydroxy-3-phenylpropionate (4)

To a room temperature solution of methyl ester 3 (5.6 g, 17.6 mmol) in dioxane (300 mL) was added freshly prepared 2N aqueous lithium hydroxide solution (44 mL, 88 mmol). The resultant suspension was stirred at room temperature overnight. Volatiles were removed in vacuo. The residue was dissolved in 1N aqueous sodium bisulfate (300 mL) and extracted with $Cl_2CH_2$ (3×). The combined organic phases were dried over sodium sulfate and concentrated, the residue was then redissolved in ether (300 mL) and, after cooling to 0° C., a solution of ethereal diazomethane was added until a pale yellow color persisted. The solution was stirred at 0° C. for 15 min and at room temperature for 30 min. The solvent was eliminated and the residual foamy oil was purified by flash column chromatography (silica, step gradient: 30% ethyl acetate-hexane, 50% ethyl acetate/hexane) to give the desired Boc protected amino alcohol 4 (4.01 g, 81%) followed by the de-Boc oxazolidinone (460 mg, 12%). The amino alcohol 4 was obtained as a white solid, which crystallized. mp 101°–102° C. (ether-hexane); [α]$^{20}_D$=−15.1° (c=0.93, $CHCl_3$); $^1H$ NMR ($CDCl_3$).δ1.333 (s, 9H), 2.704 (bs, 1H, OH), 3.761 (s, 3H), 4.501 (bd, J=6.6 Hz, 1H, HO—), 5.237 (dd, J=3.5, 3.4 Hz, 1H), 5.273–5.351 (m, 1H), 7.287–7.362 (m, 5H); $^{13}C$ NMR ($CDCl_3$).δ28.1, 52.4, 59.5, 73.8, 80.0, 126.0, 127.9, 128.2, 139.9, 155.5, 171.5; IR (KBr) 3440 (br), 2980, 1745, 1705, 1525, 1165 cm$^{-1}$; MS m/z 296 [M+H]$^+$; Anal. Calcd. for $C_{15}H_{21}O_5N$: C, 61.02; H, 7.12. Found: C, 59.96; H, 6.94.

e) methyl(2S,3R)-2-((tert-butyloxycarbonyl)amino)-3-methanesulfonyl-3-phenylpropionate (6)

To a solution of alcohol 4 (0.94 g, 3.18 mmol) and $NEt_3$ (0.73 g, 7.18 mmol) at 0° C. in $Cl_2CH_2$ (10 mL), methanesulfonyl chloride (418 mg, 3.65 mmol) was added. The reaction mixture was allowed to stir at 0° C. for 45 min. It was then quenched with cold dilute HCl, diluted with $Cl_2CH_2$ and the organic layer was washed with an aqueous solution of $NaHCO_3$ followed by brine and dried over $Na_2SO_4$. The solvent was eliminated in vacuo and the crude mesylate 6 was obtained as a foamy white solid which was used in the next step without further purification. $^1H$ NMR ($CDCl_3$).δ1.417 (s, 9H), 2.910 (s, 3H, $CH_3$—OMs), 3.705 (s, 3H, $CH_3O$—), 4.853 (dd, J=9.6, 6.6 Hz, 1H, H—$C_2$), 5.173 (bd, J=9.6 Hz, 1H, H—N), 5.893 (d, J=6.6 Hz, 1H, H—$C_3$), 7.389–7.400 (m, 5H); IR (KBr) 3400, 2980, 2950, 1745, 1715, 1520, 1360, 1180 cm$^{-1}$.

f) methyl(2R,3S)3-(acetylthio)2-((tert-butyloxycarbonyl)amino)-3-phenylpropionate (7)

To a solution of mesylate 6 (1.18 g, 3.16 mmol) in DMF (10 mL) a preformed solution of the DBU salt of thiolacetic acid (formed by adding thiolacetic acid (1.2 g, 15.8 mmol) to a solution of DBU (1.68 g, 11.07 mmol) in DMF (5 mL)) was added. The reaction mixture was allowed to stir at room temperature for 30 h. It was then quenched with water diluted with $Cl_2CH_2$ and washed with water (4×). The organic layer was washed with brine and dried over $Na_2SO_4$. The solvent was removed in vacuo and the crude oil was purified by flash column chromatography (silica, 8% ethyl acetate/toluene to give the desired acetylated thiol 7 (0.97 g, 87%) as a colorless liquid. [α]$^{20}_D$=+143.6° (c=2.50, $CHCl_3$); $^1H$ NMR ($CDCl_3$).δ1.427 (s, 9H), 2.330 (s, 3H, $CH_3$—COS), 3.685 (s, 3H, $CH_3O$—), 4.903 (dd, J=9.6, 4.7 Hz, 1H, H—$C_2$), 5.073 (bd, J=9.6 Hz, 1H, H—N), 5.138 (d, J=4.7 Hz, 1H, H—$C_3$), 7.289–7.400 (m, 5H); $^{13}C$ NMR ($CDCl_3$).δ28.1, 30.2, 49.9, 52.2, 57.3, 80.2, 128.2, 128.4, 128.6, 136.6, 155.1, 170.1, 193.3 (—COS—); IR (neat) 3380, 2990, 2960, 1750, 1690, 1520, 1340, 1170 cm$^{-1}$; MS m/z 354 [M+H]$^+$; Anal. Calcd. for $C_{17}H_{23}O_5NS$: C, 57.79; H, 6.51. Found: C, 57.64; H, 6.59.

g) methyl(2R,3S)-2-((tert-butyloxycarbonyl)amino)-3-mercapto-3-phenylpropionate (9)

The acetylated thiol 7 (290 mg, 0.82 mmol) was dissolved in methanol (4 mL) and NaOH was added (4.1 mL, 0.2N aqueous). The reaction was stirred at room temperature for 20 min (monitored by TLC). The solution was then carefully neutralized with dilute HCl. The volatiles were removed in vacuo and the residue was extracted with $Cl_2CH_2$ (3×). The organic layer was washed with brine and dried over $Na_2SO_4$. The crude product was purified by flash column chromatography (silica, 10% ethyl acetate/hexane) to give the desired thiol 9 (242 mg, 95%) as a white solid. mp 76°–77° C. (ether-hexane); [α]$^{20}_D$=+92.3 (c=0.96, $CHCl_3$); $^1H$ NMR ($CDCl_3$).δ1.392 (s, 9H), 2.207 (d, J=7.3 Hz, SH), 3.698 (s, 3H), 4.471 (dd, J=6.7, 6.3 Hz, 1H, CH—S), 4.800 (dd, J=8.7, 6.3 Hz, 1H, CH—N), 5.059 (bd, J=8.7 Hz, 1H, NH), 7.370–7.282 (m, 5H); $^{13}C$ NMR ($CDCl_3$).δ28.0, 52.1, 59.5, 80.1, 127.5, 127.6, 128.8, 138.8, 155.9, 171.5; IR (KBr) 3335, 2990, 1740, 1685, 1530, 1165 cm$^{-1}$; MS m/z 312 [M+H]$^+$;. Anal. Calcd. for $C_{15}H_{21}O_4NS$: C, 57.88; H, 6.75. Found: C, 58.08; H, 6.88.

h) (2R,3S)-2-((tert-butyloxycarbonyl)amino)-3-methylbenzyl)thio)-3-phenylpropionic acid (10)

The acetylated thiol 7 (520 mg, 1.47 mmol) was dissolved in methanol (8 mL) and NaOH was added (1.62 mL, 1M aqueous), followed by bromoxilene (300 mg, 1.62 mmol). After 20 min the pH was checked and an additional 1.1 equivalents of base were added. The reaction was allowed to stir at room temperature for 3 h (monitored by TLC). The solution was carefully neutralized with dilute HCl. The volatiles were removed in vacuo and the residue was extracted with $Cl_2CH_2$(3x). The organic layer was washed with brine and dried over $Na_2SO_4$. The crude product was purified by flash column chromatography (silica, 2% acetic acid/20% ethyl acetate/hexane) to give the desired acid 10 (480 mg, 79%) as a white solid. mp 131°–132° C. (ether-hexane); $[\alpha]^{20}_D$=+211.7° (c=0.99, $CHCl_3$); $^1H$ NMR ($CDCl_3$).δ1.403 (s, 9H), 2.316 (s, 3H), 3.515 (d, J=13 Hz, 1H), 4.194 (d, J=13 Hz, 1H), 4.790 (bs, 1H), 4.931–5.050 (m, 1H), 5.050–5.352 (bs, 1H), 7.082 (s, 4H), 7.287–7.307 (m, 5H); IR (KBr) 3380, 3000, 1700, 1515, 1170 $cm^{-1}$. MS m/z 402 [M+H]$^+$;. Anal. Calcd. for $C_{22}H_{27}O_4NS$: C, 65.81; H, 6.78. Found: C, 65.91; H, 7.00.

Example 32

Preparation of (2R,3R)-3-phenylcysteine:

a) (4R)-3-((2'R,3'S)-2'-bromo-3'-hydroxy-3'-phenylpropanoyl)-4-(phenylmethyl)-2-oxazolidinone (12)

To a −78° C. suspension of 3-(bromoacetyl)-2-oxazolidinone 11 (4.74 g, 15.9 mmol) in diethyl ether (30 mL) were added triethylamine (2.25 g, 22.2 mmol) and freshly distilled di-n-butylboryl triflate. The cooling bath was removed and the solution was stirred at room temperature for 2 h. The resultant two-phase brown mixture was gradually cooled to −78° C. and benzaldehyde was added neat (1.27 g, 11.9 mmol). After the reaction mixture was stirred at −78° C. for 30 min and 0° C. for 2.5 h, it was diluted with ether, washed with 1N aqueous sodium bisulfate (2x) and water, and concentrated. The residue was dissolved in ether (30 mL) and cooled to 0° C. The residue was added dropwise to mixture of methanol and 30% aqueous hydrogen peroxide (1:1, 30 mL). The reaction mixture was stirred at 0° C. for 1 h, then carefully poured into saturated aqueous sodium bicarbonate, and extracted with ether (2x). The combined organic phases were washed with saturated aqueous sodium bicarbonate (2x), dried over sodium sulfate, and concentrated to give a white solid, which was purified by flash column chromatography (silica, 2% ethyl acetate/methylene chloride) to yield the bromohydrine 12 (3.62 g, 75%).

b) (4R)-3-((2'S,3'S)-2'-azido-3'-hydroxy-3'-phenylpropanoyl)-4-(phenylmethyl)-2-oxazolidinone (13)

A solution of aldol adduct 12 (3.1 g, 7.67 mmol) and sodium azide (0.99 g, 15.3 mmol) in DMSO (26 mL) was stirred at room temperature for 5 h. The resultant dark solution was diluted with a 2:1 hexane/methylene chloride, washed with water (4x), dried over sodium sulfate, and concentrated to a pale oil, which crystallized. Purification by recrystallization from ether/hexane gave the azide 13 (2.2 g, 80%) as a white solid, which crystallized. mp 115°–116° C. (ether-hexane); $[\alpha]^{20}_D$=−6.6° (c=2.2, $CHCl_3$); $^1H$ NMR ($CDCl_3$).δ2.745 (dd, J=13.6, 9.6 Hz, 1H, CHH-Ph), 2.949 (d, J=6.6 Hz, 1H, —OH), 3.310 (dd, J=13.6, 3.4 Hz, 1H, CH HPh), 4.199–4.274 (m, 2H, H-5) 4.714–4.752 (m, 1H, H-4), 5.075 (dd, J=8.5, 6.6 Hz, 1H, CH—OH), 5.383 (d, J=8.5 Hz, 1H, CHN$_3$), 7.197–7.532 (m, 10H). $^{13}C$ NMR ($CDCl_3$) .δ37.3, 55.5, 63.1, 66.5, 74.8, 126.7, 127.3, 128.7, 128.8, 128.9, 129.3, 134.8, 139.5, 153.3, 169.6. IR (KBr) 3420, 3025, 2100, 2760, 1700, 1400, 1225 $cm^{-1}$. MS m/z 349 [M+H-H$_2$O]$^+$. Anal. Calcd. $C_{19}H_{18}O_4N_4$: C, 62.29; H, 4.95; N, 15.29. Found: C, 62.03; H, 5.06; N, 15.23.

c) methyl(2S,3S)-2-azido-3-hydroxy-3-phenylpropionate (14)

To a 0° C. solution of the azide 13 (1.52 g, 4.15 mmol) in anhydrous methanol (8 mL) and $Cl_2CH_2$ (8 mL), a suspension formed by the addition of methylmagnesium bromide (5.2 mL, 4.5 mmol, 0.88M in diethyl ether) was added via canula to anhydrous methanol (5 mL). After the reaction mixture was stirred for 3 min, it was quenched by the addition of 20 mL of 1N aqueous sodium bisulfate and extracted with methylene chloride (3x). The combined organic phases were dried over anhydrous sodium sulfate and concentrated. The residue was purified by flash column chromatography (silica, methylene chloride) to afford the title compound 14 (807 mg, 88%) as a white solid, which crystallized. mp 40°–41° C. (ether-hexane); $^1H$ NMR ($CDCl_3$).δ3.084 (bs, 1H, —OH), 3.774 (s, 3H), 4.108 (d, J=7 Hz, 1H, CH—N$_3$), 5.003 (bd, J=6.4 Hz, 1H, HC—OH), 7.372 (s, 5H); $^{13}C$ NMR ($CDCl_3$).δ52.6, 74.5, 126.6, 128.6, 128.7, 136.1, 169.3; IR (KBr) 3500 (b), 3020, 2960, 2120, 1740, 1460, 1440 $cm^{-1}$; MS m/z 238 [M+NH$_4$]; Anal. Calcd. $C_{10}H_{11}O_3N_3$): C, 54.30; H, 5.01; N, 19.00. Found: C, 54.31; H, 5.08; N, 18.78.

d) methyl(2S,3S)-2-((tert-butyloxycarbonyl)amino)-3-hydroxy-3-phenylpropionate (15)

Commercially available Palladium on charcoal (80 mg) in ethyl acetate (4 mL) was vigorously stirred under a hydrogen atmosphere for 15 min. To this suspension, a mixture of the azido alcohol 14 (800 mg, 3.6 mmol) and di-t-butyldicarbonate (943 mg, 4.32 mmol) in ethyl acetate (4 mL) was added. The resulting mixture was stirred under hydrogen at room temperature for 2 h (monitored by TLC) and was filtered through a Celite®. The filtrate was concentrated in vacuo and the white solid was purified by flash column chromatography (silica, 30% ethyl acetate/hexane) to give the desired Boc protected amino alcohol 15 (1.04 g, 98%) as a white solid, which crystallized. mp 101°–102° C. (ether-hexane); $[\alpha]^{20}_D$=+83.3° (c=1.05, $CHCl_3$); $^1H$ NMR ($CDCl_3$).δ1.433 (s, 9H), 3.701 (s, 3H), 3.929 (bd, J=5.3 Hz, 1H, HO—), 4.710–4.760 (m, 1H), 5.168–5.188 (m, 1H), 5.190–5.310 (m, 1H), 7.248–7.380 (m, 5H); $^{13}C$ NMR ($CDCl_3$).δ28.2, 52.2, 59.7, 74.9, 80.5, 126.0, 127.9, 128.2, 139.3, 156.1, 170.1; IR (KBr) 3450, 3390, 3000, 1760, 1710, 1530, 1280, 1260 $cm^{-1}$; MS m/z 296 [M+H]$^+$; Anal. Calcd. for $C_{15}H_{21}O_5N$: C, 61.02; H, 7.12. Found: C, 60.96; H, 6.96.

e) methyl(2S,3S)-2-((tert-butyloxycarbonyl)amino)-3-methanesulfonyl-3-phenylpropionate (16)

To a solution of alcohol 15 (1.94 g, 6.81 mmol) and triethylamine (1.25 g, 12.4 mmol) at 0° C. in $Cl_2CH_2$ (15 mL), methanesulfonyl chloride (0.96 g, 8.4 mmol) was added. The reaction mixture was allowed to stir at 0° C. for 20 min. It was quenched with cold dilute HCl, diluted with $Cl_2CH_2$ and the organic layer was washed with an aqueous solution of NaHCO$_3$ followed by brine and dried over Na$_2$SO$_4$. The solvent was removed in vacuo and the crude mesylate 16 was obtained as a foamy white solid, which was used in the next step without further purification. $^1H$ NMR ($CDCl_3$).δ1.394 (s, 9H), 2.916 (s, 3H), 3.718 (s, 3H), 4.878 (dd, J=8.7, 5.0 Hz, 1H, H-2), 5.231 (bd, J=8.7 Hz, 1H, H—N), 5.917 (d, J =5.0 Hz, 1H, H-3), 7.379–7.425 (m, 5H).

f) methyl(2R,3R)-3-(acetylthio)2-((tert-butyloxycarbonyl)amino)-3-phenylpropionate (17)

To a solution of mesylate 16 (2.72 g, 7.29 mmol) in DMF (7 mL) the potassium salt of thiolacetic acid (3 g, 29.9 mmol) was added at once. The solution became very thick and additional DMF was added (5 mL). The solution was kept under argon at room temperature for 20 h. It was quenched with water diluted with Cl$_2$CH$_2$ and washed with water (4×). The organic layer was dried over Na$_2$SO$_4$. The solvent was removed in vacuo. The crude product contained a 6:1 mixture of the desired product 17 and oxazolidinone 5 (as indicated by $^1$H NMR of the crude). This mixture was purified by flash column chromatography (silica, gradient, 5% to 50% ethyl acetate/hexane) to give the desired acetylated thiol 17 (1.65 g, 69%) as a tan solid followed by oxazolidinone 5 (193 mg, 12%). The acetylated thiol was recrystallized to produce a white solid. 87°–88° C. (ether-hexane); $[\alpha]^{20}_D$=–97.2° (1.0, CHCl$_3$); $^1$H NMR (CDCl$_3$) δ1.431 (s, 9H), 2.355 (s, 3H), 3.616 (s, 3H), 4.766 (dd, J=6.6, 6.3 Hz, 1H, H-2), 5.029 (bd, J=6.6 Hz, 1H, H-3), 5.264(bd, J=6.3 Hz, 1H, H—N), 7.311 (s, 5H); $^{13}$C NMR (CDCl$_3$).δ28.3, 30.2, 50.5, 52.2, 58.5, 80.3, 128.1, 128.3, 128.6, 137.8, 154.9, 170.6, 193.5. IR (KBr) 3380, 2990, 2960, 1745, 1690, 1520, 1240, 1170 cm$^{-1}$. MS m/z 354 [M+H]$^+$; Anal. Calcd. C$_{17}$H$_{23}$O$_5$NS: C, 57.77; H, 6.56; N, 3.97. Found: C, 58.05; H, 6.92; N, 3.73.

g) methyl(2R,3R)-2-((tert-butyloxycarbonyl)amino)-3-((4-methylbenzyl)thio)-3-phenylpropionic acid (18)

The acetylated thiol 17 (500 mg, 1.4 mmol) was dissolved in methanol (2 mL) and NaOH was added (1.6 mL, 1M aqueous), followed by bromoxilene (300 mg, 1.62 mmol). After 20 min most of the starting material has disappeared (monitored by TLC). The solution was carefully neutralized with dilute HCl. The volatiles were removed in vacuo and the residue was extracted with Cl$_2$CH$_2$ (3×) The organic layer was washed with brine and dried over Na$_2$SO$_4$. The crude product was purified by flash column chromatography (silica, 5% to 20% ethyl acetate/hexane) to give the desired ester 18 (480 mg, 79%) as a white solid, which crystallized. mp 97°–98° C. (ether-hexane); $[\alpha]^{20}_D$=–171.8° (c=1.05, CHCl$_3$); $^1$H NMR (CDCl$_3$).δ1.384 (s, 9H), 2.326 (s, 3H), 3.393 (d, J=13 Hz, 1H), 3.551 (d, J=13 Hz, 1H), 3.572 (s, 3H, OCH$_3$), 4.126 (d,J=5.4 Hz, H-3), 4.630 (dd, J=8.8, 5.8 Hz, 1H, H-2), 5.220 (bd, J=8.8 Hz, 1H, H—N), 7.028–7.107 (m, 4H), 7.291–7.362 (m, 5H); $^{13}$C NMR (CDCl$_3$).δ21.0, 28.3, 35.5, 51.6, 52.1, 57.5, 80.1, 127.8, 128.5, 128.7, 128.9, 129.2, 134.3, 136.9, 138.4, 154.7, 170.8; MS m/z 316 [M+H]$^+$; Anal. Calcd for C$_{23}$H$_{29}$O$_4$NS.¼H$_2$O: C, 65.76; H, 7.08; N, 3.33. Found: C, 65.59; H, 7.03; N, 3.36.

h) (2R,3R)-2-((tert-butyloxycarbonyl)amino)-3-((4-methylbenzyl)thio)-3-phenylpropionic acid (19)

The methyl ester 18 (380 mg, 0.91 mmol) and anhydrous lithium chloride (376 mg, 8.89 mmol) were dissolved in dry DMF (10 mL). The reaction mixture was heated at 90° C. for 4 days. The reaction mixture was cooled to room temperature, quenched with diluted HCl and extracted several times with ethyl acetate. The organic layer was washed with brine and dried over Na$_2$SO$_4$. The crude product was purified by flash column chromatography (silica, step gradient: 20% ethyl acetate/hexane, 25% ethyl acetate/5% acetic acid/hexane) to produce recovered starting material 18 (75 mg, 20%), followed by the desired carboxylic acid as a white solid, which was recrystallized (341 mg, 77%). mp 107°–108° C. (ether-hexane); $[\alpha]^{20}_D$=–143.7° (c=1.66, CHCl$_3$); $^1$H NMR (CDCl$_3$).δ1.379 (s, 9H), 2.300 (s, 3H), 3.460 (d, J=13.3 Hz, 1H), 3.588 (d, J=13.3 Hz, 1H), 4.242 (d,J=5.5 Hz, H-3), 4.646 (dd, J=8.7, 5.5 Hz, 1H, H-2), 5.273 (bd, J=8.7 Hz, 1H, H—N), 7.055 (s, 4H), 7.259–7.340 (m, 5H); $^{13}$C NMR (CDCl$_3$).δ 21.1, 28.2, 35.5, 50.8, 58.1, 80.5, 127.9, 128.6, 128.9, 129.2, 133.9, 136.9, 138.1, 155.3, 174.5; MS m/z 401 ([M+H]$^+$; Anal. Calcd. for C$_{22}$H$_{27}$O$_4$NS: C, 65.81; H, 6.78; N, 3.48. Found: C, 65.83; H, 6.92; N, 3.57.

Example 33

Parenteral Dosage Unit Composition A preparation which contains 20 mg of the compound of Example 1 or 2 as a sterile dry powder is prepared as follows: 20 mg of the compound is dissolved in 15 ml of distilled water. The solution is filtered under sterile conditions into a 25 ml multi-dose ampoule and lyophilized. The powder is reconstituted by addition of 20 ml of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 34

Oral Dosage Unit Composition

A capsule for oral administration is prepared by mixing and milling 50 mg of the compound of Example 3 with 75 mg of lactose and 5 mg of magnesium stearate. The resulting powder is screened and filled into a hard gelatin capsule.

Example 35

Oral Dosage Unit Composition

A tablet for oral administration is prepared by mixing and granulating 20 mg of sucrose, 150 mg of calcium sulfate dihydrate and 50 mg of the compound of Example 3 with a 10% gelatin solution. The wet granules are screened, dried, mixed with 10 mg starch, 5 mg talc and 3 mg stearic acid; and compressed into a tablet.

The above description fully discloses how to make and use this invention. This invention, however, is not limited to the precise embodiments described herein, but encompasses all modifications within the scope of the claims which follow.

What is claimed is:

1. A compound of the formula:

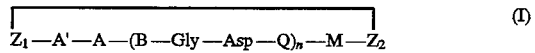

(I)

wherein:

A' is absent, Asn, Gln, Ala or Abu;

A is absent or a D- or L-amino acid chosen from Arg, HArg, NArg, (Me$_2$)Arg, (Et$_2$)Arg, Abu, Ala, Gly, His, Lys, or an α-R' substituted derivative thereof, Dtc, Tpr and Pro;

B is a D- or L-amino acid chosen from Arg, HArg, (Me$_2$)Arg, (Et$_2$)Arg and Lys or an α-R' substituted derivative thereof;

Q is absent or a D- or L-amino acid chosen from Tyr, (Alk)Tyr, Phe, (4'W)Phe, HPhe, Phg, Pro, Trp, His, Ser, (Alk)Ser, Thr, (Alk)Thr, (Alk)Cys, (Alk)Pen, Ala, Val, Nva, Met, Leu, Ile, Nle and Nal or an α-R' substituted derivative thereof;

M is absent or Gly or a D- or L-amino acid chosen from Glu, Phe, Pro, Lys and Ser or, provided n is 1, B-Gly-Glu-Q;

W is halogen or Alk;

R' is Alk or PhCH$_2$;

$Z_1$ is

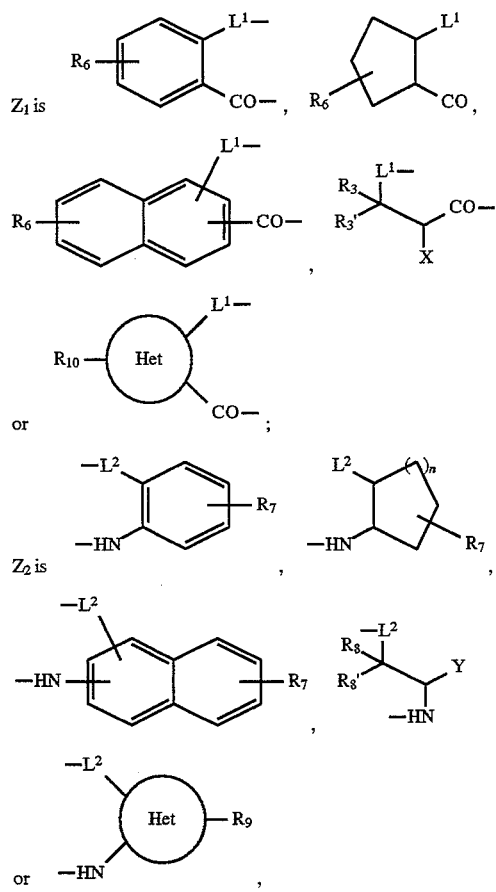

or $Z_2$ is wherein $Z_1$ and $Z_2$ are linked via a covalent bond between $L^1$ and $L^2$;

$L^1$ and $L^2$ are —S— or —(CH$_2$)$_p$—;

X is R$_4$R$_5$N;

Y is H, CONR$_1$R$_2$ or CO$_2$R$_2$;

R$_1$ and R$_2$ are H, Alk or (CH$_2$)$_p$Ar;

R$_3$ and R$_{3'}$ are H, Alk, (CH$_2$)$_p$Ar or taken together are —(CH$_2$)$_4$— or —(CH$_2$)$_5$—;

R$_4$ is H or Alk;

R$_5$ is R$_{11}$, R$_{11}$CO, R$_{11}$OCO, R$_{11}$OCH(R$_{11'}$)CO, R$_{11}$NHCH(R$_{11'}$)CO, R$_{11}$SCH(R$_{11'}$)CO, R$_{11}$SO$_2$ or R$_{11}$SO;

R$_6$ is Alk, OAlk, halogen or X;

R$_7$ is H, Alk, OAlk, halogen or Y;

R$_8$ and R$_{8'}$ are H, Alk, (CH$_2$)$_p$Ph, (CH$_2$)$_p$Nph or taken together are —(CH$_2$)$_4$— or —(CH$_2$)$_5$—;

R$_9$ is H, Alk or Y;

R$_{10}$ is H or Alk;

R$_{11}$ and R$_{11'}$ are H, C$_{1-5}$alkyl, C$_{3-7}$cycloalkyl, Ar, Ar—C$_{1-5}$alkyl, Ar—C$_{3-7}$cycloalkyl;

Ar is phenyl or phenyl substituted by one or two C$_{1-5}$alkyl, trifluoromethyl, hydroxy, C$_{1-5}$alkoxy or halogen groups;

n is 1 or 2;

q is 0 or 1; and p is 0, 1, 2 or 3 and pharmaceutically active salts thereof;

provided that when n is 1 and $Z_1$ is X-Cys, X-Pen or X-APmp, $Z_2$ is not Cys-Y, Pen-Y or APmp-Y.

2. A compound according to claim 1 in which $L^1$ and $L^2$ are each sulfur.

3. A compound according to claim 1 in which B is Arg, HArg or an α-R' substituted derivative of Arg or HArg.

4. A compound according to claim 2 in which A' and A are absent.

5. A compound according to claim 2 in which $Z_1$ is

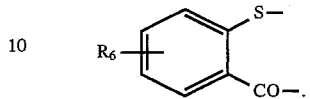

6. A compound according to claim 2 in which in which $Z_2$ is

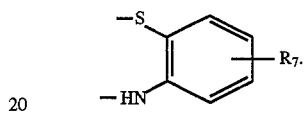

7. A compound according to claim 3 in which B is MeArg.

8. A compound according to claim 1 which is:

cyclo(S,S)-Mba-Arg-Gly-Asp-Cys-NH$_2$;
N$^α$-Ac-cyclo(S,S)-Cys-Arg-Gly-Asp-Man;
cyclo(S,S)-Mba-MeArg-Gly-Asp-Man;
cyclo(S,S)-Mba-MeArg-Gly-Asp-Pcs-NH$_2$;
cyclo-(S,S)-Mba-Sar-Arg-Gly-Asp-Man;
cyclo-(S,S)-Mba-Sar-MeArg-Gly-Asp-Man;
cyclo-(S,S)-Mba-Arg-Gly-Asp-Man;
cyclo-(S,S)-Mba-D-MeArg-Gly-Asp-Man;
cyclo-(S,S)-Mba-MeArg-Gly-Asp-N-Me-Man;
N$^α$Ac-cyclo-(S,S)-Cys-MeArg-Gly-Asp-(2R,3S)Pcs-NH$_2$;
N$^α$Ac-cyclo-(S,S)-Cys-MeArg-Gly-Asp-(2R,3R)Pcs-NH$_2$;
N$^α$Ac-cyclo-(S,S)Cys-Arg-Gly-Asp-Ser-Arg-Gly-Asp-Ser-Cys-NH$_2$;
N$^α$Ac-cyclo-(S,S)-Cys-Arg-Gly-Asp-Ser-Arg-Gly-Asp-Ser-Pen-NH$_2$;
N$^α$Ac-cyclo-(S,S)Cys-Arg-Gly-Asp-Ser-MeArg-Gly-Asp-Ser-Cys-NH$_2$; or
N$^α$Ac-cyclo-(S,S)-Cys-MeArg-Gly-Asp-Ser-Arg-Gly-Asp-Ser-Cys-NH$_2$.

9. A pharmaceutical composition which comprises a compound according to claim 1 and a pharmaceutically acceptable carrier.

10. A pharmaceutical composition which comprises a compound according to claim 9 and a pharmaceutically acceptable carrier.

11. A method of inhibiting platelet aggregation in a mammal in need thereof which comprises administering an effective amount of a compound according to claim 1.

12. A method for treating acute myocardial infarction in a mammal which comprises administering an effective amount of a compound according to claim 1.

13. A method for treating stroke or transient ischemia attacks in a mammal which comprises administering an effective amount of a compound according to claim 1.

14. A method for treating unstable angina in a mammal which comprises administering an effective amount of a compound according to claim 1.

15. A method for effecting thrombolysis and inhibiting reocclusion of an artery or vein in a mammal which comprises internally administering an effective amount of a fibrinolytic agent and an effective amount of a compound according to claim 1.

16. A method according to claim 15 in which the fibrinolytic is streptokinase (SK), urokinase (UK), pro-urokinase (pUK) or tissue plasminogen activator (tPA) or a mutant or derivative thereof.

17. A kit for use in a method for effecting thrombolysis and inhibiting reocclusion of an artery in a mammal which comprises, in separate containers, an effective amount of a fibrinolytic agent and an effective amount of a compound according to claim 1.

18. A compound of the formula:

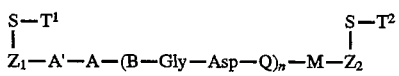

wherein:

A' is absent, Asn, Gln, Ala or Abu;

A is absent or a D- or L-amino acid chosen from Arg, HArg, (Me₂)Arg, (Et₂)Arg, Abu, Ala, Gly, His, Lys, or an α-R' substituted derivative thereof, Dtc, Tpr and Pro;

B is a D- or L-amino acid chosen from Arg, HArg, NArg, (Me₂)Arg, (Et₂)Arg and Lys or an α-R' substituted derivative thereof;

Q is absent or a D- or L-amino acid chosen from Tyr, (Alk)Tyr, Phe, (4'W)Phe, HPhe, Phg, Pro, Trp, His, Set, (Alk)Ser, Thr, (Alk)Thr, (Alk)Cys, (Alk)Pen, Ala, Val, Nva, Met, Leu, Ile, Nle and Nal, or an α-R' substituted derivative thereof;

M is absent or Gly or a D- or L-amino acid chosen from Glu, Phe, Pro, Lys and Ser or, provided n is 1, B-Gly-Glu-Q;

W is halogen or Alk;

R' is Alk or PhCH₂;

Z₁ is
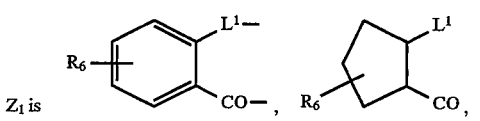
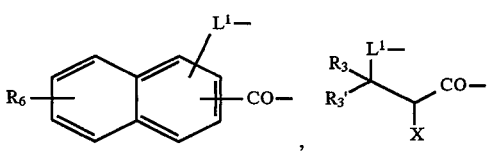
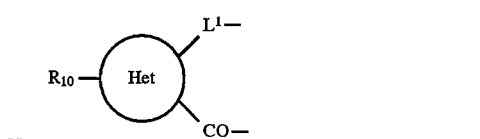

Z₂ is
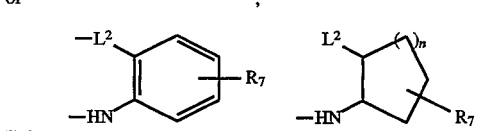
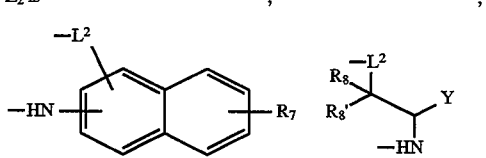

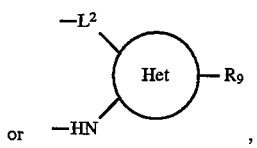

wherein Z₁ and Z₂ are linked via a covalent bond between L¹ and L²;

L¹ and L² are —S— or —(CH₂)$_p$—;

T is hydrogen or a displaceable group;

X is R₄R₅N or H;

Y is H, CONR₁R₂ or CO₂R₂;

R₁ and R₂ are H, Alk or (CH₂)$_p$Ar;

R₃ and R₃· are H, Alk, (CH₂)$_p$Ar or taken together are —(CH₂)₄— or —(CH₂)₅—;

R₄ is H or Alk;

R₅ is R₁₁, R₁₁CO, R₁₁OCO, R₁₁OCH(R₁₁·)CO, R₁₁NHCH(R₁₁·)CO, R₁₁SCH(R₁₁·)CO, R₁₁SO₂ or R₁₁SO;

R₆ is Alk, OAlk, halogen or X;

R₇ is H, Alk, OAlk, halogen or Y;

R₈ and R₈· are H, Alk, (CH₂)$_p$Ph, (CH₂)$_p$Nph or taken together are —(CH₂)₄— or —(CH₂)₅—;

R₉ is H, Alk or Y;

R₁₀ is H or Alk;

R₁₁ and R₁₁· are H, C₁₋₅alkyl, C₃₋₇cycloalkyl, Ar, Ar—C₁₋₅alkyl, Ar—C₃₋₇cycloalkyl;

Ar is phenyl or phenyl substituted by one or two C₁₋₅alkyl, trifluoromethyl, hydroxy, C₁₋₅alkoxy or halogen groups;

n is 1 or 2;

q is 0 or 1; and p is 0, 1, 2 or 3 and pharmaceutically active salts thereof;

provided that when n is 1 and Z₁ is X-Cys, X-Pen or X-APmp, Z₂ is not Cys-Y, Pen-Y or APmp-Y.

19. A compound according to claim 1 wherein if L¹ and L² are S, and if Z₁ is

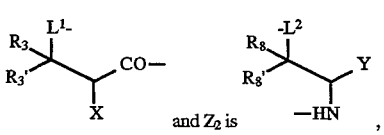

R₈ is phenyl.

20. A compound according to claim 19 in which Z₂ is Pcs.

21. A compound according to claim 1 which is N$^α$Ac-cyclo-(S,S)-Cys-MeArg-Gly-Asp-(2R,3S)Pcs-NH₂.

22. A compound according to claim 1 which is cyclo-(S, S)-Mba-MeArg-Gly-Asp-Man.

* * * * *